US011492340B2

(12) United States Patent
Hadad et al.

(10) Patent No.: US 11,492,340 B2
(45) Date of Patent: Nov. 8, 2022

(54) HETEROAROMATIC ELECTROPHILES AND METHODS OF USING THEREOF

(71) Applicant: OHIO STATE INNOVATION FOUNDATION, Columbus, OH (US)

(72) Inventors: Christopher Hadad, Dublin, OH (US); Christopher Callam, Blacklick, OH (US); Jeremy Beck, Columbus, OH (US); Qinggeng Zhuang, Columbus, OH (US); Andrew Franjesevic, Columbus, OH (US); Thomas Corrigan, Columbus, OH (US); Craig McElroy, Lancaster, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 0 days.

(21) Appl. No.: 16/486,448

(22) PCT Filed: Feb. 15, 2018

(86) PCT No.: PCT/US2018/018374
§ 371 (c)(1),
(2) Date: Aug. 15, 2019

(87) PCT Pub. No.: WO2018/152329
PCT Pub. Date: Aug. 23, 2018

(65) Prior Publication Data
US 2020/0010448 A1    Jan. 9, 2020

Related U.S. Application Data

(60) Provisional application No. 62/459,385, filed on Feb. 15, 2017.

(51) Int. Cl.
*C07D 401/06* (2006.01)
*C07D 213/65* (2006.01)
*C07D 401/14* (2006.01)
*C07D 413/06* (2006.01)
*A61P 29/00* (2006.01)

(52) U.S. Cl.
CPC ......... *C07D 401/06* (2013.01); *C07D 213/65* (2013.01); *C07D 401/14* (2013.01); *C07D 413/06* (2013.01); *A61P 29/00* (2018.01)

(58) Field of Classification Search
CPC .. A61K 31/44; A61K 31/4427; A61K 31/445; A61K 31/4439; A61K 31/4545; A61K 31/47; A61K 31/4709; A61K 31/496; A61K 31/5377; A61K 31/55; A61P 29/00; C07D 213/38; C07D 213/61; C07D 213/64; C07D 213/65; C07D 215/20; C07D 215/227; C07D 295/096; C07D 317/58; C07D 401/06; C07D 401/14; C07D 413/06
See application file for complete search history.

(56) References Cited

U.S. PATENT DOCUMENTS

| | | | |
|---|---|---|---|
| 4,295,861 A | 10/1981 | Burns | |
| 9,162,983 B2 | 10/2015 | Bauta et al. | |
| 9,249,100 B2 | 2/2016 | Quinn et al. | |
| 2014/0323473 A1* | 10/2014 | Quinn | A61K 31/5513 514/221 |
| 2016/0031854 A1* | 2/2016 | Stojanovic | C07D 233/60 514/312 |

FOREIGN PATENT DOCUMENTS

| | | |
|---|---|---|
| EP | 0330461 | 8/1989 |
| EP | 0770876 | 5/1997 |

OTHER PUBLICATIONS

Zhuang et al., Ann. NY Acad. Sci, Jun. 2016, vol. 1374(1), pp. 94-104 (1-20) (Year: 2016).*
International Search Report and Written Opinion issued by the International Searching Authority (US/ISA) in Application No. PCT/US2018/018374 dated Jul. 11, 2018. 15 pages.
Mercey, Guillaume, et al. "Reactivators of acetylcholinesterase inhibited by organophosphorus nerve agents." Accounts of chemical research 45.5 (2012): 756-766.
Pubchem CID 82982410. "6-Methyl-2-[(2-methylpyrrolidin-1-yl)methyl]pyridin-3-ol." Created Oct. 20, 2014. Downloaded May 30, 2018 https://pubchem.ncbi.nlm.nih.gov/compound/82982410. 10 pages.
Pubchem CID 251555. "2-(Pyrrolidin-1-ylmethyl)pyridin-3-ol." Created Mar. 26, 2005. Downloaded Apr. 9, 2018. https://pubchem.ncbi.nlm.nih.gov/compound/251555. 18 pages.
Pubchem CID 13553613. "1-Chloro-3-dimethylaminomethyl-4-isoquinolinol." Created Feb. 8, 2007. Downloaded Apr. 9, 2018. https://pubchem.ncbi.nlm.nih gov/compound/13553613. 11 pages.
Yoder, Ryan J., et al. "Study of para-Quinone Methide Precursors toward the Realkylation of Aged Acetylcholinesterase." ACS medicinal chemistry letters 8.6 (2017): 622-627.
Abdel-Magid, Ahmed F., et al. "Reductive amination of aldehydes and ketones with sodium triacetoxyborohydride. studies on direct and indirect reductive amination procedures1." The Journal of organic chemistry 61.11 (1996): 3849-3862.

(Continued)

*Primary Examiner* — Sarah Pihonak
(74) *Attorney, Agent, or Firm* — Meunier Carlin & Curfman LLC

(57) ABSTRACT

Disclosed herein are compounds, compositions, and methods for reactivating or realkylating aged acetylcholinesterase inhibited by or conjugated to the organophosphorus compound. The organophosphorus compound can be a nerve agent. The acetylcholinesterase can be in the central nerve system (CNS) and/or the peripheral nervous system (PNS) of a subject. Accordingly, methods for ameliorating, diminishing, reversing, treating or preventing the toxic effects of an organophosphorus compound in a subject are provided herein. Methods for prophylactic or therapeutic treatment of exposure to an organophosphorus nerve agent are also provided.

16 Claims, 9 Drawing Sheets

Specification includes a Sequence Listing.

(56) References Cited

OTHER PUBLICATIONS

Allgardsson, Anders, et al. "Structure of a prereaction complex between the nerve agent sarin, its biological target acetylcholinesterase, and the antidote HI-6." Proceedings of the National Academy of Sciences 113.20 (2016): 5514-5519.
Amitai, Gabi, et al. "Asymmetric fluorogenic organophosphates for the development of active organophosphate hydrolases with reversed stereoselectivity." Toxicology 233.1-3 (2007): 187-198.
An, Yun, et al. "Is it possible to reverse aged acetylcholinesterase inhibited by organophosphorus compounds? Insight from the theoretical study." Physical Chemistry Chemical Physics 18.14 (2016): 9838-9846.
Anglister, Lili, Joel R. Stiles, and Miriam M. Salpeter. "Acetylcholinesterase density and turnover number at frog neuromuscular junctions, with modeling of their role in synaptic function." Neuron 12.4 (1994): 783-794.
Ash, Arthur B., et al. "Relative nucleophilicity. Methylation of anions in aqueous media." The Journal of Organic Chemistry 34.12 (1969): 4070-4072. (originally listed Blumberg first).
Aurbek, N., et al. "Analysis of inhibition, reactivation and aging kinetics of highly toxic organophosphorus compounds with human and pig acetylcholinesterase." Toxicology 224.1-2 (2006): 91-99.
Bakke, Brian A., Matthias C. McIntosh, and Kenneth D. Turnbull. "Improved alkylation and product stability in phosphotriester formation through quinone methide reactions with dialkyl phosphates." The Journal of organic chemistry 70.11 (2005): 4338-4345.
Bannon, Pierre, and Walter Verly. "Alkylation of phosphates and stability of phosphate triesters in DNA." The FEBS Journal 31.1 (1972): 103-111.
Barak, Dov, et al. "Carbocation-mediated processes in biocatalysts. Contribution of aromatic moieties." Journal of the American Chemical Society 119.13 (1997): 3157-3158.
Benschop, H. P., and J. H. Keijer. "On the mechanism of ageing of phosphonylated cholinesterases." Biochimica et Biophysica Acta (BBA)—Enzymology and Biological Oxidation 128.3 (1966): 586-588.
Berdichevsky, Yevgeny, et al. "UV/ozone modification of poly (dimethylsiloxane) microfluidic channels." Sensors and Actuators B: Chemical 97.2-3 (2004): 402-408.
Briseno-Roa, Luis, et al. "Analogues with fluorescent leaving groups for screening and selection of enzymes that efficiently hydrolyze organophosphorus nerve agents." Journal of medicinal chemistry 49.1 (2006): 246-255.
Cacabelos, Ramón. "Donepezil in Alzheimer's disease: from conventional trials to pharmacogenetics." Neuropsychiatric disease and treatment 3.3 (2007): 303.
Cadieux, C. Linn, et al. "Probing the activity of a non-oxime reactivator for acetylcholinesterase inhibited by organophosphorus nerve agents." Chemico-biological interactions 259 (2016): 133-141.
Carletti, Eugénie, et al. "Structure-activity analysis of aging and reactivation of human butyrylcholinesterase inhibited by analogues of tabun." Biochemical Journal 421.1 (2009): 97-106.
Chi, Ki Whan, et al. "Synthesis of Mannich Bases Using Substituted Aromatic Alcohols with Secondary Amines: Relative Reactivity and Regioselectivity Depending on Substrates." Journal of the Korean Chemical Society 45.1 (2001): 51-60. English Abstract included in text.
Chi, Ki-Whan; Ahn, Yoon Soo; Shim, Kwang Taeg; Park, Tae Ho; Ahn, Jeong Soo From Bulletin of the Korean Chemical Society (1999), 20(8), 973-976.
Childs, A. F., et al. "The reactivation by oximes and hydroxamic acids of cholinesterase inhibited by organo-phosphorus compounds." British Journal of Pharmacology 10.4 (1955): 462-465.
Cummings, Jeffrey L., et al. "High-dose donepezil (23 mg/day) for the treatment of moderate and severe Alzheimer's disease: drug profile and clinical guidelines." CNS neuroscience & therapeutics 19.5 (2013): 294-301.

Delfino, Reinaldo T., Tatiana S. Ribeiro, and José D. Figueroa-Villar. "Organophosphorus compounds as chemical warfare agents: a review." Journal of the Brazilian Chemical Society 20.3 (2009): 407-428.
Eddleston, Michael, et al. "Management of acute organophosphorus pesticide poisoning." The Lancet 371.9612 (2008): 597-607.
Eddleston, Michael, et al. "Oximes in acute organophosphorus pesticide poisoning a systematic review of clinical trials." Qjm 95.5 (2002): 275-283.
Ellman, George L., et al. "A new and rapid colorimetric determination of acetylcholinesterase activity." Biochemical pharmacology 7.2 (1961): 88-95.
Eyer, P. (2003). The role of oximes in the management of organophosphorus pesticide poisoning. Toxicological reviews, 22(3), 165-190.
Franklin, M. C., Rudolph, M. J., Ginter, C., Cassidy, M. S., Cheung, J. (2016) "Structures of paraoxon-inhibited human acetylcholinesterase reveal perturbations of the acyl loop and the dimer interface" Proteins 84, 1246-1256.
Freccero, M. (2004) "Quinone methides as alkylating and cross-linking agents" Mini-Rev. Org. Chem. 1, 403-415.
Garrett, T. L., Rapp, C. M., Grubbs, R. D., Schlager, J. J., & Lucot, J. B. (2010). A murine model for sarin exposure using the carboxylesterase inhibitor CBDP. Neurotoxicology, 31(5), 502-508.
Golomb, B. A. (2008). Acetylcholinesterase inhibitors and Gulf War illnesses. Proceedings of the National Academy of Sciences, 105(11), 4295-4300.
Gorecki, L., Korabecny, J., Musilek, K., Malinak, D., Nepovimova, E., Dolezal, R., Jun, D., Soukup, O., Kuca,K. (2016) "SAR study to find optimal cholinesterase reactivator against organophosphorous nerve agents and pesticides" Arch. Toxicol. 90, 2831-2859.
Grove, S. J. A., Kaur, J., Muir, A. W., Pow, E., Traver, G. J., Zhang, M. Q. (2002) "Oxyaniliniums as acetylcholinesterase inhibitors for the reversal of neuromuscular block" Bioorg. Med. Chem. Lett. 12, 193-196.
Grube, A.; Donaldson, D.; Kiely, T.; Wu, L. US EPA Pesticides Industry Sales and Usage Report, 2007.
Harris, L. W., & Stitcher, D. L. (1983). Reactivation of VX-inhibited cholinesterase by 2-PAM and HS-6 in rats. Drug and chemical toxicology, 6(3), 235-240.
Heilbronn, E. (1965). Action of fluoride on cholinesterase—II: In vitro reactivation of cholinesterases inhibited by organophosphorous compounds. Biochemical pharmacology, 14(9), 1363-1373.
Jennings, L.L., Malecki, M., Komives, E.A., Taylor, P. (2003) "Direct analysis of the kinetic profiles of organophosphate-acetylcholinesterase adducts by MALDI-TOF mass spectrometry" Biochemistry 2003, 42, 11083-11091.
Jokanovic, M., & Prostran, M. (2009). Pyridinium oximes as cholinesterase reactivators. Structure-activity relationship and efficacy in the treatment of poisoning with organophosphorus compounds. Current medicinal chemistry, 16(17), 2177-2188.
Katz, Francine S., et al. "Discovery of new classes of compounds that reactivate acetylcholinesterase inhibited by organophosphates." Chembiochem: a European journal of chemical biology 16.15 (2015): 2205.
Khavrutskii, et al., "Beta-Aminoalcohols as potential reactivators of aged sarin-/soman-inhibited acetylcholinesterase.", Chemistry Select 2, 1885-1890 (2017).
Kryger, G., Harel, M., Giles, K., Toker, L., Velan, B., Lazar, A., Kronman, C., Barak, D., Ariel, N., Shafferman, A., Silman, I., Sussman, J. L. (2000) "Structures of recombinant native and E202Q mutant human acetylcholinesterase complexed with snake venom toxin fasciculin-II" Acta Crystallogr. D Biol. Crystallogr. 56(11), 1385-1394.
Kryger, G.; Silman, I.; Sussman, J. L. (1999) "Structure of acetylcholinesterase complexed with E2020 (Aricept): implications for the design of new anti-Alzheimer drugs" Structure 7, 297-307.
Lenz, D. E., Yeung, D., Smith, J. R., Sweeney, R. E., Lumley, L. A., Cerasoli, D. M. (2007) "Stoichiometric and catalytic scavengers as protection against nerve agent toxicity: A mini review" Toxicology 233, 31-39.
Li, H., Schopfer, L. M., Nachon, F., Froment, M. T., Masson, P., Lockridge, O. (2007) "Aging pathways for organophosphate-

(56) References Cited

OTHER PUBLICATIONS inhibited human butyrylcholinesterase, including novel pathways for isomalathion, resolved by mass spectrometry" Toxicol. Sci. 100, 136-145.

Lockridge, O., Blong, R. M., Masson, P., Froment, M. T., Millard, C. B., Broomfield, C. A. (1997) "A single amino acid substitution, Gly117His, confers phosphotriesterase (organophosphorus acid anhydride hydrolase) activity on human butyrylcholinesterase" Biochemistry 36, 786-795.

Lodge, A. M. "Kinetic evaluation of the inhibition and reactivation of human acetylcholinesterase" Ph.D. thesis, University of Iowa, 2013.

Marsais, F., et al. "Directed lithiation of 4-halopyridines: Chemoselectivity, regioselectivity and application to synthesis." Journal of heterocyclic chemistry 25.1 (1988): 81-87.

Marsillach, Judit, et al. "Biomarkers of organophosphorus (OP) exposures in humans." Neurotoxicology 32.5 (2011): 656-660.

Maxwell, D. M., Brecht, K. M., & O'Neill, B. L. (1987). The effect of carboxylesterase inhibition on interspecies differences in soman toxicity. Toxicology letters, 39(1), 35-42.

Mazur, Abraham, and Oscar Bodansky. "The mechanism of in vitro and in vivo inhibition of cholinesterase activity by diisopropyl fluorophosphate." Journal of Biological Chemistry 163.1 (1946): 261-276.

McElroy, C., McGarry, K., Wilhelm, C., Bartlett, R., Read, D. (2012) "Acetylcholinesterase Specific Activity in Blood and Tissues from Multiple Species" 18th Biennial Medical Defense Bioscience Review, Hunt Valley MD.

McGarry, K. G.; Bartlett, R. A.; Machesky, N. J.; Snider, T. H.; Moyer, R. A. Yeung, D. T.; Brittain, M. K. (2013) "Evaluation of HemogloBind™ treatment for preparation of samples for cholinesterase analysis" Adv. Biosci.Biotechnol. 4, 1020-1023.

Mercey, G., Renou, J., Verdelet, T., Kliachyna, M., Baati, R., Gillon, E., . . . & Renard, P. Y. (2012). Phenyltetrahydroisoquinoline-pyridinaldoxime conjugates as efficient uncharged reactivators for the dephosphylation of inhibited human acetylcholinesterase. Journal of Medicinal Chemistry, 55(23), 10791-10795.

Millard, C. B., Kryger, G., Ordentlich, A., Greenblatt, H. M., Harel, M., Raves, M. L., . . . & Sussman, J. L. (1999). Crystal structures of aged phosphonylated acetylcholinesterase: nerve agent reaction products at the atomic level. Biochemistry, 38(22), 7032-7039.

Nachon, F., Asojo, O. A., Borgstahl, G. E., Masson, P., & Lockridge, O. (2005). Role of water in aging of human butyrylcholinesterase inhibited by echothiophate the crystal structure suggests two alternative mechanisms of aging. Biochemistry, 44(4), 1154-1162.

Pastan, I., Gottesman, M. M., Ueda, K., Lovelace, E., Rutherford, A. V., & Willingham, M. C. (1988). A retrovirus carrying an MDR1 cDNA confers multidrug resistance and polarized expression of P-glycoprotein in MDCK cells. Proceedings of the National Academy of Sciences, 85(12), 4486-4490.

Pope, C., Karanth, S., & Liu, J. (2005). Pharmacology and toxicology of cholinesterase inhibitors: uses and misuses of a common mechanism of action. Environmental Toxicology and Pharmacology, 19(3), 433-446.

Ravelli, R. B., Raves, M. L., Ren, Z., Bourgeois, D., Roth, M., Kroon, J., . . . & Sussman, J. L. (1998). Static Laue diffraction studies on acetylcholinesterase. Acta Crystallographica Section D: Biological Crystallography, 54(6), 1359-1366.

Renou, J., Dias, J., Mercey, G., Verdelet, T., Rousseau, C., Gastellier, A. J., . . . & Nachon, F. (2016). Synthesis and in vitro evaluation of donepezil-based reactivators and analogues for nerve agent-inhibited human acetylcholinesterase. RSC Advances, 6(22), 17929-17940.

Sanson, B., Nachon, F., Colletier, J. P., Froment, M. T., Toker, L., Greenblatt, H. M., . . . & Weik, M. (2009). Crystallographic snapshots of nonaged and aged conjugates of soman with acetylcholinesterase, and of a ternary complex of the aged conjugate with pralidoxime. Journal of medicinal chemistry, 52(23), 7593-7603.

Sawatzky, E., Wehle, S., Kling, B., Wendrich, J., Bringmann, G., Sotriffer, C. A., . . . & Decker, M. (2016). Discovery of highly selective and nanomolar carbamate-based butyrylcholinesterase inhibitors by rational investigation into their inhibition mode. Journal of medicinal chemistry, 59(5), 2067-2082.

Saxena, J.; Meloni, D.; Huang, M. T.; Heck, D. E.; Laskin, J. D.; Heindel, N. D. Young, S. C. (2015) "Ethynylphenyl carbonates and carbamates as dual-action acetylcholinesterase inhibitors and anti-inflammatory agents" Bioorg. Med. Chem. Lett. 25, 5609-5612.

Shafferman, Avigdor, et al. "Aging of phosphylated human acetylcholinesterase catalytic processes mediated by aromatic and polar residues of the active centre," Biochemical Journal 318.3 (1996): 833-840.

Shutt, L. E., & Bowes, J. B. (1979). "Atropine and hyoscine". Anaesthesia, 34(5), 476-490.

Sun, M., Chang, Z., Shau, M., Huang, R.; Chou, T. (1979) "The mechanism of ageing of phosphonylated acetylcholinesterase" Eur. J. Biochem., 100, 527-530.

Topczewski, J. J., & Quinn, D. M. (2013). Kinetic assessment of N-methyl-2-methoxypyridinium species as phosphonate anion methylating agents. Organic letters, 15(5), 1084-1087.

Wandhammer, M., de Koning, M., van Grol, M., Loiodice, M., Saurel, L., Noort, D., Goeldner, M., Nachon, F. (2013) "A step toward the reactivation of aged cholinesterases—Crystal structure of ligands binding to aged human butyrylcholinesterase" Chemico-Biol. Interact. 203, 19-23.

Weinert, E. E., Dondi, R., Colloredo-Melz, S., Frankenfield, K. N., Mitchell, C. H., Freccero, M., & Rokita, S. E. (2006). Substituents on quinone methides strongly modulate formation and stability of their nucleophilic adducts. Journal of the American Chemical Society, 128(36), 11940-11947.

Yoder, R. J., Zhuang, Q., Beck, J. M., Franjesevic, A., Blanton, T. G., Sillart, S., . . . & McElroy, C. A. (2017). Study of para-Quinone Methide Precursors toward the Realkylation of Aged Acetylcholinesterase. ACS medicinal chemistry letters, 8(6), 622-627.

Zhou, Q., & Rokita, S. E. (2003). A general strategy for target-promoted alkylation in biological systems. Proceedings of the National Academy of Sciences, 100(26), 15452-15457.

Zhuang, Q., Young, A., Callam, C. S., McElroy, C. A., Ekici, Ö. D., Yoder, R. J., & Hadad, C. M. (2016). Efforts toward treatments against aging of organophosphorus-inhibited acetylcholinesterase. Annals of the New York Academy of Sciences, 1374(1), 94-104.

\* cited by examiner

HETEROAROMATIC ELECTROPHILES AND METHODS OF USING THEREOF

CROSS-REFERENCE TO RELATED APPLICATIONS

This application is a national stage application filed under 35 U.S.C. § 371 of PCT/US2018/018374 filed Feb. 15, 2018, which claims benefit of U.S. Provisional Application No. 62/459,385, filed Feb. 15, 2017, which is hereby incorporated herein by reference in its entirety.

STATEMENT REGARDING FEDERALLY SPONSORED RESEARCH OR DEVELOPMENT

This invention was made with government support under Grant No. 1U01-NS087983 awarded by the National Institutes of Health. The government has certain rights in the invention.

BACKGROUND OF THE DISCLOSURE

Acetylcholinesterase (AChE) is a serine hydrolase that is responsible for the hydrolysis of the neurotransmitter acetylcholine (ACh). Upon inhibition of AChE by an organophosphorus (OP) pesticide or chemical warfare agent, ACh begins to accumulate, triggering uncontrolled nerve impulses, which leads to the undesired effects of blurred vision, seizures, respiratory failure, and ultimately death.

Mechanistically, inhibition of AChE by an OP begins in a fashion analogous to the hydrolysis of the enzyme's natural substrate, ACh. OP compounds readily enter the active site of AChE, where the nucleophilic serine residue of the catalytic triad forms a covalent bond with the electrophilic phosphorus, and in turn displaces a leaving group from the OP. However, this is where the similarities between ACh substrate turnover and OP inhibition end. Unlike the enzymatic hydrolysis of ACh, for which the acylated serine is rapidly hydrolyzed by a water molecule to produce acetate, thereby regenerating the active enzyme, the spontaneous hydrolysis of the inhibited, OP-phosphylated enzyme occurs on a significantly slower time scale (with rates dependent on the specific OP), leading to the accumulation of ACh, and the undesired associated effects.

A significant amount of research has been devoted to developing drug-like molecules that are capable of reversing this inhibition. It has been shown that charged oximes, such as 2-PAM, are capable of regenerating active AChE through a phosphyl transfer reaction between the nucleophilic oximate and the phosphylated serine in the active site of the aged enzyme. However, the level of complexity of OP inhibition is taken a step further by a secondary process known as "aging". Aging occurs by the spontaneous dealkylation of an O—R group bound to the phosphorus center of the OP-inhibited AChE. Aging is problematic, as after this process occurs, oximes are no longer an effective treatment method, and to date there have been no successful reports of resurrecting aged AChE to regain the desired and native catalytic function for AChE.

Some attempts towards realkylation of aged AChE have been reported with limited success. Early work in the area of developing realkylating reagents by Blumberg and co-workers in 1969 described the synthesis of a series of alkylsulfonate alkylators incorporating a quaternary nitrogen or pyridinium group to assist with aqueous solubility and affinity for the AChE active site. (P. Blumbergs, et al., *J Org Chem* 34, 4065-4070 (1969)). While alkylation of various nucleophiles proceeded in solution, alkylation of isopropyl methyl phosphonate as a model system for aged AChE was slow, and realkylation of authentic aged AChE (as an in vitro experiment) has not been reported.

Shortly thereafter, Steinberg and co-workers developed a unique family of phenylacyl bromide alkylators that could react with a model phosphonate anion. (G. M. Steinberg, et al., *J Med Chem* 13, 435-446 (1970)). Following realkylation by Steinberg's compounds, hydrolysis leading to departure of the p-nitrophenol was explored. Steinberg hypothesized that intramolecular coordination of the carbonyl incorporated in their alkylators would enhance the rate of hydrolysis of the p-nitrophenol group. Unfortunately, with these realkylating compounds, no in vitro alkylation of aged AChE was observed by Steinberg and co-workers.

More recently, the Quinn group reported the methylation of a methyl methanephosphonate anion as an aqueous model for the aged AChE-OP adduct using N-methyl-2-methoxypyridinium methyl transfer reagents. While successful alkylation of a phosphonate model system was observed (40% alkylation in less than 10 min for 3-fluoro-N-methyl-2-methoxypyridinium), none of the alkylators tested showed any ability to resurrect in vitro aged AChE in preliminary studies.

There is a need for compounds and methods that are capable of reversing AChE inhibition as well as the aging process.

SUMMARY OF THE DISCLOSURE

Disclosed herein are compounds, compositions, and methods for reactivating and/or realkylating aged acetylcholinesterase. In some instances, the acetylcholinesterase can be in the central nerve system (CNS) and/or the peripheral nervous system (PNS). Accordingly, methods for ameliorating, diminishing, reversing, treating or preventing the toxic effects of an organophosphorus compound in a subject are provided herein. Methods for prophylactic or therapeutic treatment of exposure to an organophosphorus nerve agent are also provided.

The methods disclosed herein can include administering a composition comprising a prophylactically or therapeutically effective amount of a compound having a structure represented below. The compound can be administered in combination with a second compound that reverses inhibition of acetylcholinesterase by the organophosphorus compound. In some embodiments, the second compound does not cross the blood brain barrier. The compositions disclosed herein can be administered enterally or parenterally.

The compounds disclosed herein can have a structure represented by Formula I:

Formula I

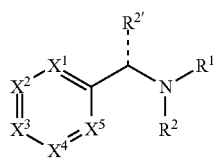

wherein $X^1$-$X^5$ are independently selected from N, NR', and CR',

R' is, independently for each occurrence, selected from hydrogen, $C_1$-$C_6$ alkyl, $C_1$-$C_6$ alkyl halide, $C_1$-$C_6$ alkoxy, hydroxyl, halogen, amine, alkylamine, alkylammonium, or where two R' groups combine to form a substituted or unsubstituted fused $C_5$-$C_7$ cyclic moiety;

$R^1$ and $R^2$ are independently selected from $C_1$-$C_6$ alkyl, $C_1$-$C_6$ alkyl halide, $C_1$-$C_6$ alkoxy, or $R^1$ and $R^2$ combine to form a 3 to 7 membered aliphatic ring, and wherein $R^1$ and $R^2$ are optionally substituted with alkyl, heteroalkyl, cycloalkyl, cycloheteroalkyl, aryl, heteroaryl, alkyl halide, halogen, alkoxy, amine, alkylamine, and alkylammonium; and $R^{2'}$ is optionally present and selected from $C_1$-$C_6$ alkyl, $C_1$-$C_6$ alkyl halide, $C_1$-$C_6$ alkoxy, and $C_1$-$C_6$ alkyl amine, or $R^1$ and $R^{2'}$ or $R^2$ and $R^{2'}$ combine to form a 5 to 7 membered aliphatic ring; and wherein at least one of $X^1$-$X^5$ is N or NR', and at least one of $X^1$-$X^5$ is C—OH.

In some embodiments of Formula I, the compound can be represented by a structure having the Formula II-A to II-G:

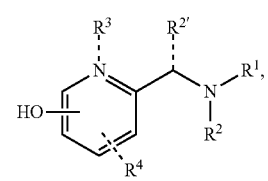

Formula II-A

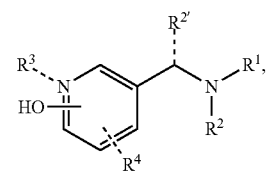

Formula II-B

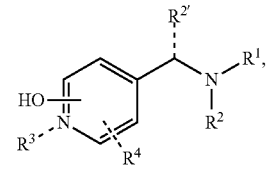

Formula II-C

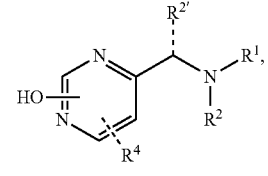

Formula II-D

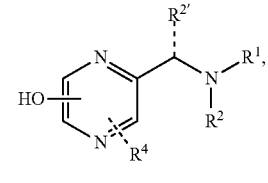

Formula II-E

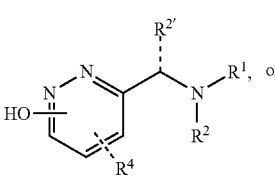

Formula II-F

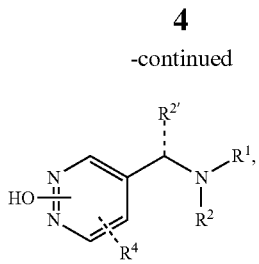

Formula II-G wherein $R^3$ is selected from hydrogen, $C_1$-$C_6$ alkyl, $C_1$-$C_6$ alkyl halide, $C_1$-$C_6$ alkoxy, alkylamine;

$R^4$ is selected from $C_1$-$C_6$ alkyl, halogen, $C_1$-$C_6$ alkyl halide, $C_1$-$C_6$ alkoxy, nitrile, amine, alkylamine, and alkylammonium; and wherein $R^{2'}$, $R^3$ and $R^4$ are optionally present.

In other embodiments of Formula I, the compound can be represented by a structure having the Formula II-H to II-Q:

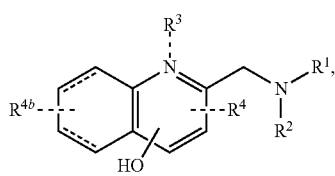

Formula II-H

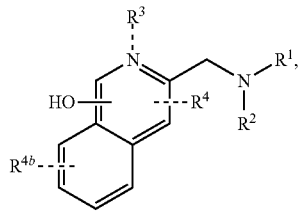

Formula II-I

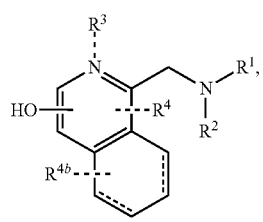

Formula II-J

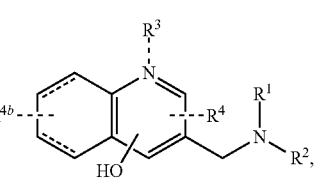

Formula II-K

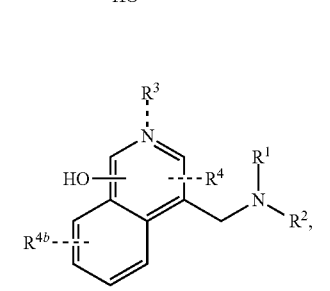

Formula II-L

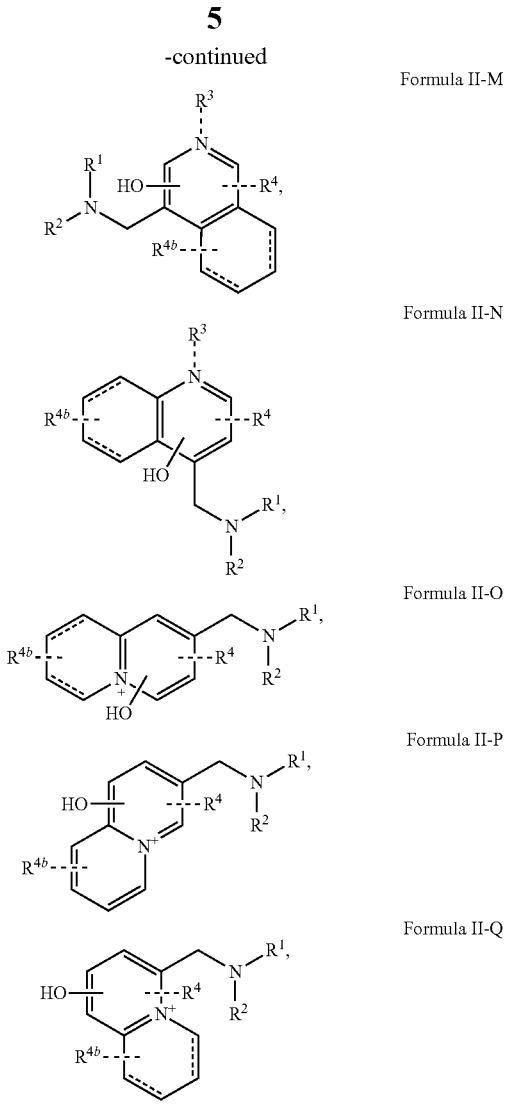

Formula II-M

Formula II-N

Formula II-O

Formula II-P

Formula II-Q wherein $R^3$, $R^4$, and $R^{4b}$ are optionally present, and wherein $R^{4b}$ when present is selected from $C_1$-$C_6$ alkyl, halogen, $C_1$-$C_6$ alkyl halide, $C_1$-$C_6$ alkoxy, nitrile, amine, alkylamine, and alkylammonium.

Pharmaceutical compositions or formulations comprising a compound represented by a structure described herein and a pharmaceutically acceptable excipient are also disclosed.

BRIEF DESCRIPTION OF THE DRAWINGS

FIG. 1A shows general structures of quinone methides (QMs; top) and quinone methide precursors (QMPs; bottom). FIG. 1B shows a nucleophile can substitute the leaving group of QMP by either an $S_N2$ reaction or formation of the corresponding QM. FIG. 1C shows structures of PiMP, DFP, and their aged AChE adducts.

FIG. 3A shows structures of QMPs. FIG. 3B shows screening of the C series QMPs against methylphosphonate-aged eeAChE and FIG. 3C against isopropyl phosphate-aged eeAChE. The horizontal dotted and the dashed lines mark the negative controls and 2-PAM controls, respectively. The error bars reflect standard deviations from four replicate efforts.

FIG. 5A shows $^1$H NMR spectra of the aromatic protons and FIG. 5B shows UV-vis spectra of C8 as pH is varied from 6~9. FIG. 5C shows the four most probable protonation states of C8 at pH 8-9. FIG. 5D shows a representative snapshot in the MD simulation of $C_8c$ (wall-eyed stereo). Hydrogen bonds with short contact distances are shown (dashed lines).

DETAILED DESCRIPTION

Definitions

Figures 1A, 1B, 1C:
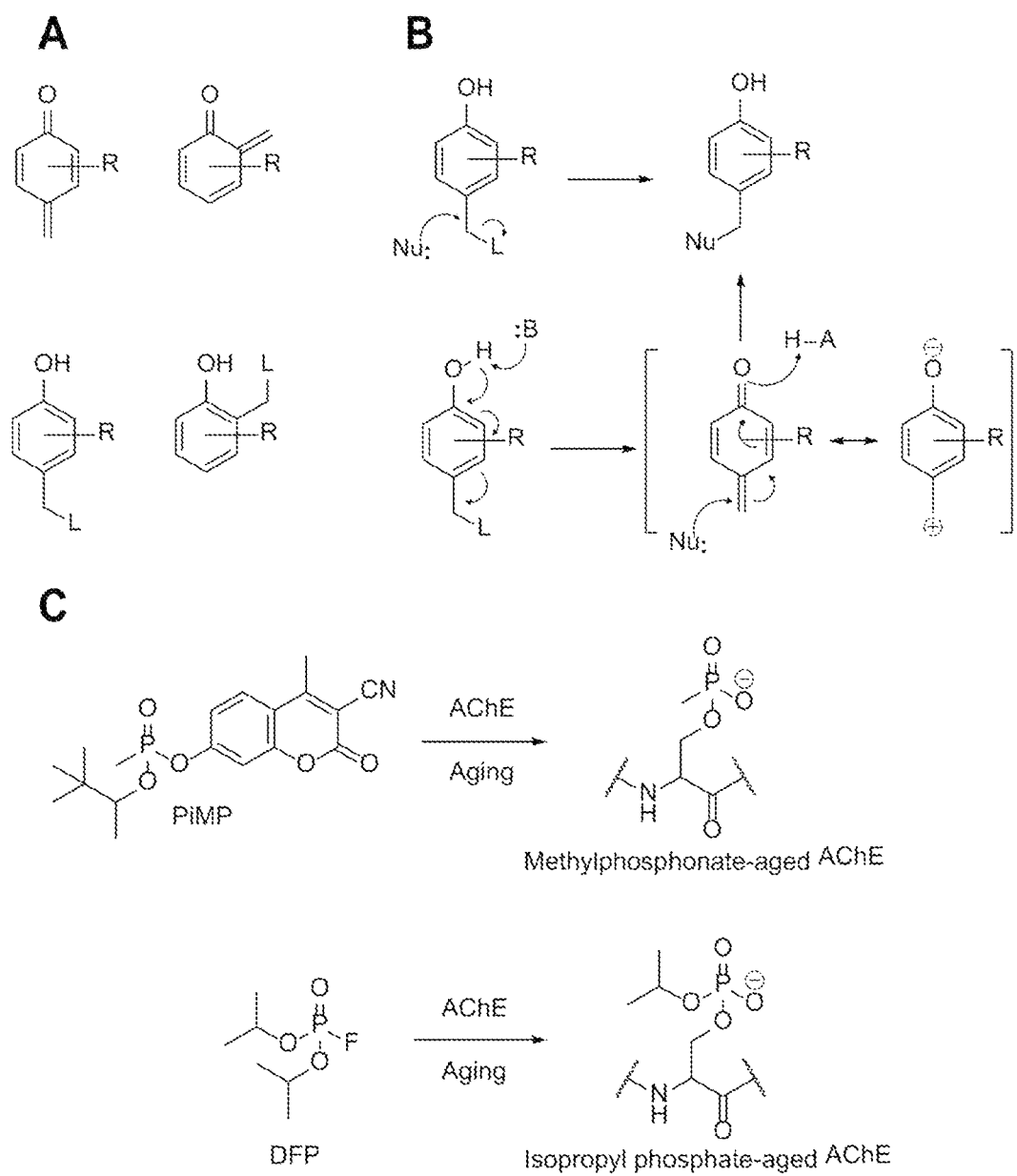
FIG. 1A-1C.

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix $C_n$-$C_m$ indicates in each case the possible number of carbon atoms in the group.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic. It is understood that this is typically in relation to some standard or expected value, in other words it is relative, but that it is not always necessary for the standard or relative value to be referred to. For example, "reducing the toxic effects of an organophosphorus compound" can refer to reducing the rate of inhibition of the enzyme acetylcholinesterase relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., a biofilm). The term "control" is used synonymously with the terms "treat" and "modulate."

An "effective amount" of a compound or composition disclosed herein is that amount which is necessary to carry out the compound's or composition's function of ameliorating, diminishing, reversing, treating or preventing the toxic effects of an organophosphorus compound in a subject.

The term "alkyl," as used herein, refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$, $C_1$-$C_5$, $C_1$-$C_4$, $C_1$-$C_3$, $C_1$-$C_2$, or $C_1$ alkyl groups. Examples of $C_1$-$C_{10}$ alkyl groups include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl groups, as well as their isomers. Examples of $C_1$-$C_4$-alkyl groups include, for example, methyl, ethyl, propyl, 1-methylethyl, butyl, 1-methylpropyl, 2-methylpropyl and 1,1-dimethylethyl groups.

Cyclic alkyl groups or "cycloalkyl" groups, which are encompassed alkyl, include cycloalkyl groups having from 3 to 10 carbon atoms. Cycloalkyl groups can include a single ring, or multiple condensed rings. In some embodiments, cycloalkyl groups include $C_3$-$C_4$, $C_4$-$C_7$, $C_5$-$C_7$, $C_4$-$C_6$, or $C_5$-$C_6$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

Alkyl groups can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrazine, carbamate, phosphoric acid, phosphate, phosphonate, or any other viable functional group that does not inhibit the biological activity of the compounds of the invention, either unprotected, or protected as necessary, as known to those skilled in the art, for example, as described in Greene, et al., *Protective Groups in Organic Synthesis*, John Wiley and Sons, Third Edition, 1999, hereby incorporated by reference.

Terms including the term "alkyl," such as "alkylcycloalkyl," "cycloalkylalkyl," "alkylamino," or "dialkylamino," will be understood to comprise an alkyl group as defined above linked to another functional group, where the group is linked to the compound through the last group listed, as understood by those of skill in the art.

The term "alkenyl," as used herein, refers to both straight and branched carbon chains which have at least one carbon-carbon double bond. In some embodiments, alkenyl groups can include $C_2$-$C_{20}$ alkenyl groups. In other embodiments, alkenyl can include $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. The one or more unsaturations within the alkenyl group may be located at any position(s) within the carbon chain as valence permits. In some embodiments, when the alkenyl group is covalently bound to one or more additional moieties, the carbon atom(s) in the alkenyl group that are covalently bound to the one or more additional moieties are not part of a carbon-carbon double bond within the alkenyl group. Examples of alkenyl groups include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl groups.

The term "alkynyl," as used herein, refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl, and 4-methylpent-2-yn-5-yl groups.

The term "haloalkyl" or "alkylhalide," as used herein refers to an alkyl group, as defined above, which is substituted by one or more halogen atoms. In some instances, the haloalkyl group can be an alkyl group substituted by one or more fluorine atoms. In certain instances, the haloalkyl group can be a perfluorinated alkyl group. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, and pentafluoroethyl.

The term "alkoxy," as used herein, refers to alkyl-O—, wherein alkyl refers to an alkyl group, as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, and 1-ethyl-2-methylpropoxy.

The terms "alkylamino" and "dialkylamino," as used herein, refer to alkyl-NH— and $(alkyl)_2N$— groups, where alkyl is as defined above. Similarly, the terms "haloalkylamino" and "halodialkylamino" refer to haloalkyl-NH— and $(haloalkyl)_2$-NH—, where haloalkyl is as defined above.

The term "aryl," as used herein, refers to a monovalent aromatic carbocyclic group of from 6 to 14 carbon atoms. Aryl groups can include a single ring or multiple condensed rings. In some embodiments, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynylsulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl) amino, di(alkenyl)-amino, di(alkynyl)amino, or trialkylsilyl.

The term "alkylaryl," as used herein, refers to an aryl group that is bonded to a parent compound through a diradical alkylene bridge, $(—CH_2—)_n$, where n is 1-12 and where "aryl" is as defined above.

The term "alkylcycloalkyl," as used herein, refers to a cycloalkyl group that is bonded to a parent compound through a diradical alkylene bridge, $(—CH_2—)_n$, where n is 1-12 and where "cycloalkyl" is as defined above. The term "cycloalkylalkyl," as used herein, refers to a cycloalkyl group, as defined above, which is substituted by an alkyl group, as defined above.

The term "heteroaryl," as used herein, refers to a monovalent aromatic group of from 1 to 15 carbon atoms (e.g., from 1 to 10 carbon atoms, from 2 to 8 carbon atoms, from 3 to 6 carbon atoms, or from 4 to 6 carbon atoms) having one or more heteroatoms within the ring. The heteroaryl group can include from 1 to 4 heteroatoms, from 1 to 3 heteroatoms, or from 1 to 2 heteroatoms. In some cases, the heteroatom(s) incorporated into the ring are oxygen, nitrogen, sulfur, or combinations thereof. When present, the nitrogen and sulfur heteroatoms may optionally be oxidized. Heteroaryl groups can have a single ring (e.g., pyridyl or furyl) or multiple condensed rings provided that the point of attachment is through a heteroaryl ring atom. Preferred heteroaryls include pyridyl, pyridazinyl, pyrimidinyl, pyrazinyl, triazinyl, pyrrolyl, indolyl, quinolinyl, isoquinolinyl, quinazolinyl, quinoxalinyl, furanyl, thiophenyl, furyl, pyrrolyl, imidazolyl, oxazolyl, isoxazolyl, isothiazolyl, pyrazolyl, benzofuranyl, and benzothiophenyl. Heteroaryl rings may be unsubstituted or substituted by one or more moieties as described for aryl above.

The term "alkylheteroaryl," as used herein, refers to a heteroaryl group that is bonded to a parent compound through a diradical alkylene bridge, $(—CH_2—)_n$, where n is 1-12 and where "heteroaryl" is as defined above.

The terms "cycloheteroalkyl," "heterocyclyl," "heterocyclic," and "heterocyclo" are used herein interchangeably, and refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, having one or more heteroatoms within the ring. The heterocyclyl group can include from 1 to 4 heteroatoms, from 1 to 3 heteroatoms, or from 1 to 2 heteroatoms. In some cases, the heteroatom(s) incorporated into the ring are oxygen, nitrogen, sulfur, or combinations thereof. When present, the nitrogen and sulfur heteroatoms may optionally be oxidized, and the nitrogen heteroatoms may optionally be quaternized. The heterocyclyl group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

The term "alkylheterocyclyl" and "alkylcycloheteroalkyl" are used herein interchangeably, and refer to a heterocyclyl group that is bonded to a parent compound through a diradical alkylene bridge, $(—CH_2—)_n$, where n is 1-12 and where "heterocyclyl" is as defined above. The term "heterocyclylalkyl," as used herein, refers to a heterocyclyl group, as defined above, which is substituted by an alkyl group, as defined above.

The term "halogen," as used herein, refers to the atoms fluorine, chlorine, bromine and iodine. The prefix halo- (e.g., as illustrated by the term haloalkyl) refers to all degrees of halogen substitution, from a single substitution to a perhalo substitution (e.g., as illustrated with methyl as chloromethyl (—$CH_2Cl$), dichloromethyl (—$CHCl_2$), trichloromethyl (—$CCl_3$)).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

Compounds

Provided herein are pyridine and pyridinium electrophiles for reactivation and/or realkylating of acetylcholinesterase inhibited by or conjugated to an organophosphorus compound. In some aspects, the compound can have a structure represented by Formula I:

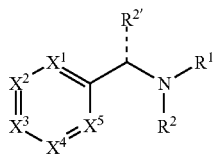

Formula I wherein $X^1$-$X^5$ are independently selected from N, NR', and CR',

R' is, independently for each occurrence, selected from hydrogen, $C_1$-$C_6$ alkyl, $C_1$-$C_6$ alkyl halide, $C_1$-$C_6$ alkoxy, hydroxyl, halogen, amine, alkylamine, alkylammonium, or where two R' groups combine to form a substituted or unsubstituted fused $C_5$-$C_7$ cyclic moiety;

$R^1$ and $R^2$ are independently selected from $C_1$-$C_6$ alkyl, $C_1$-$C_6$ alkyl halide, $C_1$-$C_6$ alkoxy, or $R^1$ and $R^2$ combine to form a 3 to 7 membered aliphatic ring, and wherein $R^1$ and $R^2$ are optionally substituted with alkyl, heteroalkyl, cycloalkyl, cycloheteroalkyl, aryl, heteroaryl, alkyl halide, halogen, alkoxy, amine, alkylamine, and alkylammonium; and $R^{2'}$ is optionally present and selected from $C_1$-$C_6$ alkyl, $C_1$-$C_6$ alkyl halide, $C_1$-$C_6$ alkoxy, and $C_1$-$C_6$ alkyl amine, or $R^1$ and $R^{2'}$ or $R^2$ and $R^{2'}$ combine to form a 5 to 7 membered aliphatic ring; and wherein at least one of $X^1$-$X^5$ is N or NR', and at least one of $X^1$-$X^5$ is C—OH For example, in certain embodiments of Formula I, $R^1$ and $R^2$ can be independently selected from methyl, ethyl, propyl, isopropyl, butyl, isobutyl. In other embodiments of Formula I, $R^1$ and $R^2$ can combine to form a monocyclic heterocyclic group, a bicyclic heterocyclic group, or a tricyclic heterocyclic group. In certain embodiments of Formula I, $R^1$ and $R^2$ can combine to form a substituted or unsubstituted pyrrolidine, substituted or unsubstituted piperidine, substituted or unsubstituted piperazine, substituted or unsubstituted morpholine, wherein the substituent can be selected from $C_1$-$C_6$ alkyl, $C_1$-$C_6$ alkyl halide, $C_1$-$C_6$ alkoxy, hydroxyl, halogen, amine, alkylamine, and alkylammonium.

In certain embodiments of Formula I, $R^{2'}$ is present and represents a $C_1$-$C_4$ alkyl group. In certain embodiments of Formula I, $R^{2'}$ is absent. In certain embodiments of Formula I, $R^1$ and $R^{2'}$ or $R^2$ and $R^{2'}$ combine to form a 5 to 7 membered aliphatic ring.

In some aspects, the compounds disclosed herein can have a structure represented by Formula II:

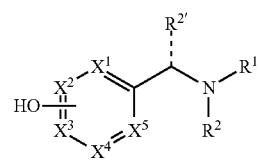

Formula II wherein $X^1$-$X^5$ are independently selected from N, NR', and CR',

R' is, independently for each occurrence, selected from hydrogen, $C_1$-$C_6$ alkyl, $C_1$-$C_6$ alkyl halide, $C_1$-$C_6$ alkoxy, hydroxyl, halogen, amine, alkylamine, alkylammonium, or where two R' groups combine to form a substituted or unsubstituted fused $C_5$-$C_7$ cyclic moiety;

$R^1$ and $R^2$ are independently selected from $C_1$-$C_6$ alkyl, $C_1$-$C_6$ alkyl halide, $C_1$-$C_6$ alkoxy, or $R^1$ and $R^2$ combine to form a 3 to 7 membered aliphatic ring, and wherein $R^1$ and $R^2$ are optionally substituted with alkyl, heteroalkyl, cycloalkyl, cycloheteroalkyl, aryl, heteroaryl, alkyl halide, halogen, alkoxy, amine, alkylamine, and alkylammonium; and $R^{2'}$ is optionally present and selected from $C_1$-$C_6$ alkyl, $C_1$-$C_6$ alkyl halide, $C_1$-$C_6$ alkoxy, and $C_1$-$C_6$ alkyl amine, or $R^1$ and $R^{2'}$ or $R^2$ and $R^{2'}$ combine to form a 5 to 7 membered aliphatic ring; and wherein at least one of $X^1$-$X^5$ is N or NR', and at least one of $X^1$-$X^5$ is C—OH In certain embodiments of Formula II, $R^1$ and $R^2$ can combine to form a monocyclic heterocyclic group, a bicyclic heterocyclic group, or a tricyclic heterocyclic group. In certain embodiments of Formula II, $R^1$ and $R^2$ can combine to form a substituted or unsubstituted pyrrolidine, substituted or unsubstituted piperidine, substituted or unsubstituted piperazine, substituted or unsubstituted morpholine, wherein the substituent can be selected from $C_1$-$C_6$ alkyl, $C_1$-$C_6$ alkyl halide, $C_1$-$C_6$ alkoxy, hydroxyl, halogen, amine, alkylamine, and alkylammonium.

In certain embodiments of Formula II, the compound can be represented by a structure having the Formula II-A to II-G:

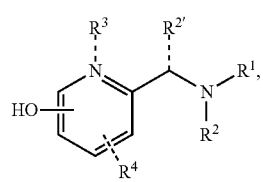

Formula II-A

-continued

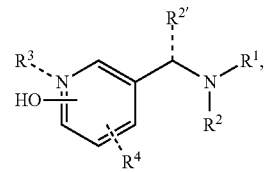
Formula II-B

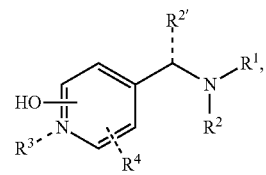
Formula II-C

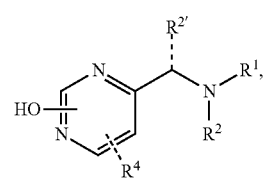
Formula II-D

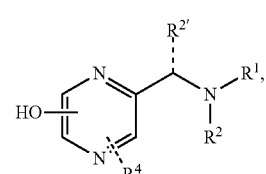
Formula II-E

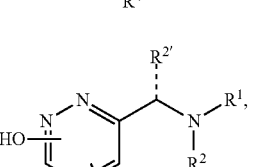
Formula II-F

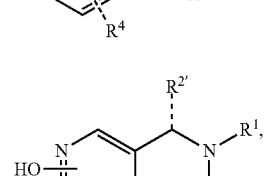

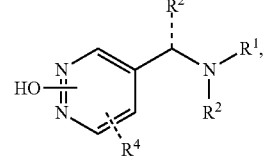
Formula II-G wherein $R^3$ is selected from hydrogen, $C_1$-$C_6$ alkyl, $C_1$-$C_6$ alkyl halide, $C_1$-$C_6$ alkoxy, alkylamine;

$R^4$ is selected from $C_1$-$C_6$ alkyl, halogen, $C_1$-$C_6$ alkyl halide, $C_1$-$C_6$ alkoxy, nitrile, amine, alkylamine, and alkylammonium; and wherein $R^{2'}$, $R^3$ and $R^4$ are optionally present.

In some examples, $R^3$ is absent. In other examples, $R^3$ is present. In some examples, $R^4$ is absent. In other examples, $R^4$ is present. In still other examples, more than one $R^4$ are present. When present, $R^3$ and $R^4$ can be independently selected from hydrogen, $C_1$-$C_6$ alkyl, halogen, $C_1$-$C_6$ alkyl halide, $C_1$-$C_6$alkoxy, nitrile, amine, alkylamine, alkylammonium, or an acetylcholinesterase inhibitor.

In certain embodiments of Formula II-A, the compounds disclosed herein can be represented by a structure having the Formula II-A-1:

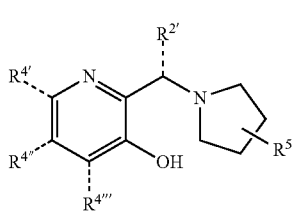
Formula II-A-1 wherein $R^{4'}$, $R^{4''}$, $R^{4'''}$, and $R^5$ are independently selected from $C_1$-$C_6$ alkyl, halogen, $C_1$-$C_6$ alkyl halide, $C_1$-$C_6$ alkoxy, nitrile, amine, alkylamine, and alkylammonium. Each of $R^{4'}$, $R^{4''}$, and $R^{4'''}$ can be independently absent or present. In certain embodiments of Formula II-A-1, $R^{4'}$, $R^{4''}$, $R^{4'''}$, and $R^5$ are independently selected from hydrogen, $C_1$-$C_6$ alkyl, halogen, $C_1$-$C_6$ alkyl halide, $C_1$-$C_6$ alkoxy, nitrile, amine, or an acetylcholinesterase inhibitor.

In certain embodiments of Formula II-A-1, the compounds disclosed herein can be represented by a structure having the Formula II-A-1':

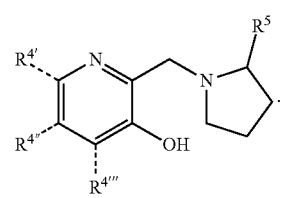
Formula II-A-1'

In certain embodiments of Formula II-A, the compounds disclosed herein can be represented by a structure having the Formula II-A-2:

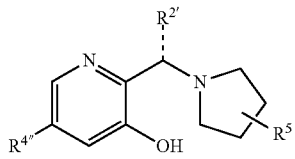
Formula II-A-2 wherein $R^{4''}$ and $R^5$ are independently selected from $C_1$-$C_6$ alkyl, halogen, $C_1$-$C_6$ alkyl halide, $C_1$-$C_6$ alkoxy, nitrile, amine, alkylamine, and alkylammonium. For example, $R^5$ can be selected from hydrogen, $C_1$-$C_6$ alkyl, halogen, $C_1$-$C_6$ alkyl halide, $C_1$-$C_6$ alkoxy, nitrile, amine, alkylamine, or alkylammonium and $R^{4''}$ can be an acetylcholinesterase inhibitor.

In certain examples of Formula I or II, the compound can be selected from:

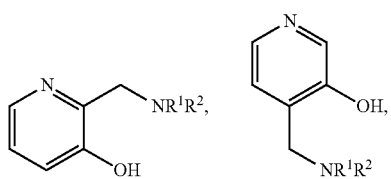

-continued
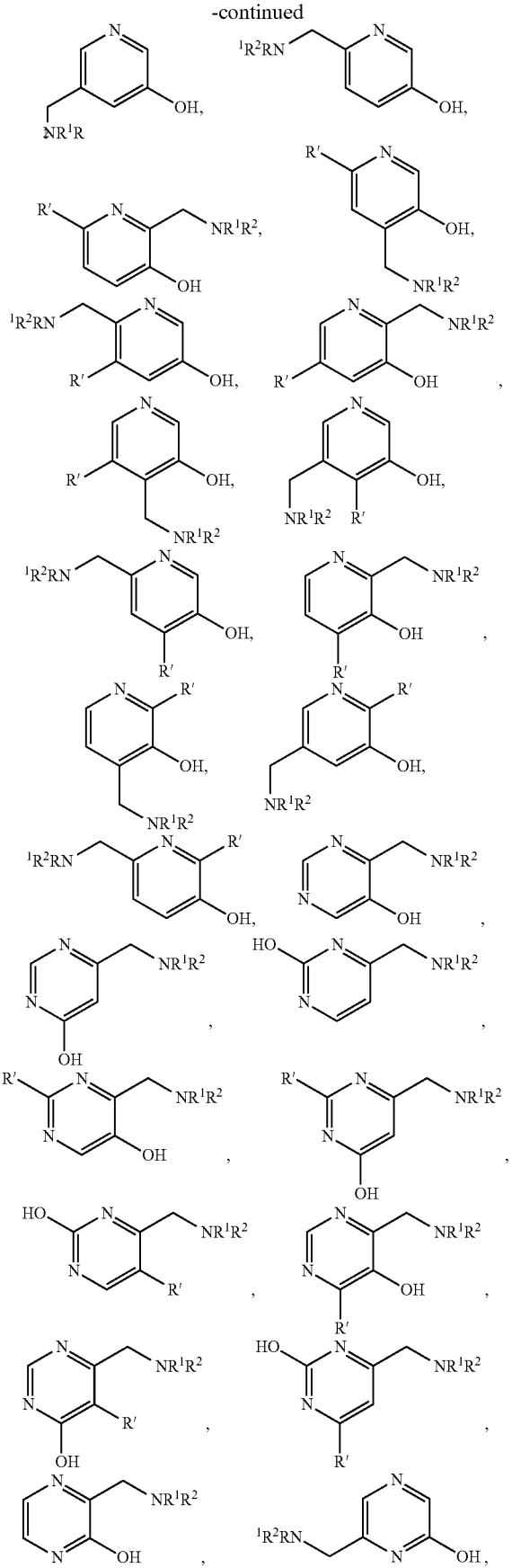
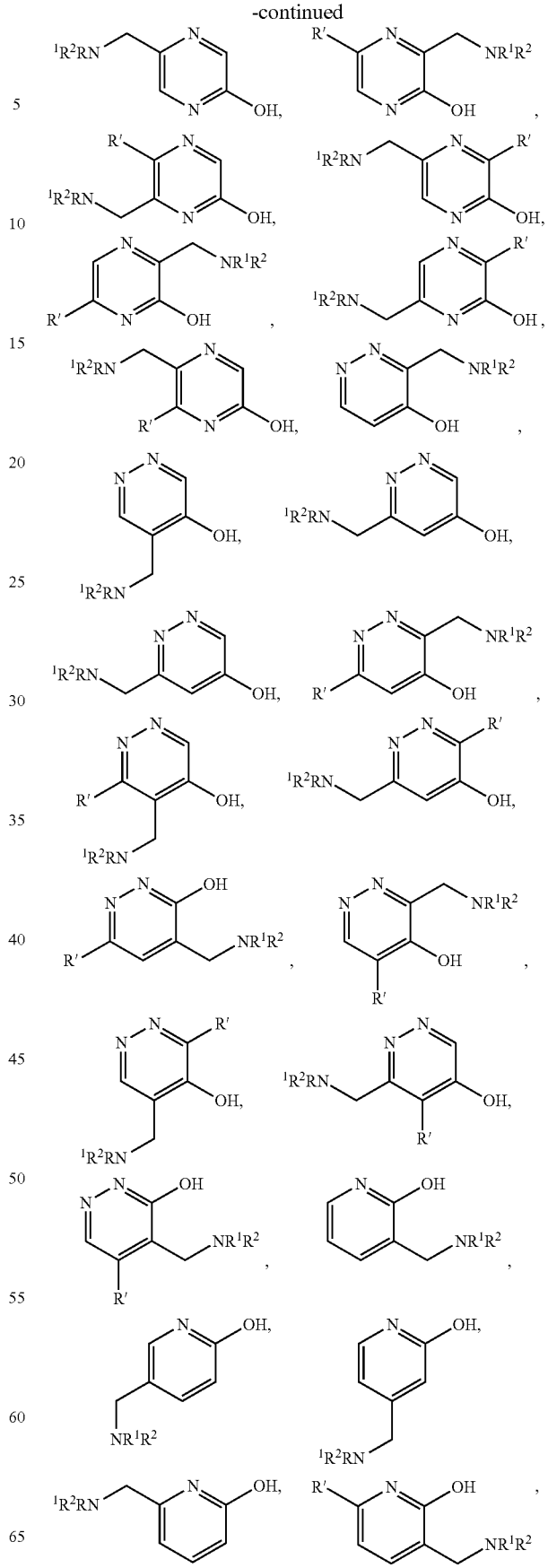

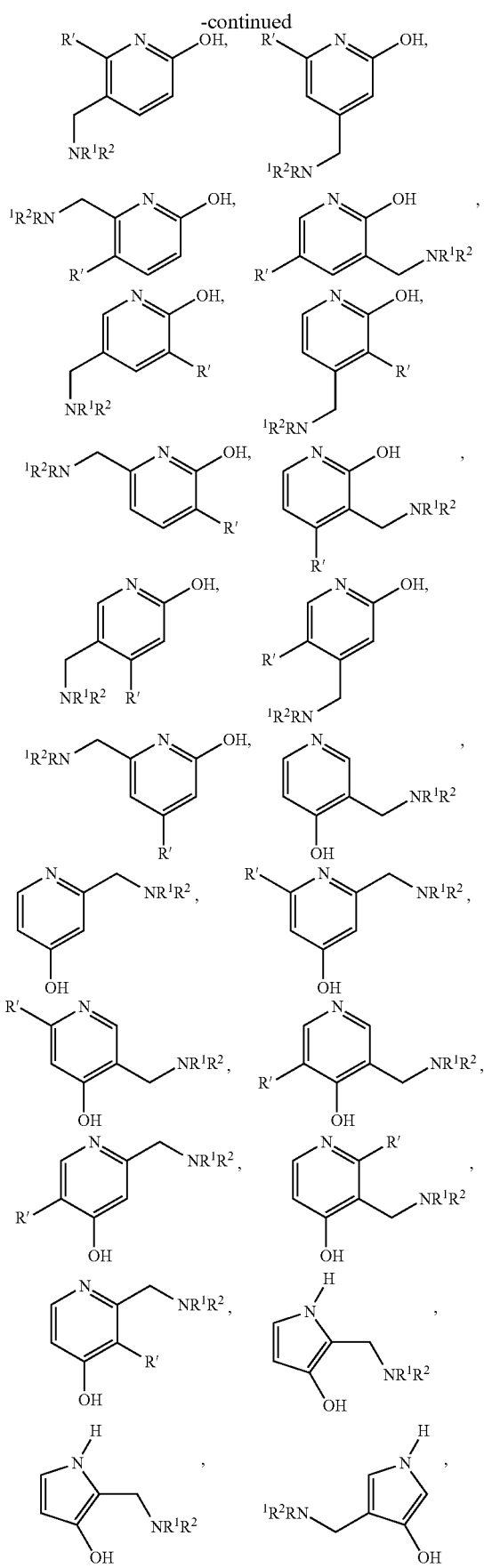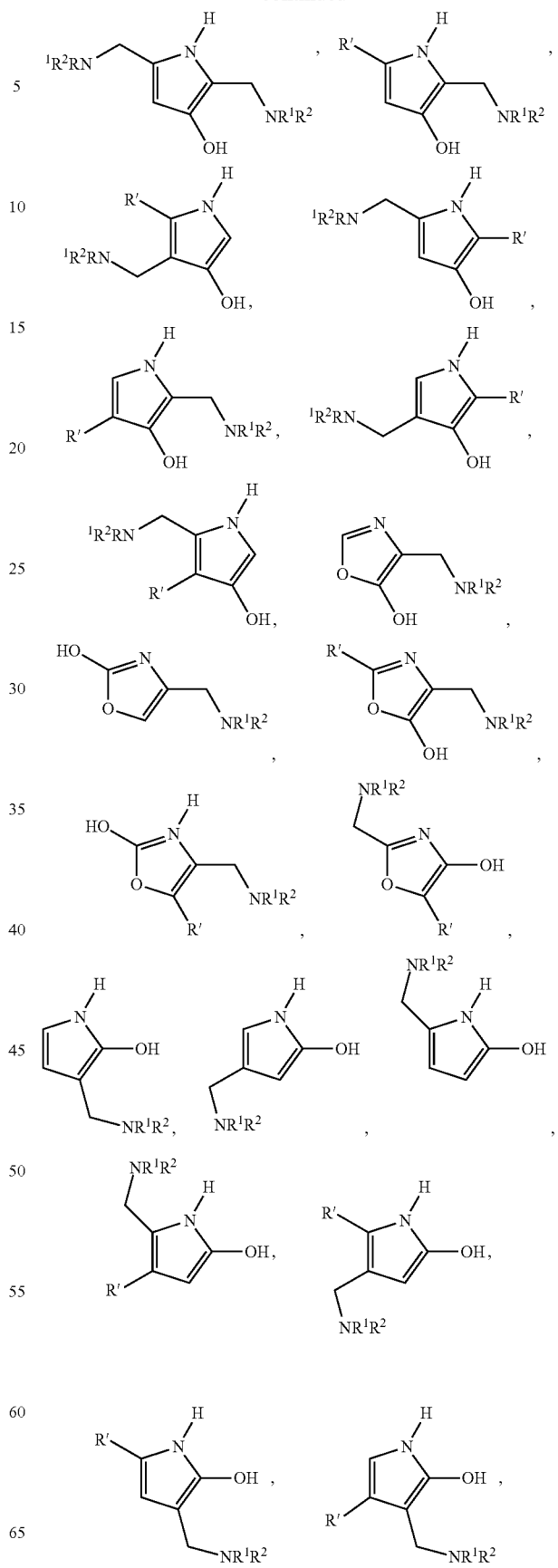

-continued
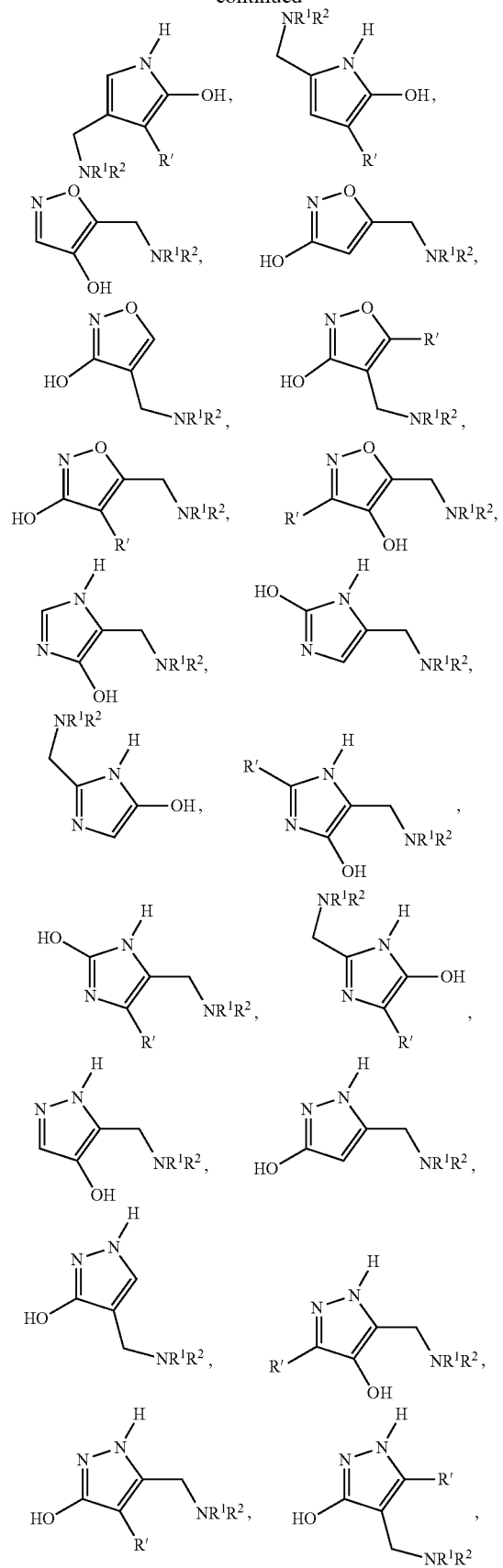
wherein R' is $C_1$-$C_6$ alkyl, aryl, OH, OR', $NH_2$, NHR', or $NR'_2$ or an acetylcholinesterase inhibitor.
In other examples of Formula I or II, the compound can be selected from:
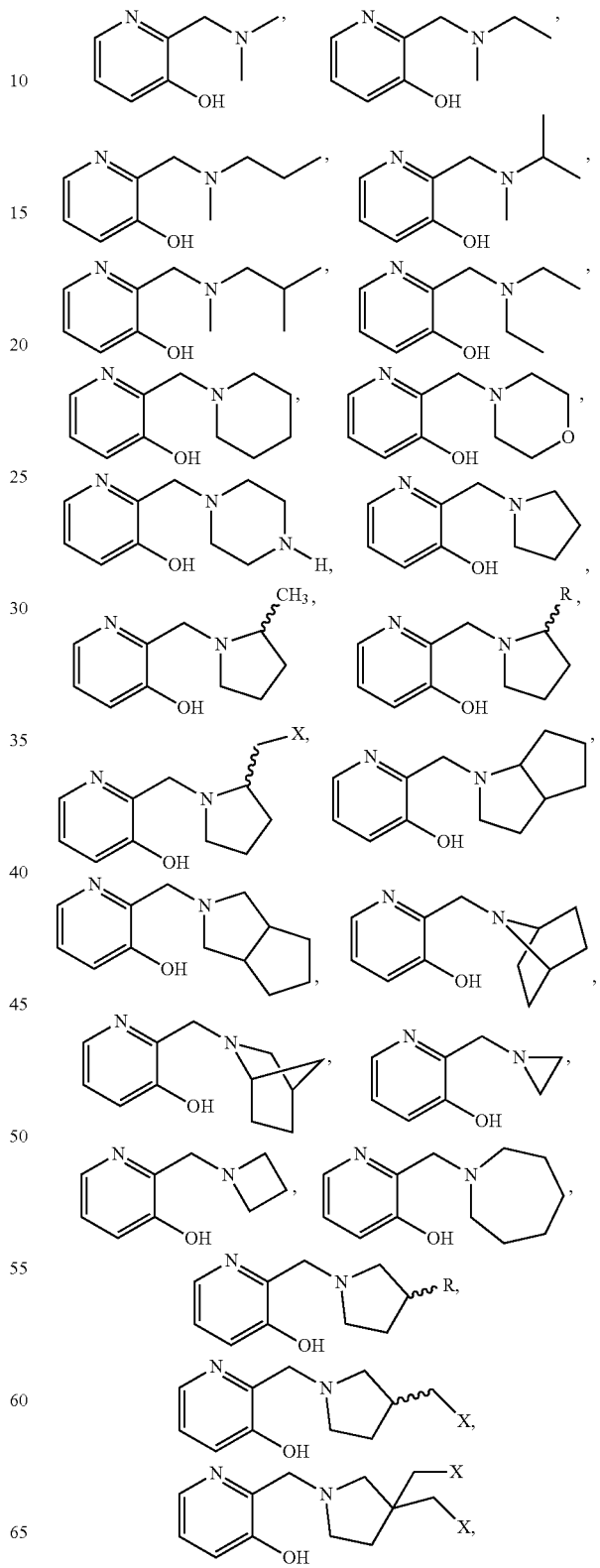

-continued
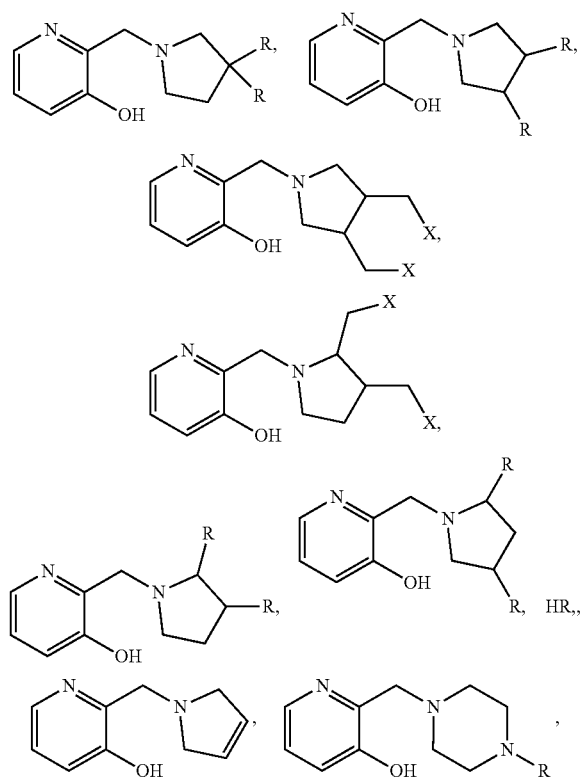
wherein R is $C_1$-$C_6$ alkyl and X is OH, OR, $NH_2$, NHR, or $NR_2$. In some embodiments, the aryl ring can include an acetylcholinesterase inhibitor.
In further examples of Formula I or II, the compound can be selected from:
-continued
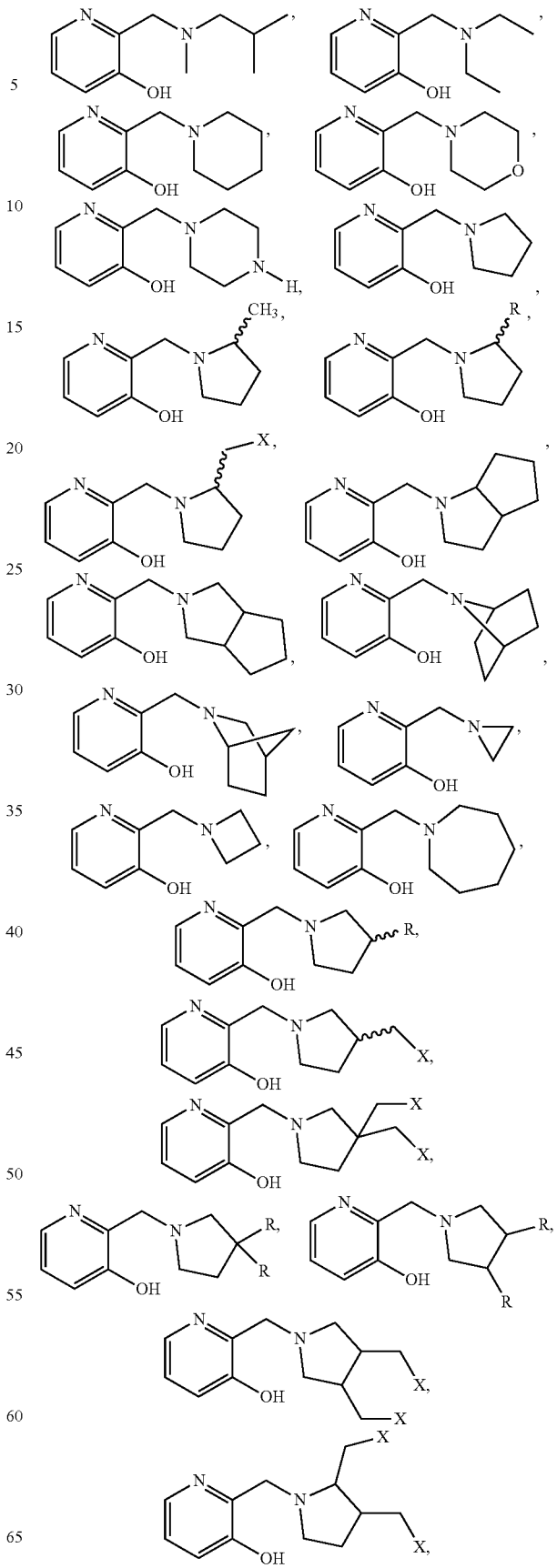

-continued

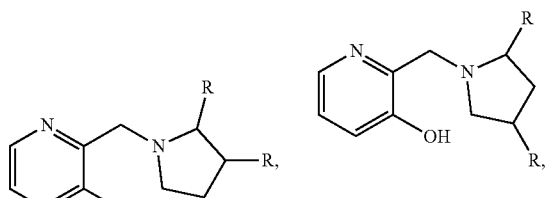

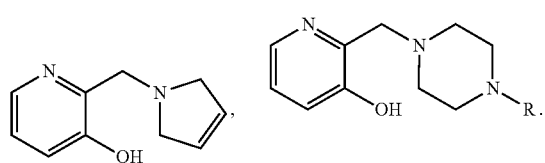

wherein R is $C_1$-$C_6$ alkyl and X is OH, OR, $NH_2$, NHR, OR $NR_2$.

In some aspects of Formula I, the compound can have a structure represented by Formula II-H to II-Q:

Formula II-H
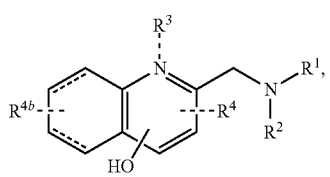

Formula II-I

Formula II-J
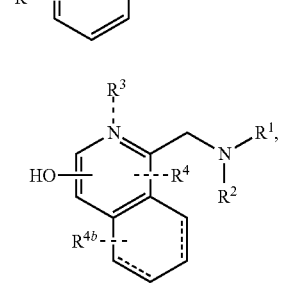

Formula II-K

Formula II-L
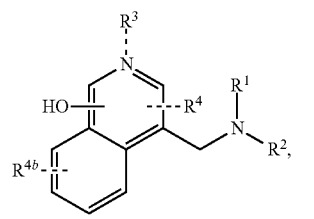

Formula II-M
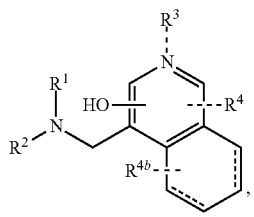

Formula II-N
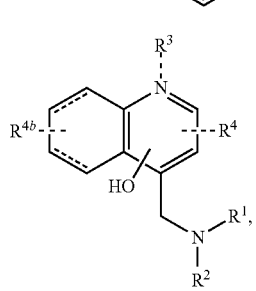

Formula II-O
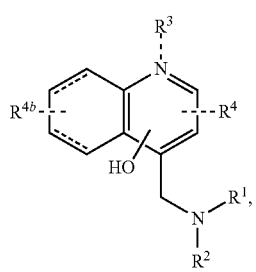

Formula II-P
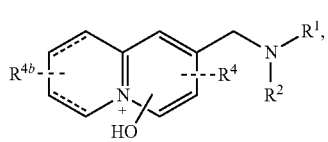

Formula II-Q
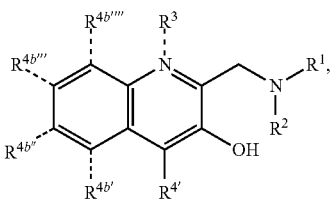

wherein $R^3$, $R^4$, and $R^{4b}$ are optionally present, and wherein $R^{4b}$ when present is selected from $C_1$-$C_6$ alkyl, halogen, $C_1$-$C_6$ alkyl halide, $C_1$-$C_6$ alkoxy, nitrile, amine, alkylamine, and alkylammonium.

In some embodiments of Formula II-H, the compound is represented by a structure having the Formula II-H-1:

Formula II-H-1
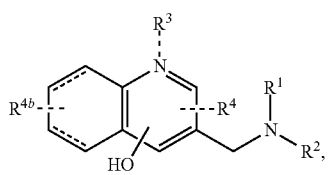

wherein $R^3$, $R^{4'}$, $R^{4b'}$, $R^{4b''}$, $R^{4b'''}$ and $R^{4b''''}$ are optionally present, and when present, $R^{4'}$, $R^{4b'}$, $R^{4b''}$, $R^{4b'''}$ are independently selected from $C_1$-$C_6$ alkyl, halogen, $C_1$-$C_6$ alkyl halide, $C_1$-$C_6$ alkoxy, nitrile, amine, alkylamine, and alkylammonium.

In some examples of Formula II-H-II-Q, the compound is represented by a structure having the Formula:

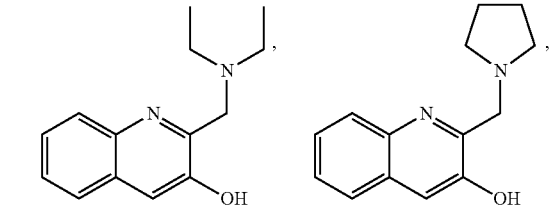

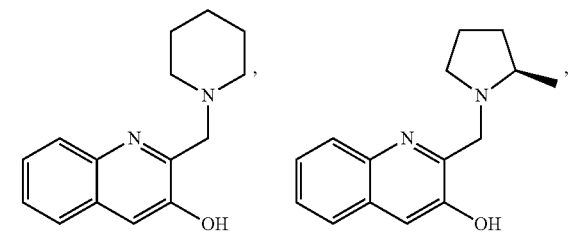

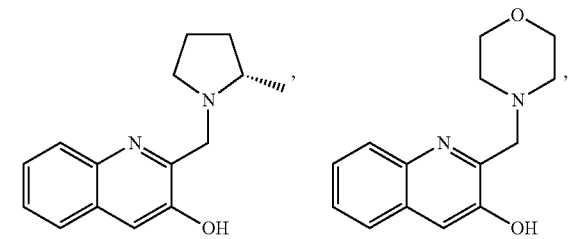

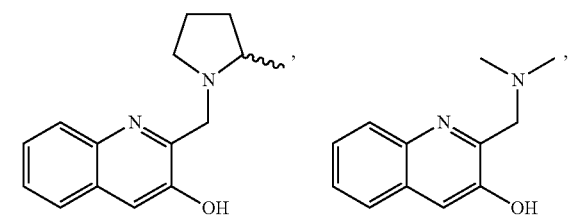

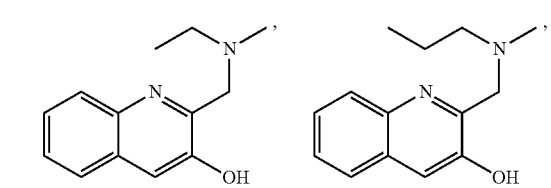

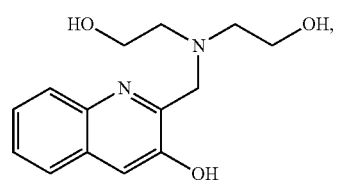

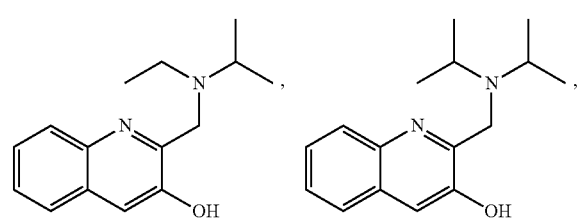

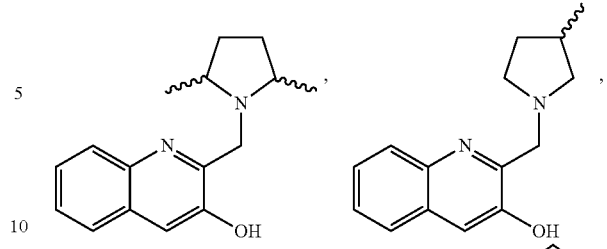

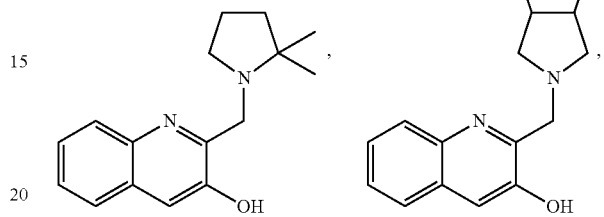

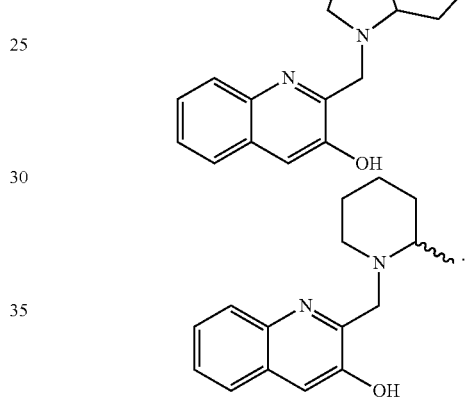

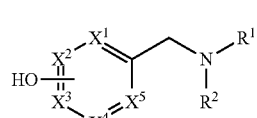

In some aspects, the compound can have a structure represented by Formula III:

Formula III $$\text{HO}-\underset{X^3=X^4}{\overset{X^2=X^1}{\underset{\|}{\bigcirc}}}\underset{X^5}{\overset{}{\diagdown}}\underset{R^2}{\overset{R^1}{\diagdown N}}$$

wherein
$X^1$-$X^5$ are independently selected from N, NR', and CR',
R' is, independently for each occurrence, selected from hydrogen, $C_1$-$C_6$ alkyl, $C_1$-$C_6$ alkyl halide, $C_1$-$C_6$ alkoxy, hydroxyl, halogen, amine, alkylamine, alkylammonium, or where two R' groups combine to form a substituted or unsubstituted fused $C_5$-$C_7$ cyclic moiety;
$R^1$ and $R^2$ are independently selected from $C_1$-$C_6$ alkyl, $C_1$-$C_6$ alkyl halide, or $C_1$-$C_6$ alkoxy, and wherein $R^1$ and $R^2$ are optionally substituted with alkyl, heteroalkyl, cycloalkyl, cycloheteroalkyl, aryl, heteroaryl, alkyl halide, halogen, alkoxy, amine, alkylamine, and alkylammonium; and
wherein at least one of $X^1$-$X^5$ is N or NR'.
In certain embodiments of Formula III, $R^1$ and $R^2$ can combine to form a monocyclic heterocyclic group, a bicyclic heterocyclic group, or a tricyclic heterocyclic group. In certain embodiments of Formula III, $R^1$ and $R^2$ can combine to form a substituted or unsubstituted pyrrolidine, substituted or unsubstituted piperidine, substituted or unsubstituted piperazine, substituted or unsubstituted morpholine, wherein the substituent can be selected from $C_1$-$C_6$ alkyl, $C_1$-$C_6$ alkyl halide, $C_1$-$C_6$ alkoxy, hydroxyl, halogen, amine, alkylamine, and alkylammonium.

In certain embodiments of Formula III, the compound can be represented by a structure having the Formula III-A to III-G:

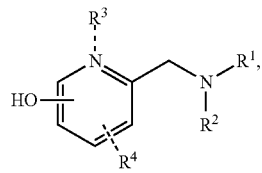

Formula III-A

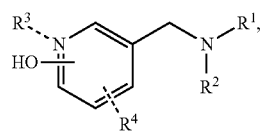

Formula III-B

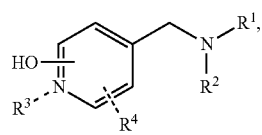

Formula III-C

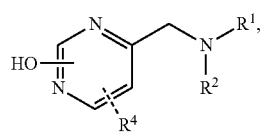

Formula III-D

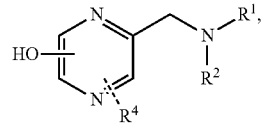

Formula III-E

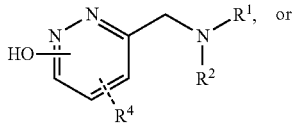

Formula III-F

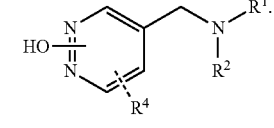

Formula III-G $R^3$ and $R^4$ can be absent or present in Formula III-A to Formula III-G. In some examples, $R^3$ is absent. In other examples, $R^3$ is present. In some examples, $R^4$ is absent. In other examples, $R^4$ is present. In still other examples, more than one $R^4$ are present. When present, $R^3$ and $R^4$ can be independently selected from $C_1$-$C_6$ alkyl, halogen, $C_1$-$C_6$ alkyl halide, $C_1$-$C_6$ alkoxy, nitrile, amine, alkylamine, alkylammonium, or an acetylcholinesterase inhibitor.

In some aspects, the compound can have a structure represented by Formula IV:

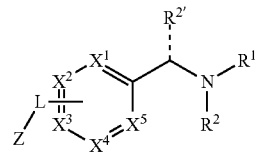

Formula IV wherein $X^1$-$X^5$ are independently selected from N, NR', C, and CR', wherein R' is independently selected from hydrogen, $C_1$-$C_6$ alkyl, $C_1$-$C_6$ alkyl halide, $C_1$-$C_6$ alkoxy, hydroxyl, halogen, amine, alkylamine, and alkylammonium;

$R^1$ and $R^2$ combine to form a 3 to 7 membered aliphatic ring, wherein the 3 to 7 membered aliphatic ring is substituted with $C_1$-$C_6$ alkyl, $C_1$-$C_6$ alkyl halide, $C_1$-$C_6$ alkoxy, hydroxyl, halogen, amine, alkylamine, and alkylammonium;

$R^{2'}$ is optionally present and selected from $C_1$-$C_6$ alkyl, $C_1$-$C_6$ alkyl halide, $C_1$-$C_6$ alkoxy, and $C_1$-$C_6$ alkyl amine, or $R^1$ and $R^{2'}$ or $R^2$ and $R^{2'}$ combine to form a 5 to 7 membered aliphatic ring;

L is a bond or a linker; and

Z is an acetylcholinesterase inhibitor; and wherein at least one of $X^1$-$X^5$ is N or NR', and at least one of $X^1$-$X^5$ is C—OH.

In certain embodiments of Formula IV, $R^1$ and $R^2$ can combine to form a monocyclic heterocyclic group, a bicyclic heterocyclic group, or a tricyclic heterocyclic group. In certain embodiments of Formula IV, $R^1$ and $R^2$ can combine to form a substituted or unsubstituted pyrrolidine, substituted or unsubstituted piperidine, substituted or unsubstituted piperazine, substituted or unsubstituted morpholine, wherein the substituent can be selected from $C_1$-$C_6$ alkyl, $C_1$-$C_6$ alkyl halide, $C_1$-$C_6$ alkoxy, hydroxyl, halogen, amine, alkylamine, and alkylammonium.

In certain embodiments of Formula IV, the compound can be represented by a structure having the Formula IV-A:

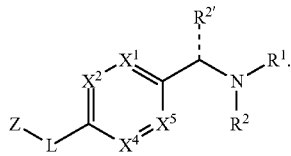

Formula IV-A

In certain embodiments of Formula IV, the acetylcholinesterase inhibitor can be selected from (−)-phenserine, donepezil, rivastigmine, metrifonate, tacrine, physostigmine, (−) carbamates, eptastigmine, galantamine, huperzine A and pharmaceutically acceptable salts and esters thereof.

In some examples of Formula IV, the acetylcholinesterase inhibitor can be donepezil. For example, the compounds disclosed herein can be represented by a structure having the Formula IV-B:

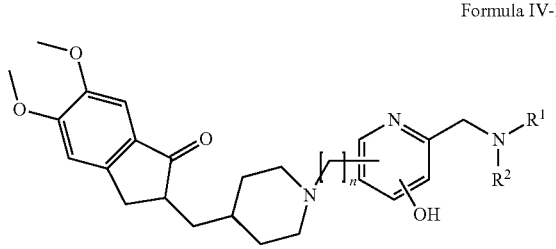

Formula IV-B

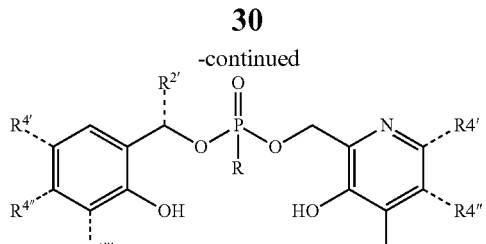

Formula C

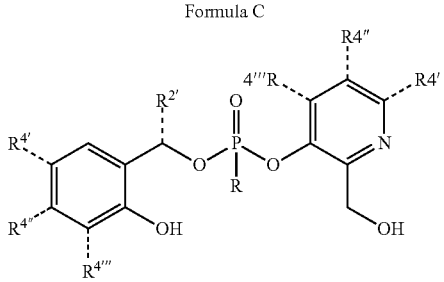

Formula D

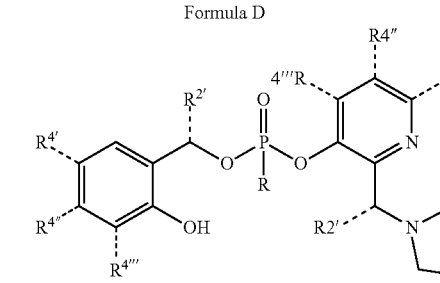

Formula E wherein
n is an integer from 1 to 6.

As disclosed herein, the compounds described herein can realkylate aged acetylcholinesterase. In particular, progressive inhibition of cholinesterases by organophosphates results from phosphorylation of the active-site serine. Phosphorylated cholinesterases may undergo a dealkylation reaction of the organophosphorus moiety leading to "aged" enzyme, i.e. conversion of the inhibited enzyme into a non-reactivable form. The compounds described herein can realkylate the anionic aged acetylcholinesterase adduct, which produce a neutral phosphyl adduct or another charged adduct that can be reactivated by a compound as described herein or known medicinal agents for reactivating acetylcholinesterase.

Provided herein are compositions comprising a realkylated phosphyl adduct, the realkylated phosphyl adduct produced by a method comprising contacting aged acetylcholinesterase with a composition comprising an effective amount of a compound provided herein, and allowing the compound to react with the aged acetylcholinesterase to produce the realkylated phosphyl adduct.

Also provided herein are compositions comprising a realkylated phosphyl adduct, the realkylated phosphyl adduct produced by a method comprising contacting a phosphonate anion with a composition comprising an effective amount of a compound provided herein, and allowing the compound to react with the phosphonate anion to produce the realkylated phosphyl adduct.

Without wishing to be bound by theory, as an example, a compound of Formula II-A-1 can react with the phosphonate anion as follows to produce one or more of Formulas A-Formula E:

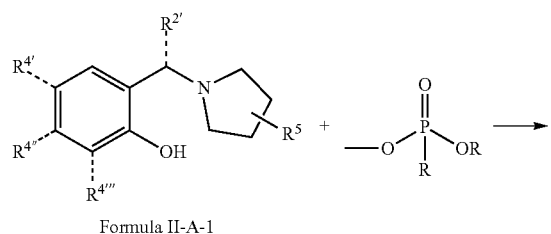

Formula II-A-1

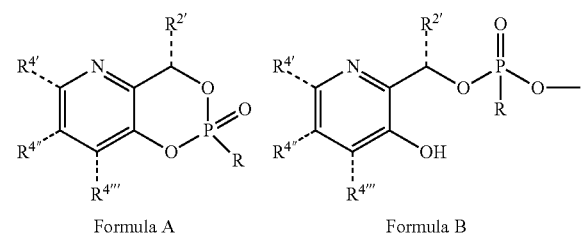

Formula A        Formula B wherein R is an alkyl or alkoxy (O-alkyl) group.

Pharmaceutical Compositions

The disclosed compounds can be used therapeutically in combination with a pharmaceutically acceptable carrier. The carrier would naturally be selected to minimize any degradation of the active ingredient and to minimize any adverse side effects in the subject, as would be well known to one of skill in the art.

The disclosed compounds may be in solution, suspension, incorporated into microparticles, liposomes, or cells, or formed into tablets, gels, or suppositories. Suitable carriers and their formulations are described in Remington: The Science and Practice of Pharmacy ($22^{nd}$ ed.) eds. Loyd V. Allen, Jr., et al., Pharmaceutical Press, 2012. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered. Pharmaceutical carriers are known to those skilled in the art. These most typically would be standard carriers for administration of vaccines to humans, including solutions such as sterile water, saline, and buffered solutions at physiological pH. Pharmaceutical compositions may include carriers, thickeners, diluents, buffers, preservatives, surface active agents and the like in addition to the vaccine. Pharmaceutical compositions may also include one or more active ingredients such as antimicrobial agents, anti-inflammatory agents, anesthetics, and the like.

The disclosed compounds are preferably formulated for delivery via intranasal, intramuscular, subcutaneous, parenteral, transdermal or sublingual administration.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Parenteral administration of the disclosed compounds, if used, is generally characterized by injection. Injectables can be prepared in conventional forms, either as liquid solutions or suspensions, solid forms suitable for solution of suspension in liquid prior to injection, or as emulsions.

For an oral administration form, the disclosed compounds can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, cornstarch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the disclosed compounds may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the disclosed compounds, if desired with the substances customary therefore such as solubilizers, emulsifiers or further auxiliaries are brought into solution, suspension, or emulsion. The disclosed compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that compositions comprising the disclosed compounds can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaluronic acid, chitin, chitosan and the like; other natural polymers, such as proteins (albumin, gelatin etc.), poly-L-lysine; sodium poly(acrylic acid); poly (hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na-CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release delivery systems. The disclosed compounds can be entrapped in the poly(lactide-co-glycolide) microsphere depot by a number of methods, including formation of a water-in-oil emulsion with water-borne compound and organic solvent-borne polymer (emulsion method), formation of a solid-in-oil suspension with solid compound dispersed in a solvent-based polymer solution (suspension method), or by dissolving the compound in a solvent-based polymer solution (dissolution method). One can attach poly(ethylene glycol) to compounds (PEGylation) to increase the in vivo half-life of circulating therapeutic proteins and decrease the chance of an immune response.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prodrug forms of the nucleoside compounds according to the present disclosure.

The exact amount of the compounds or compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products. A typical dosage of the disclosed vaccine used alone might range from about 1 µg/kg to up to 100 mg/kg of body weight or more per vaccination, such as 10 µg/kg to 50 mg/kg, or 50 µg/kg to 10 mg/kg, depending on the factors mentioned above.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Some of the disclosed compounds may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g., about 10, 25, 50, 100, 200, 300 or 400 mg per unit dosage.

The disclosed compounds can also be used to supplement existing treatments. Therefore, the disclosed compositions can further include (or be administered in combination with) a second compound that can ameliorate, diminishing, reversing, treating or preventing the toxic effects of an organophosphorus compound in a subject. For example, the disclosed compositions can further include (or be administered in combination with) one or more of antidotes for organophosphate exposure. In a specific embodiment, the disclosed compounds can be administered with (in combination in the same composition, in combination but in separate compositions, or sequentially) carbamates (e.g., pyridostigmine), anti-muscarinics (e.g., atropine), cholinesterase reactivators (inhibited ChE-reactivators) such as pralidoxime chloride (2-PAM, Protopam), anti-convulsives, or organophosphorus bioscavengers.

The pharmaceutical compositions and formulations disclosed herein can be administered for prophylactic and/or therapeutic treatments. In therapeutic applications, compositions are administered to a subject already exposed to a toxin, or exposed to any agent or chemical causing or resulting in excessive acetylcholine stimulation in the brain, e.g., exposure to an organophosphorus compound such as a nerve agent.

The amount of pharmaceutical composition adequate to accomplish this is defined as a "therapeutically effective dose." The dosage schedule and amounts effective for this use, i.e., the "dosing regimen," will depend upon a variety of factors, including the stage of the condition, the severity of the condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Methods of Use

The compounds and compositions disclosed herein provide antidotes which are able to "resurrect" the aged form of acetylcholinesterase (AChE) to an active, native state, real-kylate the anionic aged form of AChE back to a neutral, phosphylated (inhibited) serine residue and then by reactivating the inhibited form to the native AChE. In some embodiments, the compounds and compositions disclosed herein can reverse inhibition of acetylcholinesterase by an organophosphorus compound. In some embodiments, the compounds and compositions disclosed herein can reactivate aged acetylcholinesterase inhibited by or conjugated to an organophosphorus compound. In some embodiments, the compounds and compositions disclosed herein can realkylate aged acetylcholinesterase inhibited by or conjugated to an organophosphorus compound.

In certain embodiments, the compounds and compositions disclosed herein provides methods for ameliorating, diminishing, reversing, treating or preventing the toxic effects of an organophosphorus compound in a subject. In certain embodiments, the compounds and compositions disclosed herein provides methods for ameliorating, diminishing, reversing, treating or preventing the toxic effects of an organophosphorus compound in the central nervous system of a subject. The method can include administering to the subject or an individual in need thereof, a compound or a composition disclosed herein.

Also provided herein are methods for reactivating acetylcholinesterase inhibited by or conjugated to an organophosphorus compound comprising contacting the acetylcholinesterase with a composition comprising an effective amount of a compound having a structure described herein are provided. Methods for realkylating aged acetylcholinesterase inhibited by or conjugated to an organophosphorus compound comprising contacting the acetylcholinesterase with a composition comprising an effective amount of a compound having a structure described herein are provided. The organophosphorus compound can be a nerve agent.

The compounds and compositions can be administered using any suitable device such as a pump, a subcutaneous infusion device, a continuous subcutaneous infusion device, an infusion pen, a needle, a reservoir, an ampoule, a vial, a syringe, a cartridge, a disposable pen or jet injector, a prefilled pen or a syringe or a cartridge, a cartridge or a disposable pen or jet injector, or a two chambered or multi-chambered pump. The organophosphate toxicity, poisoning or toxic exposure may be caused by exposure of the subject or individual to an alkyl methylphosphonate or related nerve agent, or an alkylphosphorate insecticide, an herbicide, an insecticide, a nerve gas or nerve agent, a parathion, a malathion, a methyl parathion, a chlorpyrifos, a diazinon, a dichlorvos, a phosmet, a fenitrothion, a tetrachlorvinphos, an azamethiphos or an azinphos methyl, a soman (O-pinacolyl methylphosphonofluoridate), a tabun (ethyl N,N-dimethyl-phosphoramido-cyanidate) or a sarin ((RS)-propan-2-yl methylphosphonofluoridate).

In certain embodiments, the compounds and compositions provide for treating, preventing or ameliorating excessive acetylcholine stimulation in the CNS, including the brain, or in the periphery, including the peripheral nervous system (PNS), comprising administering to a patient or an individual in need thereof, a compound or a composition disclosed herein. Specifically, the compounds and compositions disclosed herein provides antidotes that cross the blood-brain barrier (BBB) to reactivate and/or realkylate organophosphate (OP)-inhibited human acetylcholinesterase (huAChE) in the central nerve system (CNS). In some embodiments, these compounds are uncharged reactivators of phosphorylated human acetylcholinesterase (huAChE) intended to realkylate the aged form of AChE in the CNS.

In certain embodiments, compounds and compositions disclosed herein are rapidly absorbed from the site of administration (e.g., oral, inhalation, or intramuscular), cross the blood-brain barrier as a neutral species, displace the covalently attached OPs, e.g., from a organophosphate toxicant such as a pesticide or a nerve agent, realklylate aged AChE, and restore AChE activity in the brain and periphery. In certain embodiments, compounds and compositions disclosed herein provide immediate protection from exposure, as well as prevention, of OP exposure, e.g., protection or prevention of immediate and recurring seizures that result from excessive acetylcholine stimulation in the brain. In some examples, compounds and compositions disclosed herein can be an antidote for poisoning by organophosphate (e.g., diisopropylfluorophosphates and echothiophate) and carbamylating drugs (e.g., physostigmine, neostigmine and pyridostigmine).

In certain embodiments, compounds and compositions disclosed herein can not only cross the blood-brain barrier to reactivate acetylcholinesterase in the CNS and peripheral nervous system, but are also effective as antidotes and protective (prophylactic) agents. For example, as a prophylactic agent, the compounds can be used in accidents or in poison gas (e.g., nerve agent) warfare, e.g., paraoxon, sarin, cyclosarin and VX attacks. In certain embodiments, compounds and compositions disclosed herein can limit the toxicity and treat potential of organophosphate nerve agents by reactivating and/or realkylating butyrylcholinesterase in plasma and tissues.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of the disclosure. Unless indicated otherwise, parts are parts by weight, temperature is in ° C. or is at ambient temperature, and pressure is at or near atmospheric.

Example 1: Demonstration of In Vitro Resurrection of Aged Acetylcholinesterase after Exposure to Organophosphorus Chemical Nerve Agents Introduction: After inhibition of acetylcholinesterase (AChE) by organophosphorus (OP) nerve agents, a dealkylation reaction, referred to as aging, of the phosphylated serine can occur. When aged, known reactivators of OP-inhibited AChE are no longer effective. Realkylation of aged AChE may provide a route to reverse aging. In this example, a library of quinone methide precursors (QMPs) as realkylators of aged AChE were synthesized. The lead compound ($C_8$) from an in vitro screening, combined with 2-pralidoxime (2-PAM), successfully resurrected 32.7% and 20.4% of the activity of methylphosphonate-aged and isopropyl phosphate-aged electric eel AChE, respectively, after 4 days of treatment at pH 8. C8 displays both realkylator and reactivator activities. Resurrection of PiMP-aged AChE was significantly pH-dependent, recovering 21% of native activity at pH 9 after 1 day. C8 is also effective against DFP-aged human AChE.

Background: Acetylcholinesterase (AChE) is an enzyme found in brain synapses, neuromuscular junctions and erythrocytes. AChE selectively hydrolyzes the neurotransmitter acetylcholine. Organophosphorus (OP) compounds phosphylate the catalytic serine of AChE, and inhibition of AChE results in the accumulation of acetylcholine. OP exposure may lead to death due to seizures or respiratory failure. (M. Eddleston, et al., *Lancet* 371, 597-607 (2008); M. Lotti, in *Handbook of Pesticide Toxicology*, R. I. Krieger, W. C. Krieger, Ed. (Academic Press, ed. 2, 2001), vol. 2, chap. 51, pp. 1043-1085; and B. Holmstedt, *Pharmacol Rev* 11, 567 (1959)). Thus, OPs are toxic and have been used as pesticides and chemical warfare agents. OP-inhibited AChE can be reactivated by oximes. (B. Sanson, et al., *J Med Chem* 52, 7593-7603 (2009)).

Exposure of AChE to OP compounds is complicated by an aging process in which loss of the alkyl side chain of the phosphylated serine produces an oxyanion of OP-poisoned AChE. (J. H. Fleisher, et al., *Biochem Pharmacol* 14, 641-650 (1965) and F. Berends, et al., *Biochimica et Biophysica Acta* 34, 576-578 (1959)). Oximes, such as 2-pralidoxime (2-PAM), are ineffective against aged AChE. Some OP compounds, such as soman, with an aging half-time ($t_{1/2}$) of only several minutes, provide only a minimal chance for medical treatment. (A. Shafferman, et al. *Biochem J* 318, 833-840 (1996)). After decades of research, no clinical treatment has been developed to resurrect aged AChE.

To reverse aging, realkylation of the phosphylated oxyanion has been proposed as a strategy against this dealkylation process, (P. Blumbergs, et al., *J Org Chem* 34, 4065-4070 (1969)) including unsuccessful efforts from 1970 by Steinberg et al. (G. M. Steinberg, et al., *J Med Chem* 13, 435-446 (1970)) as well as more recent efforts led by Quinn (J. J. Topczewski, et al., *Org Lett* 15, 1084-1087 (2013)). With the negative charge on the phosphylated serine being neutralized by some sort of electrophilic realkylation process, oximes should reactivate AChE again. Several types of electrophilic alkylating agents including sulfonates (P. Blumbergs, et al.), haloketones (G. M. Steinberg, et al.), sulfoniums (N. B. Chandar, et al., *Chem-Biol Interact* 223, 58-68 (2014)), and methoxypyridiniums (J. J. Topczewski, et al.) were evaluated as potential AChE realkylators. Recently, from an in silico study, Khavrutskii and Wallqvist suggested the possibility to resurrect aged AChE by β-aminoalcohols, by a direct process without proceeding through a realkylation event (I. V. Khavrutskii, et al., *Chemistry Select* 2, 1885-1890 (2017)). However, prior to this report, no experimental evidence has been reported for the efficacy of any drug to realkylate aged AChE (Q. Zhuang, et al., *Ann Ny Acad Sci* 1374, 94-104 (2016)). Herein is reported the first family of compounds that demonstrate in vitro efficacy.

Quinone methides (QMs, FIG. 1A) can be regarded as carbocations stabilized by resonance delocalization. Quinone methide precursors (QMPs, FIG. 1A) are derivatives of QMs with a leaving group attached to the partially positively charged carbon. QMPs can be attacked by nucleophiles either directly via $S_N2$ substitution, or via the corresponding QMs as reactive intermediates (FIG. 1B). Protein and nucleic acid alkylation by QMPs has been reported (D. C. Thompson, et al., *Chem-Biol Interact* 126, 1-14 (2000); J. L. Bolton, et al., *Chem-Biol Interact* 107, 185-200 (1997); P. G. McCracken, et al., *J Org Chem* 62, 1820-1825 (1997); M. Reboud-Ravaux, et al., in *Quinone Methides*, S. E. Rokita, Ed. (John Wiley & Sons, Inc., ed. 2009), chap. 11, pp. 357-383; Q. Zhou, et al., *Chem Res Toxicol* 24, 402-411 (2011); and B. A. Bakke, et al., *J Org Chem* 70, 4338-4345 (2005)). Phosphodiesters and dibutyl phosphate, which structurally resemble the phosphyl group of aged AChE, have been alkylated by QMs. (A. Bakke, et al., *J Org Chem* 70, 4338-4345 (2005); Q. Zhou, et al.; *J Org Chem* 64, 2847-2851 (1999); and Q. Zhou, et al., *J Org Chem* 66, 7072-7077 (2001)).

Herein is reported a series of QMPs as realkylators of aged AChE, providing up to ~33% in vitro resurrection of electric eel AChE (eeAChE) for a methylphosphonate or up to 20% for a phosphate, after 4 days. Guided by in silico studies, a library of candidate compounds was synthesized. Their activities were characterized by Ellman's assay, and resurrection of AChE was confirmed by bottom-up proteomics.

QMP screening assays with electric eel acetylcholinesterase (eeAChE) were carried out, where eeAChE is first incubated with an OP to inhibit the enzyme, and allowed an appropriate amount of time for the enzyme to age. The re-inhibited OP AChE complex was then treated with 2-PAM, to effectively reactivate any inhibited, but un-aged enzyme. The sample was then screened by Ellman's assay for residual AChE activity. If activity was present, the inhibition and aging process is repeated. This procedure ensures complete aging of the enzyme prior to screening QMP realkylators. For the purpose of the screening results reported within this example, eeAChE was inhibited and aged with one of three OPs: CMP, PiMP, or diisopropyl fluorophosphate (DFP). Importantly, the methylphosphonate-aged AChE product resulting from aging with CMP or PiMP was not only the aging product of the cyclosarin or soman-inhibited AChE respectively, but also the product of AChE inhibited and aged by any other methylphosphonate nerve agents (e.g. sarin, cyclosarin, VX, etc.).

Once the aged AChE sample was obtained, it was then incubated with individual potential QMP realkylators in the presence of 2-PAM under near physiological conditions (37° C., phosphate buffer pH 7.4). The purpose of adding 2-PAM to the assay is to facilitate the reactivation of the realkylated enzyme after reaction with the alkylator, thereby generating the active, native enzyme. The enzyme activity was then evaluated by Ellman's assay.

Preparation of Aged AChE: Some OPs (mainly the phosphonates, which are commonly seen in G- and V-type chemical warfare agents) are chiral, and the stereoisomers can inhibit and/or age at different rates. (J. H. Keijer, et al., *Biochimica et Biophysica Acta* 185, 465-468 (1969)). Inhibited AChE may remain un-aged even after reacting for longer than the apparent $t_{1/2}$, if the enzyme is inhibited by the slower aging OP stereoisomer. Reactivation of the residual un-aged, but inhibited, AChE can interfere with the observation of the resurrection of aged AChE and may lead to artifacts.

Thus, AChE must be thoroughly aged and free of inhibited AChE. Two representative OPs (FIG. 1C) were exploited in this example. PiMP (a pinacolyl methylphosphonate ester), a soman analogue, was synthesized as reported by Amitai et al. (G. Amitai, et al., *Toxicology* 233, 187-198 (2007)). The resulting methylphosphonate-aged AChE is the aging product of any methylphosphonate nerve agent (e.g. sarin, soman, VX, etc.). The pesticide DFP (diisopropyl fluorophosphate) was also used to evaluate a phosphate at the serine residue (FIG. 1C). eeAChE was chosen as the target enzyme of these studies, considering its commercial availability and affordable cost.

To ensure complete aging, the methylphosphonate-aged AChE (treated with PiMP) was prepared via two rounds of aging, considering the chirality of PiMP. AChE was treated with 2-PAM after the first round of aging, in order to reactivate any residual inhibited AChE. Then PiMP was added to inhibit and age the enzyme again. The amount of residual inhibited or native AChE in the sample was significantly minimized, often <0.5% residual activity of a native AChE control. By contrast, to age AChE with achiral DFP, only one round of aging was needed.

Initial Libraries and Evaluation of QMPs for Realkylation of Aged AChE

Figure 3A:
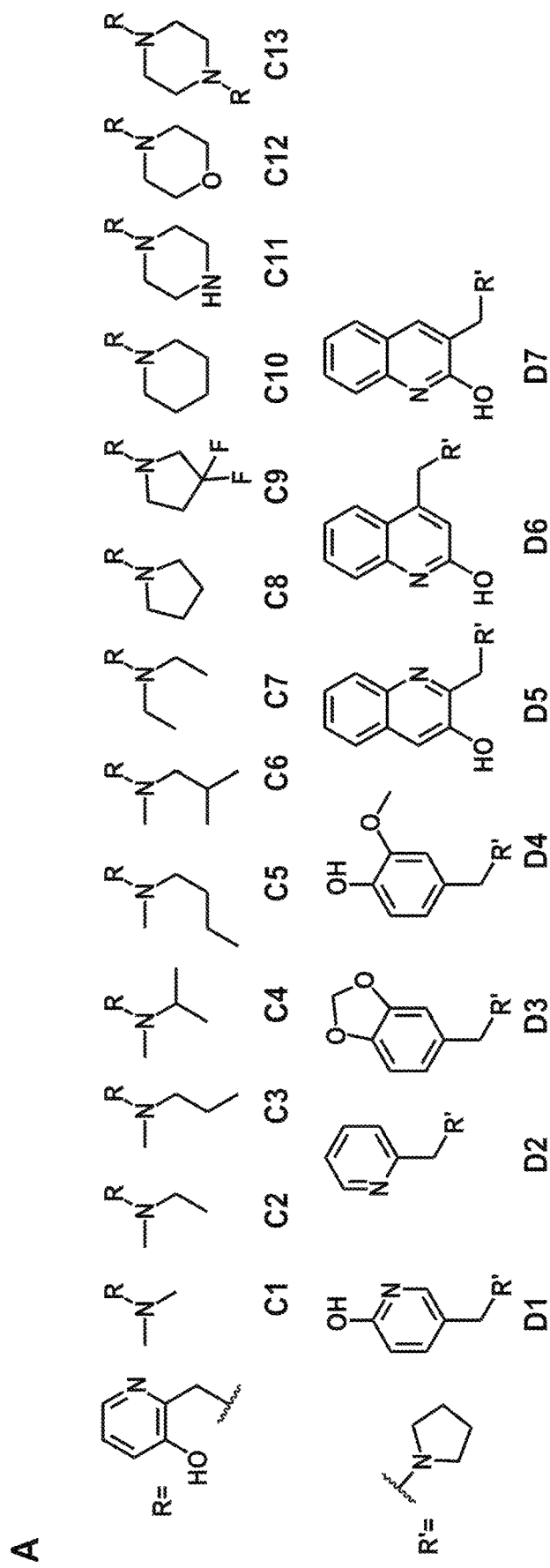
FIGS. 3A-3C show screening of QMPs against aged electric eel AChE (eeAChE, pH 8, 1 day).
Figure 7:
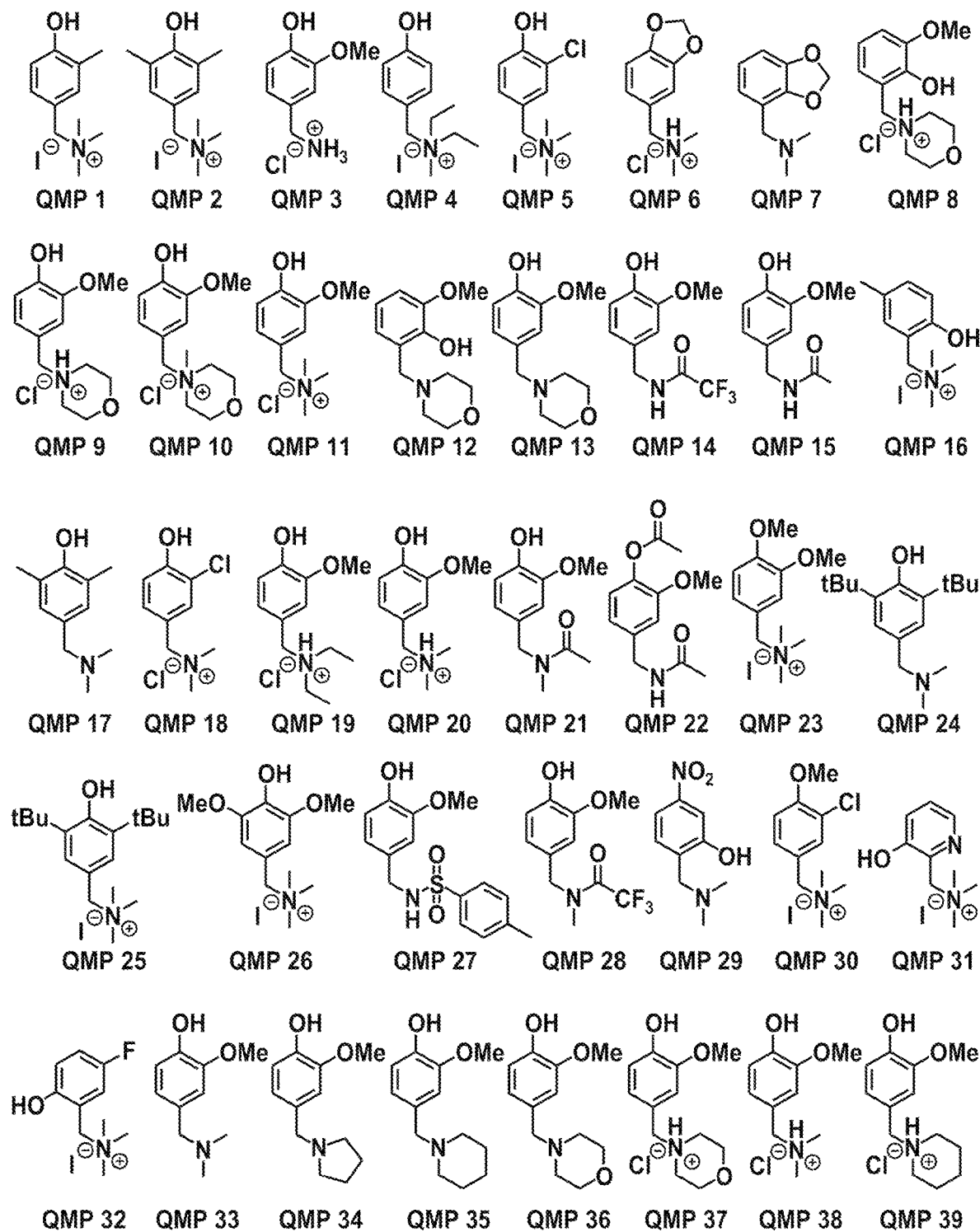
FIG. 7 shows structures of compounds disclosed herein.

A synthesis of QMPs utilized a reductive amination or Mannich phenol reaction and lead to the efficient development of a preliminary library of QMP compounds (FIGS. 3A and 7). The compounds shown in FIG. 7 include both ortho and para QMPs, as well as quaternary ammonium and neutral amine leaving groups. Four of the 2-aminomethyl-3-hydroxypyridines screened in FIG. 3A showed resurrection of AChE activity above the baseline value, with one compound, C8, bearing a pyrrolidine leaving group, reaching ~2.5% or 1.25% reactivation against PiMP-aged AChE or DFP-aged AChE respectively, after 24 h of reaction time.

Synthesis of 3,4-substituted Pyridine Alkylators: In an effort to probe structure activity relationships of $C_8$, regioisomers and structural analogs of C8 were explored. To better understand the importance of the relationship of the pyridine nitrogen and substituents on the ring, a series of 3,4-substituted pyridine QMP or "QMP like" analogs was proposed.

It is believed that substituents other than hydroxy, with lone pair electrons in resonance with the pyridine ring could facilitate the substitution reaction at the methylene carbon. For this reason, compounds 3.XVI with a chlorine and 3.XVII with an electron-donating methoxy group in the 4-position were proposed (Scheme 1).

Scheme 1: Proposed series of hydroxy pyridine realkylators.

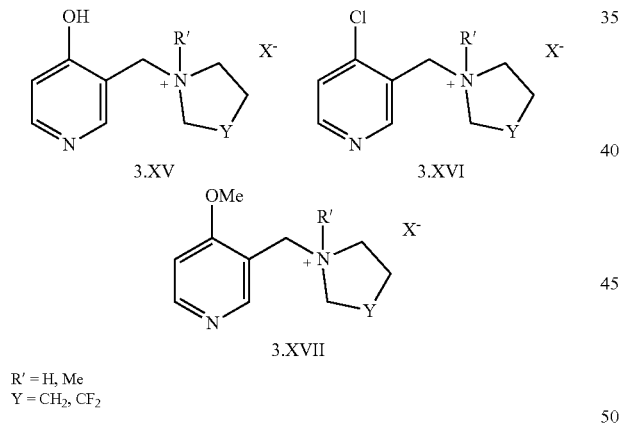

R' = H, Me
Y = CH$_2$, CF$_2$

From the analysis of the data in Scheme 1, it appears that the 5-membered pyrrolidine ring is the optimal amine leaving group. However, it was postulated that perhaps including an electron-withdrawing group on the pyrrolidine ring could lead to an increase in QM formation, and thus increase the potential for realkylation. Therefore in addition to using pyrrolidine, a 3,3-difluoropyrrolidine leaving group (Scheme 1, Y=CF$_2$) was also proposed.

The synthesis of the compounds proposed in Scheme 1 were envisioned to come from the common aldehyde intermediate 3.XIX which was obtained by formylation of the commercially available 4-chloropyridine (3.XVIII) by treatment with lithium diisopropylamine and subsequent trapping of the resulting anion with N,N-dimethylformamide (Scheme 2).

Scheme 2: Synthesis of common aldehyde intermediate 3.XIX.

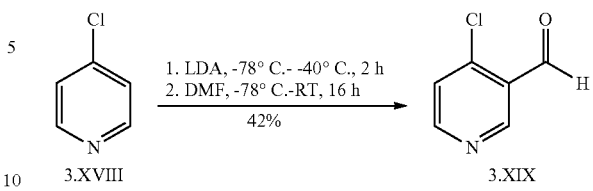

The 4-chloropyridine derivatives 3.XVI were then easily obtained by reductive amination of 3.XIX with pyrrolidine or 3,3-difluoropyrrolidine, followed by alkylation of the amine using iodomethane to give 3.XXI (Scheme 3, A), or protonation with oxalic acid to afford the oxalate salt 3.XXII (Scheme 3, A) or 3.XXIV (Scheme 3, B).

Scheme 3: Synthesis of 4-chloropyridine 3.XVI derivatives.

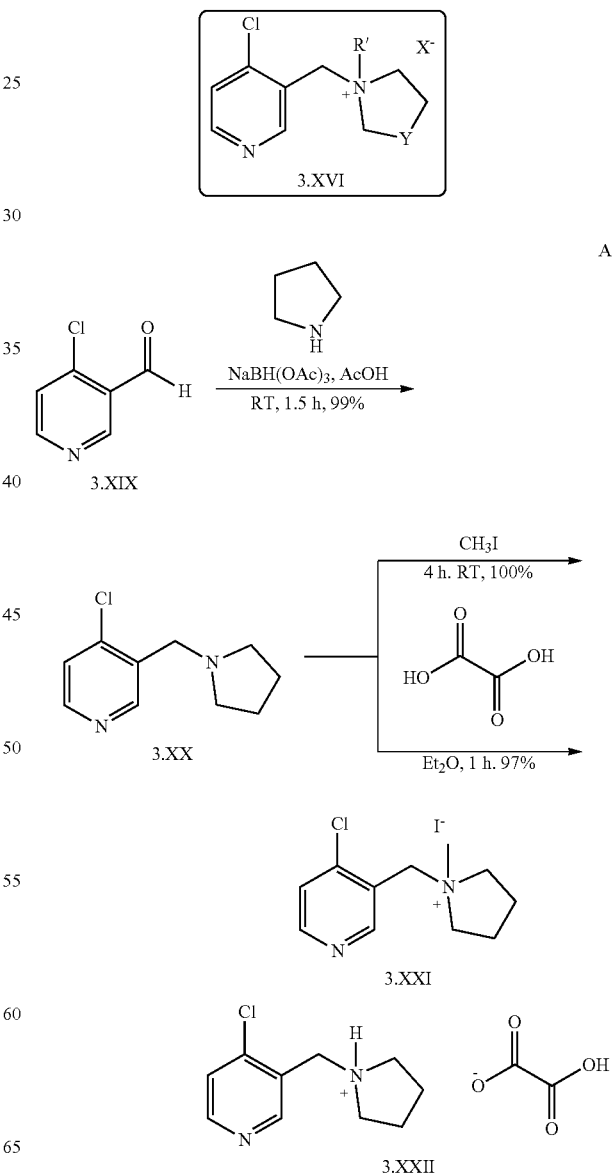

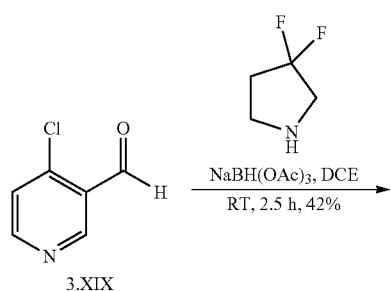
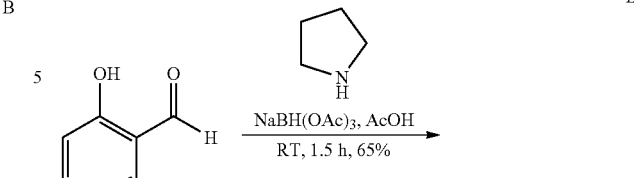
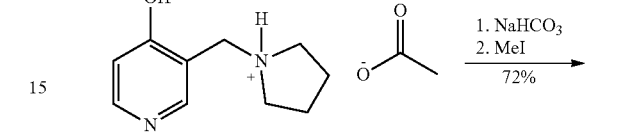
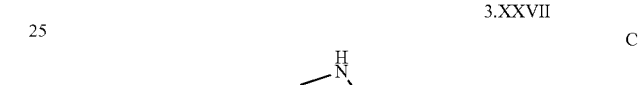
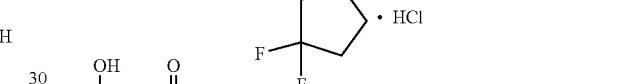

The 4-hydroxypyridine 3.XV type alkylators synthesis begins with the nucleophilic aromatic substitution of the electron-deficient ring of the common aldehyde intermediate 3.XIX with an aqueous HCl solution to afford aldehyde 3.XXV (Scheme 4, A). From 3.XXV, similarly described reductive amination conditions with pyrrolidine followed by protonation/methylation afford 3.XXVI and 3.XXVII respectively (Scheme 4, B), or reductive amination with 3,3-difluoropyrrolidine and protonation with oxalic acid to give the oxalate salt 3.XXIX (Scheme 4, C).

Scheme 4: Synthesis of 4-hydroxypyridine 3.XV derivatives.

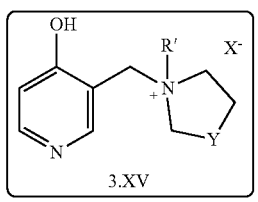
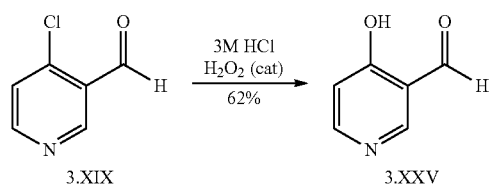

Resurrecting aged-AChE with the aid of an AChE Inhibitor: Thus far, in investigating a realkylator for the resurrection of aged-AChE, a fairly broad variety of QMP scaffolds had been synthesized, including benzyl, pyridyl, naphthyl, quinolinyl, and isoquinolinyl QMPs. Of these families of compounds, pyridyl compounds, specifically 2-methylamino-3-hydroxypyridines showed greater ability to resurrect aged AChE activity. Based on this, attention was turned to modifying the compound C8, in a manner to increase its ability to realkylate the aged enzyme, while leaving the proven effective 2-methylamino-3-hydroxy framework intact. It was postulated that increasing the affinity of the alkylator for the active site of the enzyme could potentially lead to an increase in activity for the alkylating compounds. The drug donepezil was observed.

Donepezil, trade named Aricept® is a benzylpiperidine with a propensity to inhibit AChE with a half maximal inhibitory concentration (IC50) of 5.7 nM. The drug was discovered by the Eisai company (and later bought and marketed by Pfizer), and has been FDA approved for the treatment of Alzheimer's disease since 1996. Interestingly, the drug was discovered prior to the solving of the crystal structure of AChE; therefore, there was no known information about the spatial conformation of the AChE active site residues or the mechanism of inhibitor binding to guide the design of donepezil at the time of the drug's discovery. Rather, a brute force structure-activity relationship (SAR) effort beginning with the discovery of a benzylpiperidine compound that was observed to inhibit AChE in 1990 is what ultimately lead to the identification and eventual approval of donepezil as a drug after more than a decade of research.

In 1999, the crystal structure of *Torpedo californica* AChE (TcAChE) with donepezil bound in the active site was reported by Sussman et al. This report revealed the key interaction between donepezil and the active site of AChE that can be attributed to the high affinity of the drug for the enzyme. The flexibility of the piperidine backbone via rotatable methylene linkers is crucial to allowing for favorable interaction between active site residues and the drug. The indanone moiety, which sits in the wide funnel-like entrance to the gorge, stacks against the indole ring of Trp279 by means of a π-π interaction, as well as forms a water-mediated hydrogen bond between one of the methoxy substituents and Glu185. In the middle are of the gorge, there is a strong cation-π interaction observed between the protonated piperidine ring of donepezil and Phe330. At the bottom of the gorge, the benzyl group of donepezil displays π-π stacking interactions with Trp84.

A generation of donepezil inspired 2-methylamino-3-hydroxypyridine QMPs that are anticipated to be less potent inhibitors of AChE was proposed in Scheme 5.

Scheme 5: Proposed structures for second-generation donepezil inspired 2-methyamino-3-hydroxypyridines.

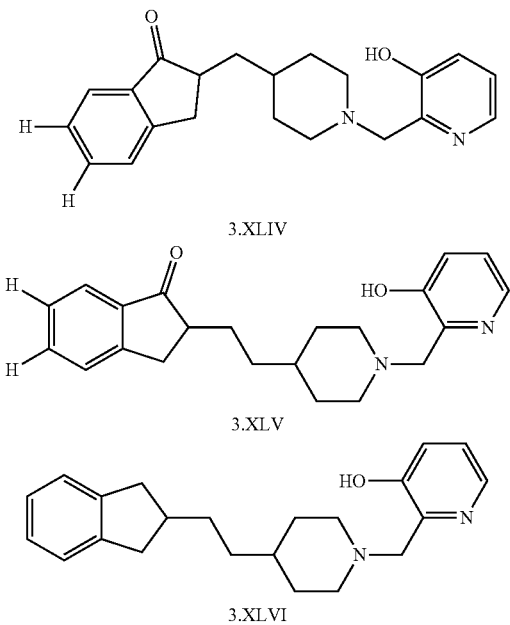

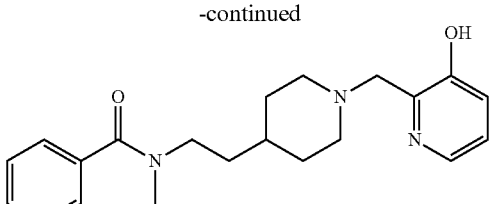

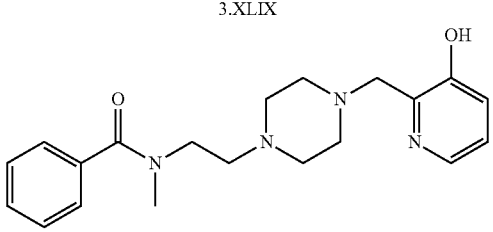

The methoxy substituents of donepezil are known to make a favorable interaction with Glu185 of AChE via a water-mediated hydrogen bond. SAR studies show that the desmethoxy donepezil derivative is a 25-fold less potent inhibitor of AChE than donepezil. The synthesis for compound 3.XLIV used 1-indanone in place of 5,6-dimethoxyindanone.

An alternative synthetic route was conceived wherein an aldol condensation between 1-indanone and piperidine aldehyde 3.XLXII would alleviate the need for the stubborn pyridine hydrogenation. The forward synthesis began with the Boc deprotection of isonipecotic acid to give a Boc-amine. This amine was converted to Weinreb amide 3.LIV via EDC coupling, which was sequentially reduced to an aldehyde with lithium aluminum hydride. The aldehyde was then subjected to an aldol condensation with 1-indanone to afford α,β-unsaturated ketone 3.LV, which was hydrogenated with palladium on carbon to afford 3.LVI. TFA Boc deprotection liberated the free amine 3.LVII, which was then reacted with 2-bromomethyl-3-hydroxypyridine to yield the desired final product 3.XLIV by means of nucleophilic substitution.

The next effort was towards the synthesis of compound 3.XLV, which differs in structure from 3.XLIV by the addition of one methylene unit between the indanone moiety and the pyridine ring. This feature is designed to add conformational flexibility to the alkylator. The proposed synthesis of this compound would capitalize on the product of an aldol reaction between 1-indanone and aldehyde 3.LVIII. Aldehyde 3.LVIII was proposed to come from a Horner-Wadsworth-Emmons (HWE) reaction between commercially available N-Boc-4-piperidone and triethyl phosphonoacetate.

The HWE reaction to afford ester 3.LIX proceeded cleanly in high yield. The α,β-unsaturated double bond was hydrogenated under 1 atm $H_2$ with palladium on carbon to give the saturated compound 3.LX. This ester was then reduced to aldehyde 3.LVIII by means of diisobutylaluminum hydride. A crossed aldol condensation between the resulting aldehyde and 1-indanone under basic conditions provided intermediate 2.LXI in 43% yield after purification. Attempted hydrogenation of 3.LXI by means of palladium catalysts (Pd/C or Pd(OH)$_2$) lead to the desired saturation of the double bond, but also the undesired reduction of the benzylic carbonyl to give indane 3.LXII. A similar result was observed by Renou and coworkers where they saw conversion of the indanone carbonyl of 3.LXIII to a methylene group affording indane compound 3.LXIV under the same conditions during their synthesis of donepezil-based 2-pyridine aldoximes. However, this observation ultimately lead these researchers to the discovery of 2-pyridine aldoxime 3.XLI, which was reported to be quite effective in the reactivation of both VX and paraoxon inhibited AChE (observed reactivation rates of inhibited AChE: kr2=1.8 and 1.5 min-1 min-1 respectively).

Indane 3.LXII was converted to the final QMP realkylator 3.XLVI by TFA deprotection of the Boc amine followed by nucleophilic substitution with 2-bromomethyl-3-hydroxy-pyridine.

The alkylator 3.XLIX was proposed based on an open-chain benzyl piperidine AChE inhibitor discovered by the Eisai company prior to the discovery of the more potent indanone, donepezil. This compound has the benefits of increased rotational freedom due to the extended methylene chain between the piperidine and the aromatic amide, as well the increased flexibility imparted by opening the indanone ring. The synthesis of 3.XLIX would begin with the common intermediate 3.LX (Scheme 6).

Scheme 6: Synthesis leading to the isolation of alkylator 3.XLVI

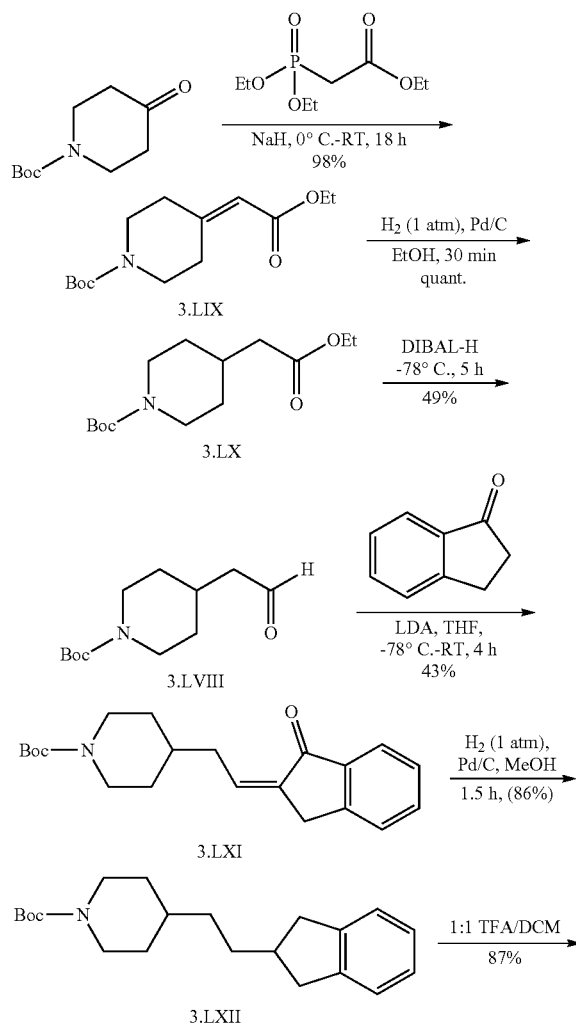

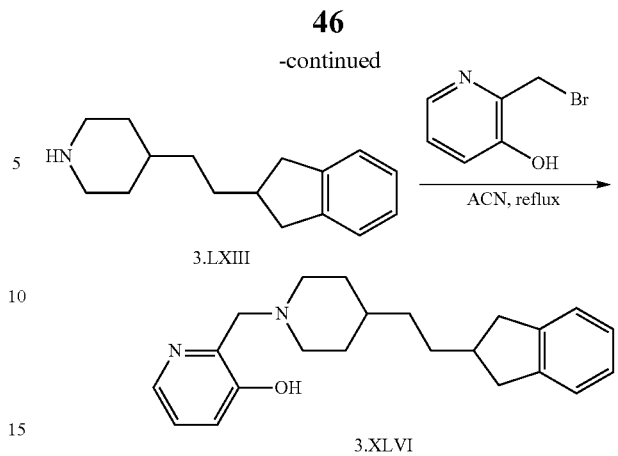

3.LX was saponified to give carboxylic acid 3.LXV, which was then treated with thionyl chloride to generate an acid chloride intermediate, which was subsequently converted to methylamide 3.LXVI with an aqueous methylamine solution. This amide was reduced to amine 3.LXIV with lithium aluminum hydride, and then further converted to amide 3.LXVII with benzoyl chloride. The Boc-protected piperidine was then deprotected with TFA to liberate the free amine 3.LXV, which was converted to the final product 3.XLIX by a substitution reaction analogous to those previously described with 2-bromomethyl-3-hydroxypyridine.

The final targeted donepezil inspired 2-methylamino-3-hydroxypyridine QMP realkylator, 3.XLVIII, differs from the synthesized compound 3.XLIX in that the piperidine ring is replaced with a piperazine. This structural difference was designed to simplify the overall synthesis and allow for quick structural variation of the amide portion by the use of various acid chlorides and amino alcohols in the initial step. This would allow a rapid library synthesis for SAR purposes should the initial compound show any realkylation ability towards aged AChE. 3.XLVIII was envisioned to come from amine 3.LXVI, which would by synthesized form the activation and displacement of the alcohol functional group of 3.LXVII with 1-Boc-piperazine (Scheme 7).

The forward synthesis include benzoyl chloride and 2-(methylamino)-1-ethanol were coupled to provide amide 3.LXVII. This alcohol was then converted to an alkylchloride via thionyl chloride. Following, the chloride was displaced with 1-boc-piperazine to afford 3.LXVI. Boc deprotection with TFA and substitution on 2-bromomethyl-3-hydroxy pyridine yielded the final compound 3.XLVIII.

Scheme 7: Forward synthetic of realkylator 3.XLVIII

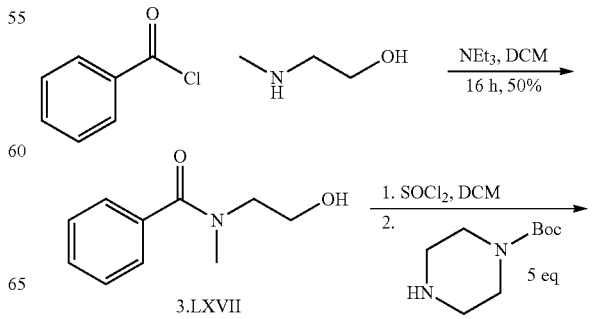

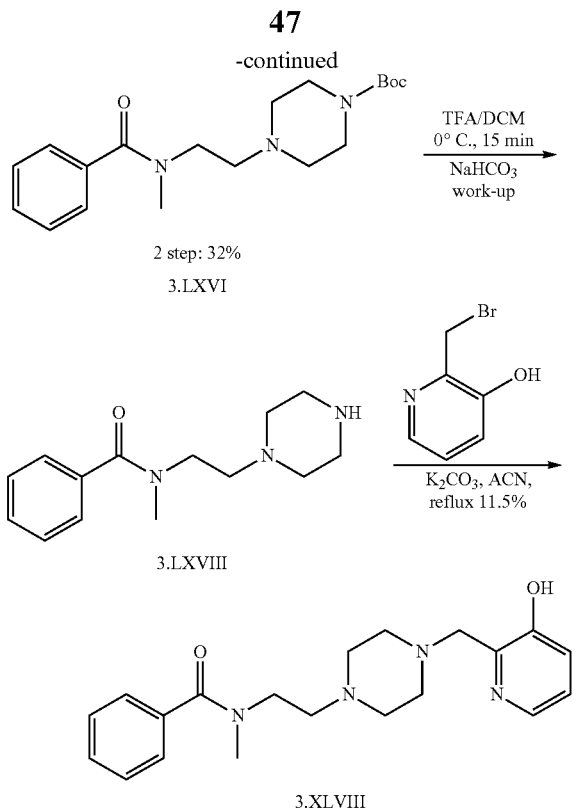

2 step: 32%
3.LXVI

3.LXVIII

3.XLVIII

Example procedure for synthesis of 3-hydroxypyridyl QMPs (C1-C13): 3-hydroxypyridine (500.2 mg, 5.32 mmol, 1.0 equiv.) was dissolved in water (10 mL). To this suspension was added a 37% wt formaldehyde solution (175.6 mg, 5.85 mmol, 1.1 equiv.) and N-methylethylamine (0.50 mL, 5.85 mmol, 1.1 equiv.). (18) The resulting suspension was heated to reflux for 4 h. The solution was cooled to room temperature and extracted 3 times with dichloromethane (DCM). The organic layer was dried over anhydrous sodium sulfate ($Na_2SO_4$), and DCM was removed under reduced pressure. The isolated product was a brown oil* (666.3 mg, 75%). Products isolated as oils were further protonated with 1M oxalic acid in diethyl ether or HCl in methanol (1 equiv.) for Ellman's assay-based screening.

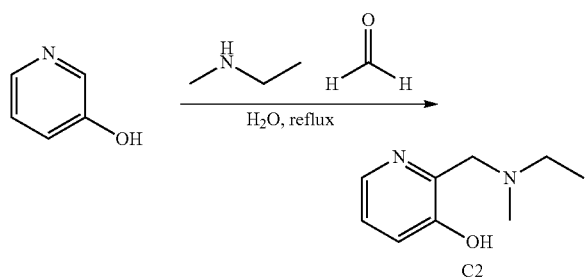

Synthesis of 2-chloro-5-(pyrrolidin-1-ylmethyl)pyridine: Pyrrolidine (0.67 mL, 8.00 mmol, 2.0 equiv.), 2-chloro-5-(chloromethyl)pyridine (0.648 g, 4.00 mmol, 1.0 equiv.), potassium carbonate (0.553 g, 4.00 mmol, 1.0 equiv.), and acetonitrile (10 mL) were combined and heated to reflux for 3.5 h and then allowed to cool to room temperature. Water (20 mL) was added and the solution was extracted with chloroform (3×30 mL). The organic layers were collected and dried with $Na_2SO_4$, and the solvent was evaporated under reduced pressure at 50° C. to yield 2-chloro-5-(pyrrolidin-1-ylmethyl)pyridine as a red oil (0.830 g, 4.22 mmol, 100%). 2-Chloro-5-(pyrrolidin-1-ylmethyl)pyridine: $^1H$ NMR ($CDCl_3$, 400 MHz) δ=8.32 (m, 1H), 7.67 (m, 1H), 7.29 (m, 1H), 3.60 (s, 2H), 2.50 (m, 4H), 1.80 (m, 4H).

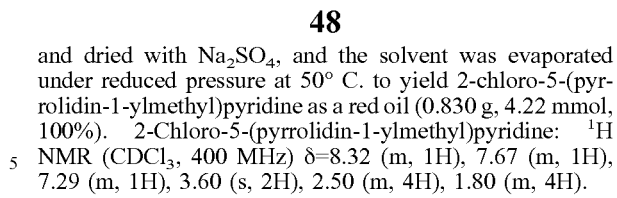

Synthesis of 5-(pyrrolidin-1-ylmethyl)pyridine-2-ol (M1): 2-Chloro-5-(pyrrolidin-1-ylmethyl)pyridine (0.150 g, 0.763 mmol, 1 eq.) and 3 M HCl (0.763 mL, 2.29 mmol, 3.0 eq.) were combined and refluxed for 6 h and then allowed to cool to room temperature. The solution was neutralized with potassium carbonate and water was evaporated under reduced pressure at 65° C. The solution was then suspended in ethanol and a filtrate was collected. The solvent was evaporated under reduced pressure at 40° C. to yield 5-(pyrrolidin-1-ylmethyl)pyridine-2-ol as a brown oil (0.120 g, 0.671 mmol, 88%).

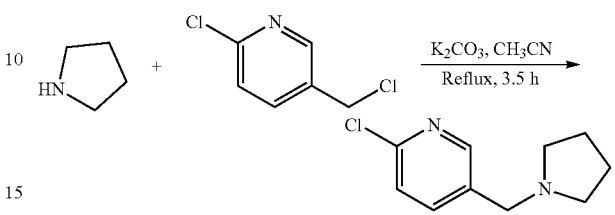

Synthesis of 4-chloronicotinaldehyde: Saturated $NaHCO_3$ was added to a suspension of 4-chloropyridinium hydrochloride (10 g, 67 mmol) in diethyl ether (100 mL). The biphasic mixture was stirred for 1 h, then separated. The aqueous layer was extracted with diethyl ether (3×50 mL). Combined organic layers were dried over $Na_2SO_4$ and concentrated. The resulting oil was purified by distillation to afford pure 4-chloropyridine. A −78° C. solution of 2 M lithium diisopropylamide (LDA) in heptane/tetrahydrofuran (THF) (19 mL, 38.04 mmol, 1.2 equiv.) was diluted in THF (60 mL) and treated with the dropwise addition of a solution of 4-chloropyridine (3.6 g, 31.7 mmol, 1 equiv.) in THF (10 mL). The mixture was slowly warmed to −40° C. and stirred 1 h before returning to −78° C. Dimethylformamide (DMF, 3.0 mL, 38.04 mmol, 1.2 equiv.) was added, and the reaction was stirred 2 h at −78° C., then warmed to RT as ice bath expired and stirred 16 h. The reaction was cooled to −10° C. and quenched with sat. $NH_4Cl$ (5 mL). The reaction was diluted with water and extracted with ethyl acetate. The organic layers were washed with brine, dried over $Na_2SO_4$ and concentrated. The crude red oil was purified by silica gel chromatography (30% EtOAc/hexanes) to afford the title compound as a yellow tinted oil which crystalized to clear needles under argon (1.6 g, 36% yield). Spectra matched the literature reports. $^1$H-NMR (400 MHz, $CDCl_3$): δ=10.51 (s, 1H); 9.05 (s, 1H); 8.68 (d, J=5.76 Hz, 1H); 7.43 (d, J=5.4 Hz, 1H).

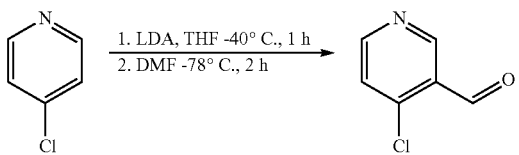

Synthesis of 4-chloro-3-(pyrrolidin-1-ylmethyl)pyridine (M3): A solution of 4-chloronicotinaldehyde (100 mg, 0.7 mmol, 1 equiv.) in 1,2-dichloroethane was treated with pyrrolidine (0.06 mL, 0.77 mmol, 1.1 equiv.) followed by sodium triacetoxyborohydride (NaBH(OAc)$_3$, 207 mg, 0.98 mmol, 1.4 equiv.) and acetic acid (AcOH, 0.04 mL). The reaction mixture was stirred for 1.5 h, then quenched with excess saturated NaHCO$_3$ solution and extracted with DCM. The organic layers were washed with brine, dried over Na$_2$SO$_4$ and concentrated to afford the title product (139 mg, 100%).

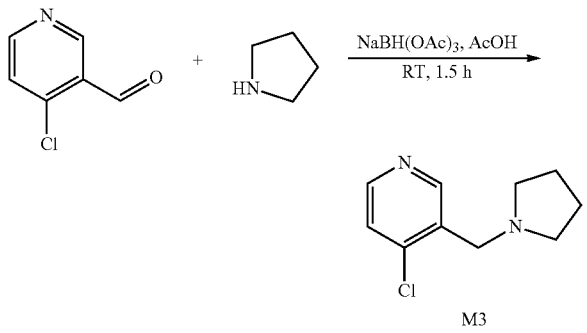

Synthesis of 3-chloro-2-(chloromethyl)quinolone: 2-aminobenzaldehyde (0.250 g, 0.206 mmol, 1 equiv.), 1,3-dichloroacetone (0.262 g, 0.206 mmol, 1 equiv.), and p-tosylic acid monohydrate (0.393 g, 0.206 mmol, 1 equiv.) were mixed and heated at 110° C. for 1 h while monitored with TLC (hexane:ethyl acetate 10:1). The reaction was cooled, and water (5 mL) was added. The resulting mixture was neutralized to pH=10 with NaOH (10%, 0.8 mL). The reaction was extracted with DCM (3×10 mL). The organic extracts were combined and dried with Na$_2$SO$_4$. The residual solvent was evaporated to yield the crude solid that was purified by column chromatography (hexane:ethyl acetate 10:1) to give 3-chloro-2-(chloromethyl)quinoline as a white solid (0.17 g, 38%). $^1$H NMR (CDCl$_3$, 400 MHz): δ=8.23 (s, 1H), 8.12 (dd, J$_1$=8.1 Hz, J$_2$=1.8 Hz, 1H), 7.76 (dd, J$_1$=8.2 Hz, J$_2$=1.6 Hz, 1H), 7.71 (td, J$_1$=7.9 Hz, J$_2$=1.5 Hz, 1H), 7.60 (td, J$_1$=8.2 Hz, J$_2$=1.6 Hz, 1H), 4.99 (s, 2H) ppm; $^{13}$C NMR (CDCl$_3$, 400 MHz): δ=160.3, 146.1, 133.3, 130.1, 128.7, 128.3, 127.5, 127.2, 126.9, 39.1 ppm

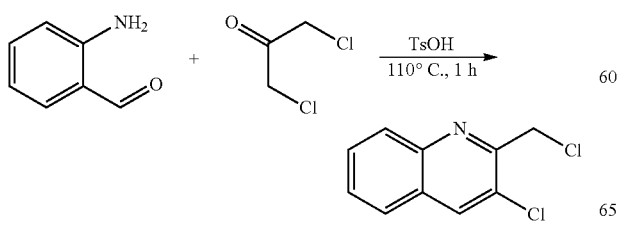

Characterizations of candidate realkylators:
2-((dimethylamino)methyl)pyridin-3-ol (C1)

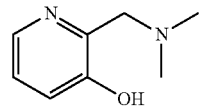

Pale orange solid, 80% yield. $^1$H NMR (DMSO, 400 MHz): δ=7.93-7.94 (dd, J$_1$=1.52 Hz, J$_2$=4.55 Hz, 1H), 7.12-7.15 (dd, J$_1$=4.55 Hz, J$_2$=8.16 Hz, 1H), 7.07-7.09 (dd, J$_1$=1.52 Hz, J$_2$=8.16 Hz, 1H), 3.76 (s, 2H), 2.28 (s, 6H); $^{13}$C NMR (DMSO, 100 MHz): δ=153.67, 143.42, 139.19, 123.38, 122.02, 63.26, 44.30; HRMS (ESI-orbitrap): m/z calcd for C$_8$H$_{12}$N$_2$O+H$^+$: 153.1022, found: 153.1021.

2-((ethyl(methyl)amino)methyl)pyridin-3-ol (C2)

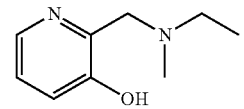

Brown oil, 75% yield. $^1$H NMR (DMSO, 400 MHz): δ=8.11-8.13 (dd, J$_1$=1.46 Hz, J$_2$=4.46 Hz, 1H), 7.35-7.37 (dd, J$_1$=1.42 Hz, J$_2$=8.34 Hz, 1H), 7.29-7.33 (dd, J$_1$=4.48 Hz, J$_2$=8.16 Hz, 1H), 4.37 (s, 2H), 3.15-3.21 (q, J=7.27 Hz, 2H), 2.78 (s, 3H), 1.24-1.27 (t, J=7.26 Hz, 3H); $^{13}$C NMR (DMSO, 100 MHz): δ=152.34, 139.62, 138.28, 124.98, 122.99, 53.72, 50.80, 39.86, 9.08; HRMS (ESI-orbitrap): m/z calcd for C$_9$H$_{14}$N$_2$O+H$^+$: 167.1179, found: 167.1182.

2-((methyl(propyl)amino)methyl)pyridin-3-ol (C3)

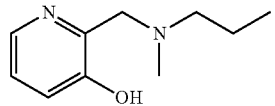

Brown oil, 57% yield $^1$H NMR (DMSO, 400 MHz): δ=8.07-.09 (m, J$_1$=1.62 Hz, J$_2$=4.34 Hz, 1H), 7.30-7.33 (dd, J$_1$=1.64 Hz, J$_2$=8.24 Hz, 1H), 7.26-7.29 (dd, J$_1$=4.36 Hz, 0.12=8.28 Hz, 2H), 4.27 (s, 2H), 2.93-2.97 (t, J=8.04 Hz, 2H), 2.69 (s, 3H), 1.65-1.71 (m, J=7.68 Hz, 2H), 0.87-0.90 (t, J=7.34 Hz, 3H); $^{13}$C NMR (DMSO, 100 MHz): δ=152.67, 139.50, 124.67, 122.81, 57.36, 55.71, 40.62, 17.43, 10.89; HRMS (ESI-orbitrap): m/z calcd for C$_{10}$H$_{16}$N$_2$O+H$^+$: 181.1335, found: 181.1335.

2-((isopropyl(methyl)amino)methyl)pyridin-3-ol (C4)

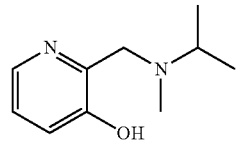

Brown oil, 33% yield. ¹H NMR (DMSO, 400 MHz): δ=8.12-8.13 (dd, J₁=1.46 Hz, J₂=4.48 Hz, 1H), 7.36-7.38 (dd, J₁=1.48 Hz, J₂=8.28 Hz, 1H), 7.30-7.33 (dd, J₁=4.48 Hz, J₂=8.28 Hz, 1H), 4.31 (s, 2H), 3.50-3.57 (m, J=6.64 Hz, 1H), 2.72 (s, 3H), 1.29-1.30 (d, J=6.64 Hz, 6H); ¹³C NMR (DMSO, 100 MHz): δ=152.41, 139.58, 138.37, 125.03, 123.04, 56.71, 51.13, 36.80, 16.15; HRMS (ESI-orbitrap): m/z calcd for $C_{10}H_{16}N_2O+H^+$: 181.1335, found: 181.1334.

2-((butyl(methyl)amino)methyl)pyridin-3-ol (C5)

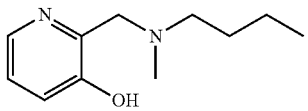

Yellow solid, 82% yield. ¹H NMR (DMSO, 400 MHz): δ=8.10-8.11 (dd, J₁=1.82 Hz, J₂=4.14 Hz, 1H), 7.30-7.31 (m, 2H), 4.32 (2.06), 3.02-3.06, (t, J=8.03 Hz, 2H), 2.74 (s, 3H), 1.68-1.70 (m, J=7.83 Hz, 2H), 1.27-1.32 (m, J=7.43 Hz, 2H), 0.87-0.90 (t, J=7.36 Hz, 3H); ¹³C NMR (DMSO, 100 MHz): δ=153.06, 140.04, 139.20, 125.35, 123.42, 55.95, 55.4, 41.10, 26.14, 19.81, 13.95; HRMS (ESI-orbitrap): m/z calcd for $C_{11}H_{18}N_2O+H^+$: 195.1492, found: 194.1495.

2-((isobutyl(methyl)amino)methyl)pyridin-3-ol (C6)

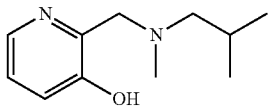

Yellow solid, 57% yield. ¹H NMR (DMSO, 400 MHz): δ=8.06-8.08 (dd, J₁=1.98 Hz, J₂=4.02 Hz 1H), 7.27-7.28 (m, 2H), 4.22 (s, 2H), 2.76-2.78 (d, J=7.16 Hz, 2H), 2.65 (s, 3H), 2.03-2.12 (m, J=6.78 Hz, 1H), 0.92-0.94 (d, J=6.65 Hz, 6H); ¹³C NMR (DMSO, 100 MHz): δ=153.30, 140.02, 125.13, 123.25, 63.94, 57.53, 42.09, 24.60, 20.66; HRMS (ESI-orbitrap): m/z calcd for $C_{11}H_{18}N_2O+H^+$: 195.1492, found: 194.1494.

2-((diethylamino)methyl)pyridin-3-ol (C7)

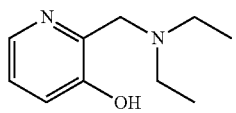

Orange solid, 75% yield. ¹H NMR (DMSO, 400 MHz): δ=11.25 (bs, 1H), 9.92 (bs, 1H), 8.16-8.18 (dd, J₁=1.30 Hz, J₂=4.70 Hz, 1H), 7.57-7.59 (dd, J₁=1.24 Hz, J₂=8.32 Hz, 1H), 7.38-7.41 (dd, J₁=4.70 Hz, J₂=8.34 Hz 1H), 4.38 (s, 2H), 3.15-3.21 (q, J=7.23 Hz, 4H), 1.24-1.28 (t, J=7.24 Hz, 6H); ¹³C NMR (DMSO, 100 MHz): δ=153.07, 138.78, 137.30, 125.54, 124.43, 49.54, 47.65, 8.73; HRMS (ESI-orbitrap): m/z calcd for $C_{10}H_{16}N_2O+H^+$: 181.1335, found: 181.1334.

2-(pyrrolidin-1-ylmethyl)pyridin-3-ol (C8)

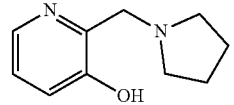 [SMILES: Oc1cccnc1CN1CCCC1]

Light brown solid, 88% yield.; ¹H NMR (DMSO, 400 MHz): δ=11.01 (bs, 1H), 10.31 (bs, 1H), 8.12-8.14 (dd, J₁=1.34 Hz, J₂=4.66 Hz, 1H), 7.47-7.49 (dd, J₁=1.32 Hz, J₂=8.28 Hz, 1H), 7.33-7.36 (dd, J₁=4.68 Hz, J₂=8.32 Hz, 1H), 4.48 (s, 2H), 3.36 (bs, 4H), 1.94-1.97 (m, 4H); ¹³C NMR (DMSO, 100 MHz): δ=0.152.85, 139.21, 138.79, 125.66, 124.35, 54.33, 53.23, 23.18; HRMS (ESI-orbitrap): m/z calcd for $C_{10}H_{14}N_2O+H^+$: 179.1179, found: 179.1182.

2-((3,3-difluoropyrrolidin-1-yl)methyl)pyridin-3-ol (C9)

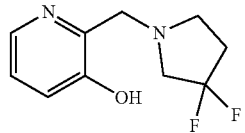 [SMILES: Oc1cccnc1CN1CCC(F)(F)C1]

Tan solid, 27% yield. ¹H NMR (CDCl₃, 400 MHz): δ=7.99-8.00 (t, J=3.02 Hz, 1H), 7.09-7.10 (d, J=2.92 Hz, 2H), 4.01 (s, 2H), 3.00-3.06 (t, J=12.7 Hz, 2H), 2.87-2.91 (t, J=7.15 Hz, 2H), 2.31-2.38 (m, 2H); ¹³C NMR (DMSO, 100 MHz): δ=152.63, 144.54, 139.90, 123.93, 122.58, 61.38, 55.85, 35.63, 19.39; ¹⁹F NMR (CDCl₃, 376 MHz): δ=−93.050−−92.961 (m); HRMS (ESI-orbitrap): m/z calcd for $C_{10}H_{12}N_2OF_2+H^+$: 215.0990, found: 215.0985.

2-(piperidin-1-ylmethyl)pyridin-3-ol (C10)

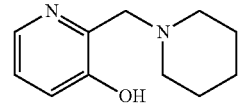 [SMILES: Oc1cccnc1CN1CCCCC1]

Light brown solid, 95% yield. ¹H NMR (DMSO, 400 MHz): δ=11.18 (bs, 1H), 10.01 (bs, 1H), 8.18-8.19 (dd, J₁=1.26 Hz, J₂=4.70 Hz, 1H), 7.55-7.57 (d, J=8.24 Hz, 1H), 7.39-7.42 (dd, J₁=4.54 Hz, J₂=8.14 Hz, 1H), 4.38 (s, 2H), 3.23 (bs, 4H), 1.77-1.81 (m, J=5.84 Hz, 4H), 1.53 (bs, 2H); ¹³C NMR (DMSO, 100 MHz): δ=0.153.80, 137.80, 135.59, 126.04, 125.79, 53.49, 52.65, 22.27, 21.07; HRMS (ESI-orbitrap): m/z calcd for $C_{11}H_{16}N_2O+H^+$: 193.1335, found: 193.1333.

2-(piperazin-1-ylmethyl)pyridin-3-ol (C11)

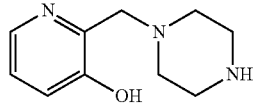 [SMILES: Oc1cccnc1CN1CCNCC1]

Yellow solid, 86% yield. ¹H NMR (CD₃OD, 400 MHz): δ=8.32-8.34 (dd, J₁=1.22 Hz, J₂=5.58 Hz, 1H), 7.90-7.92 (dd, J₁=1.24 Hz, J₂=8.52 Hz, 1H), 7.80-7.83 (dd, J₁=5.58 Hz, J₂=8.50 Hz, 1H), 4.13 (s, 2H), 3.42-3.45 (m, 4H), 3.01-3.03 (m, 4H); ¹³C NMR (CD₃OD, 100 MHz): δ=154.73, 140.51, 132.48, 129.92, 126.34, 52.93, 49.41, 42.97; HRMS (ESI-ToF): m/z calcd for $C_{10}H_{15}N_2O+H^+$: 194.1288, found: 194.1288

2-(morpholinomethyl)pyridin-3-ol (C12)

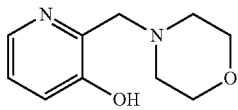

Light brown solid, 78% yield. ¹H NMR (DMSO, 400 MHz): δ=10.84-11.26 (m, 2H), 8.15-8.17 (m, 1H), 7.49-7.52 (m, 1H), 7.36-7.41 (m, 1H), 4.46 (s, 2H), 3.86-3.88 (t, 4H), 3.32-3.34 (t, 4H); ¹³C NMR (DMSO, 100 MHz): δ=152.87, 139.01, 136.91, 125.34, 123.97, 63.10, 54.44, 51.62; HRMS (ESI-orbitrap): m/z calcd for $C_{10}H_{14}N_2O_2+H^+$: 195.1128, found: 195.1126.

2,2'-(piperazine-1,4-diylbis(methylene))bis(pyridin-3-ol) (C13)

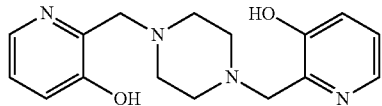 [SMILES: Oc1cccnc1CN1CCN(Cc2ncccc2O)CC1]

White solid, 38% yield. ¹H NMR (DMSO, 400 MHz): δ=11.29 (bs, 2H), 8.17-8.19 (dd, J₁=1.26 Hz, J₂=4.86 Hz, 2H), 7.62-7.64 (dd, J₁=1.16 Hz, J₂=8.36 Hz, 2H), 7.45-7.48 (dd, J₁=4.88 Hz, J₂=8.32 Hz, 2H), 4.33 (s, 4H), 3.39 (s, 8H); ¹³C NMR (DMSO, 100 MHz): δ=153.25, 138.04, 137.51, 125.56, 125.27, 53.50, 49.02; HRMS (ESI-orbitrap): m/z calcd for $C_{16}H_{20}N_4O_2+H^+$: 301.1659, found: 301.1652.

5-(pyrrolidin-1-ylmethyl)pyridin-2-ol (M1)

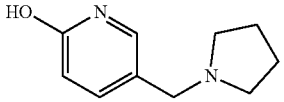 [SMILES: Oc1ccc(CN2CCCC2)cn1]

Brown oil, 88%. ¹H NMR (DMSO, 400 MHz): δ=10.96 (bs, 1H), 7.25 (d, J=1.44 Hz, 1H), 7.04-7.06 (m, J=1.60 Hz, 7.96 Hz, 1H), 6.95-6.97 (d, J=7.92 Hz, 1H), 6.06 (s, 2H), 4.21 (s, 2H), 3.00 (bs, 3H), 1.89-1.96 (bs, 5H); ¹³C NMR (DMSO, 100 MHz): δ=148.35, 147.86, 124.99, 111.01, 108.80, 101.84, 56.85, 52.74, 22.98. HRMS (ESI-orbitrap): m/z calcd for $C_{10}H_{14}N_2O+H^+$: 179.1179, found: 179.1182.

3-(pyrrolidin-1-ylmethyl)pyridin-2-ol (M2)

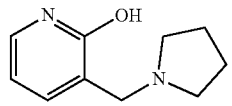 [SMILES: Oc1ncccc1CN1CCCC1]

White solid, 55% yield. ¹H NMR (CDCl₃, 400 MHz): δ=7.46-7.48 (m, 1H), 7.29-7.35 (m, 1H), 6.55-6.59 (dd, J₁=4.32 Hz, J₂=9.16 Hz, 1H), 6.14-6.19 (m, 1H), 4.86-4.87 (d, J=5.32 Hz, 2H), 2.72-2.74 (m, 4H), 1.78-1.80 (m, 4H); ¹³C NMR (DMSO, 100 MHz): δ=163.17, 139.45, 136.99, 121.25, 105.28, 66.35, 51.34, 51.14, 23.91, 23.71; HRMS (ESI-orbitrap): m/z calcd for $C_{10}H_{14}N_2O+H^+$: 179.1179, found: 179.1179.

4-chloro-3-(pyrrolidin-1-ylmethyl)pyridine (M3)

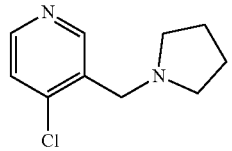 [SMILES: Clc1ccncc1CN1CCCC1]

White solid, 36% yield. ¹H-NMR (DMSO, 400 MHz), δ: 8.77 (s, 1H), 8.55-8.56 (d, J=5.36 Hz, 1H); 7.64-7.65 (d, J=5.36 Hz, 1H); 4.32 (s, 2H); 3.10 (bs, 4H); 1.87-1.91 (m, 4H); ¹³C NMR (DMSO, 100 MHz): δ=163.05, 152.86, 143.72, 127.62, 124.69, 53.34, 51.89, 22.60; HRMS (ESI-ToF): m/z calcd for $C_{10}H_{13}N_2Cl+H^+$: 197.0846, found: 197.0852.

2-methoxy-4-(pyrrolidin-1-ylmethyl)phenol (M4)

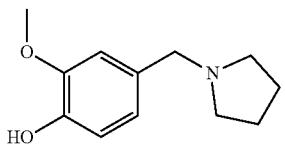

Orange solid. ¹H NMR (DMSO, 400 MHz): δ=10.81 (bs, 1H), 9.29 (s, 1H), 7.28 (d, J=1.88 Hz, 1H), 6.91-6.93 (dd, J₁=1.94 Hz, J₂=8.02 Hz, 1H), 6.79-6.81 (d, J=8.00 Hz, 1H), 4.18 (s, 2H), 3.80 (s, 3H), 3.28 (bs, 2H), 3.00 (bs, 2H), 1.99 (bs, 2H), 1.88 (bs, 2H); ¹³C NMR (DMSO, 100 MHz): δ=148.01, 147.79, 123.64, 122.58, 115.73, 114.99, 57.22, 56.12, 52.67, 23.01; HRMS (ESI-orbitrap): m/z calcd for $C_{12}H_{17}NO_2+H^+$: 208.1332, found: 208.1328.

4-(pyrrolidin-1-ylmethyl)quinolin-3-ol (M5)

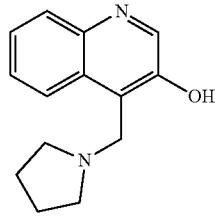 [SMILES: Oc1cnc2ccccc2c1CN1CCCC1]

Tan solid, 82% yield. $^1$H NMR (D$_2$O, 400 MHz): δ=8.34 (s, 1H), 7.99-8.01 (d, J=8.48 Hz, 1H), 7.82-7.84 (d, J=8.28, 1H), 7.74-7.78 (m, 1H), 7.59-7.63 (t, J=7.62 Hz), 4.77 (s, 1H), 3.51 (bs, 2H), 2.07-2.11 (m, 4H); $^{13}$C NMR (DMSO, 100 MHz): δ=149.54, 144.53, 136.24, 136.08, 130.73, 128.36, 128.13, 127.80, 127.42, 125.68, 56.34, 54.58, 23.05. HRMS (ESI-orbitrap): m/z calcd for C$_{14}$H$_{16}$N$_2$O+H$^+$: 229.1335, found: 229.1334.

4-(pyrrolidin-1-ylmethyl)quinolin-2-ol (M6)

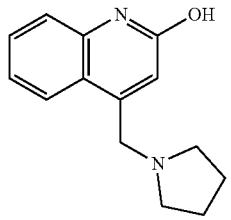 [SMILES: Oc1cc(CN2CCCC2)c2ccccc2n1]

Off-white solid, 65% yield. $^1$H NMR (D$_2$O, 400 MHz): δ=7.76-7.78 (m, 1H), 7.58-7.62 (m, 1H), 7.32-7.37 (m, 2H), 6.72 (s, 1H), 4.47 (s, 2H), 3.23-3.26 (m, 4H), 195-1.99 (m, 4H). $^{13}$C NMR (DMSO, 100 MHz): δ=160.83, 141.20, 139.05, 130.97, 124.66, 123.88, 121.91, 117.42, 115.80, 53.89, 52.49, 22.64. HRMS (ESI-orbitrap): m/z calcd for C$_{14}$H$_{16}$N$_2$O+H$^+$: 229.1335, found: 229.1340.

3-(pyrrolidin-1-ylmethyl)quinolin-2-ol (M7)

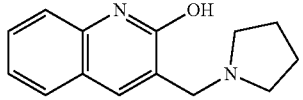 [SMILES: Oc1nc2ccccc2cc1CN1CCCC1]

Yellow solid, 79% yield. $^1$H NMR (DMSO, 400 MHz): δ=8.39-8.41 (ddd, J$_1$=0.92 Hz, J$_2$=1.76 Hz, J$_3$=4.84 Hz, 1H), 7.65-7.70 (dd, J$_1$=1.82 Hz, J$_2$=7.65 Hz, 1H), 7.33-7.35 (d, J=7.80 Hz, 1H), 7.15-7.19 (ddd, J$_1$=1.16 Hz, J$_2$=4.88 Hz, J$_3$=7.48 Hz, 1H), 3.63 (s, 2H), 3.29-3.32 (t, J=6.76 Hz, 1H), 3.16-3.19 (t, J=6.86 Hz, 1H), 2.40-2.43 (m, 4H, overlapped with solvent), 1.85 (s, 1H), 1.75-1.82 (m, 1H), 1.67-1.72 (m, 1H), 1.61-1.65 (m, J=3.35 Hz, 4H); $^{13}$C NMR (DMSO, 100 MHz): δ=0.159.66, 149.11, 136.92, 122.95, 122.45, 61.81, 54.08, 23.68. HRMS (ESI-orbitrap): m/z calcd for C$_{14}$H$_{16}$N$_2$O+H$^+$: 229.1335, found: 229.1333.

2-(pyrrolidin-1-ylmethyl)pyridine (M8)

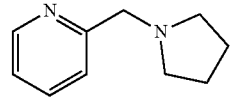 [SMILES: c1ccc(CN2CCCC2)nc1]

Brown oil, 82% yield. $^1$H NMR (CDCl$_3$, 400 MHz): δ=8.43-8.45 (ddd, J$_1$=0.91 Hz, J$_2$=1.75 Hz, J$_3$=4.89 Hz, 1H), 7.53-7.57 (td, J$_1$=1.82 Hz, J$_2$=7.67 Hz, 1H), 7.31-7.33 (d, J=7.8 Hz, 1H), 7.14-7.08 (ddd, J$_1$=1.15 Hz, J$_2$=4.89 Hz, J$_3$=7.49 Hz, 1H), 3.71 (s, 2H), 2.52 (t, J=6.78 Hz, 4H), 1.70-1.73 (m, J=3.40 Hz, 4H). $^{13}$C NMR (CDCl$_3$, 100 MHz): δ=158.82, 149.00, 136.45, 123.08, 121.97, 61.95, 54.13, 23.46; HRMS (ESI-orbitrap): m/z calcd for C$_{14}$H$_{16}$N$_2$O+H$^+$: 229.1335, found: 229.1340.

1-(benzo[d][1,3]dioxol-5-ylmethyl)pyrrolidine (M9)

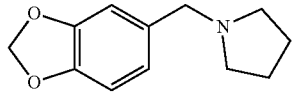 [SMILES: c1cc2c(cc1CN1CCCC1)OCO2]

Off-white solid. $^1$H NMR (D$_2$O, 400 MHz): δ=6.87-6.94 (m, 3H), 5.95 (s, 2H), 4.18 (s, 2H), 3.22 (bs, 4H), 1.97 (bs, 4H). $^{13}$C NMR (DMSO, 100 MHz): δ=162.32, 143.14, 124.78, 53.57, 53.08, 52.43, 23.10, 23.01; HRMS (ESI-orbitrap): m/z calcd for C$_{12}$H$_{15}$NO$_2$+H$^+$: 206.1176, found: 206.1171.

Aging of AChE by PiMP for Screening and Kinetics: All reactions with AChE below were performed at 37° C., unless otherwise noted. Electric eel AChE, bovine serum albumin (BSA) and DFP were purchased from Sigma Aldrich, USA. The buffer was 200 min sodium phosphate without NaCl added, either at pH 7.0 or 8.0.

For preparation of methylphosphonate-aged AChE, to 37.5 μL of buffer at pH 7.0 (containing 1 g/L BSA and 0.02% NaN$_3$ to stabilize the enzyme and prevent bacterial contamination), AChE (7.5 μL, 4 g/L in 1:1 glycerin/water) and PiMP (2.5 μL, 0.2 min in 2% acetonitrile) were added. After reacting for 2 h, the solution was treated with a Sephadex G-25 spin column (0.1 g of superfine dry beads; equilibrated with buffer at pH 8.0) in order to remove the unreacted PiMP. The column was stacked with 52.5 μL of buffer at pH 8.0 (containing 1 g/L bovine serum albumin and 0.02% NaN$_3$), and spun at 600×g for 1 min, followed by another 1 min at 1000×g. 2-PAM solution (4 μL, 0.1 M) and NaN$_3$ (1 μL, 2%) were added to the eluate in order to reactivate the residual inhibited AChE (unaged) and prevent bacterial contamination.

After reacting for 2 d, Sephadex treatment was repeated to remove 2-PAM. PiMP (1 μL, 0.2 min in 2% acetonitrile) and NaN$_3$ (1 μL×2%) were added again to age the residual active AChE by reacting for 2 h. After removing PiMP again with Sephadex, NaN$_3$ was added again and the solution was stored at 4° C. for further use. A control of native AChE was prepared in parallel by replacing PiMP solution with blank 2% acetonitrile.

Aging of AChE by PiMP for Bottom-up proteomics: To 89 μL of buffer at pH 7.0 (without BSA), 1 μL×2% NaN$_3$, AChE (7.5 μL, 4 g/L in 1:1 glycerin/water) and PiMP (2.5

µL, 0.2 min in 2% acetonitrile) were added. After reacting for 2 h, the solution was washed in an Amicon centrifugal ultrafilter (cut-off molecular weight 30 kDa) with 3×400 µL of buffer at pH 8.0 (without BSA) in order to remove the unreacted PiMP. The filter was spun at 14,000×g for 4 min in each round of wash. The protein concentrate was diluted back to 100 µL. 2-PAM solution (4 µL, 0.1 M) and $NaN_3$ (1 µL, 2%) were added in order to reactivate the residual inhibited AChE (unaged) and prevent bacterial contamination.

After reacting for 2 d, the sample was washed again to remove 2-PAM. PiMP (1 µL, 0.2 min in 2% acetonitrile) and $NaN_3$ (1 µL×2%) were added again to age the residual active AChE by reacting for 2 h. After removing PiMP again with ultrafiltration, $NaN_3$ was added and the solution was stored at 4° C. for further use. A control of native AChE was prepared in parallel by replacing PiMP solution with blank 2% acetonitrile.

Aging of AChE by DFP for Screening and Kinetics: To 37.5 µL of buffer at pH 7.0 (containing 1 g/L bovine serum albumin and 0.02% $NaN_3$), AChE (7.5 µL, 4 g/L in 50% glycerol) and DFP (2.5 µL, 0.2 min in 2% DMSO) were added. After reacting for 3 d, the solution was treated with a Sephadex G-25 spin column (0.1 g of superfine dry beads; equilibrated with buffer at pH 8.0) in order to remove the unreacted DFP. The column was stacked with 52.5 µL of buffer at pH 8.0 (containing 1 g/L bovine serum albumin and 0.02% $NaN_3$), and spun at 600×g for 1 min, followed by another 1 min at 1000×g. $NaN_3$ was added and the solution was stored at 4° C. for further use. A control of native AChE was prepared in parallel by replacing DFP solution with blank 2% DMSO.

Aging of AChE by DFP for Bottom-up Proteomics: To 89 µL of buffer at pH 7.0 (without BSA), 1 µL×2% $NaN_3$, AChE (7.5 µL, 4 g/L in 50% glycerol) and DFP (2.5 µL, 0.2 min in 2% DMSO) were added. After reacting for 3 d, the solution was treated with a Sephadex G-25 spin column (0.1 g of superfine dry beads; equilibrated with buffer at pH 8.0) in order to remove the unreacted DFP. The column was spun at 600×g for 1 min, followed by another 1 min at 1000×g. $NaN_3$ was added and the solution was stored at 4° C. for further use. A control of native AChE was prepared in parallel by replacing DFP solution with blank 2% DMSO.

Ellman's Assay: Ellman's assay(20) was carried out on clear flat-bottom 96-well microplates. The assay solution was 180 µL×0.56 min of acetylthiocholine in pH 8.0 buffer, containing 0.1 g/L of BSA and 1.1 min of 5,5'-dithio-bis-(2-nitrobenzoic acid) (DTNB). 20 µL of tested AChE sample was added to initiate the reaction. The absorption at 412 nm was monitored at 25° C. with Molecular Devices Spectra-Max i3 microplate reader. The initial absorbance-time slope was measured.

Screening of Alkylators: Each realkylator (hydrochloride, 4 µL×5, 25 or 100 min) was mixed with methylphosphonate-aged AChE (2 µL), phosphate buffer (pH 8.0 containing 1 g/L BSA and 0.02% $NaN_3$), and $NH_4F$ (4 µL×100 min). After reacting at 37° C. for 1 d, each sample was treated with 2-PAM for 1 h to reactivate the realkylated AChE. As aforementioned, three controls were prepared in parallel. In the positive and negative controls, the realkylator solution was replaced with blank buffer. In the 2-PAM control, it was replaced with 4 min 2-PAM solution. In the positive control, the aged AChE was replaced with same amount of native AChE.

After the reactions, all reagents were removed with a Zeba desalting spin plate (purchased from Thermo Fisher, USA). The AChE activity of each sample was determined with Ellman's assay. Each sample was tested in four replicate wells. The average initial slope of the four absorbance-time plots of each sample and the standard deviation were divided by that of the control to obtain the relative activity and error.

Measurement of $EC_{50}$ of C8: Six concentrations of C8, ranging from 0 to 20 min, were compared against methylphosphonate-aged, combined with 2-PAM as the reactivator. $NH_4F$ was not added in this test to see whether rapid reactivation is necessary to suppress re-aging. The specific procedures are as follows:

To 94.5 µL of pH 8.0 phosphate buffer (containing 1 g/L BSA and 0.02% $NaN_3$), 2 µL as obtained aged AChE (treated with PiMP) and 4 µL of C8 solution (neutral, 0, 100, 200, 300, 400 and 500 min) were mixed, and allowed to react at 37° C. for 1 d. The final concentrations of C8 were hence 0, 4, 8, 12, 16 and 20 min, respectively. The reaction was then chased with 4 min of 2-PAM for 4 h to reactivate the realkylated AChE. The positive control and 2-PAM control were also prepared in parallel following a procedure similar to that aforementioned in Section 4.3. The reagents were removed in the end by size exclusion spin columns (filled with 0.1 g dry weight of superfine Sephadex G-25) Ellman's assay was carried out following the aforementioned procedure.

The resurrected AChE activity increased with C8 concentration and showed a plateau. Concentrations higher than 12 min did not show dramatic further increased activity, presumably due to saturated binding. 12 min was hence chosen as the optimal concentration of neutral C8 in subsequent tests against methylphosphonate-aged AChE. The dissociation constant as defined by equation $K_D=[QMP]\cdot[E]/[E\text{-}QMP]$ was used for a nonlinear regression with GraphPad Prism 6, where [QMP] stands for C8 concentration, [E] for aged AChE concentration and [E-QMP] for the noncovalent complex of aged AChE and C8. The obtained $K_D$ was 5.87 min. $EC_{50}$ is equal to $K_D$ in this case.

Comparison of C8 concentrations against aged AChE (after 24 h). The red dashed line and black dotted line stand for the activities of 2-PAM controls of methylphosphonate-aged and isopropyl phosphate-aged AChE, respectively.

The $EC_{50}$ against isopropyl phosphate-aged AChE was similarly measured. The range of final concentrations was 0~10 min. As the concentration of C8 increased, the resurrected activity also approached a plateau. Nonlinear regression was performed to find the dissociation constant. The obtained $K_D$ was 1.18 min, which is lower than that against methylphosphonate-aged AChE. The difference in $K_D$ values against enzymes aged by different OPs may be related to direct interactions between QMP and the different phosphyl groups, or the slight difference in enzyme conformation.

Kinetics of Alkylation Induced by C8: Aged AChE (25 µL) was mixed with 167 µL of pH 8.0 phosphate buffer (containing 1 g/L BSA and 0.02% $NaN_3$) and C8 solution (neutral, 8 µL×100 min) and incubated at 37° C. The negative control, positive control and 2-PAM control were also prepared in parallel as aforementioned. Aliquots of 10 µL were taken at various time intervals (1~5 d), and mixed with 86 µL buffer and 4 µL×100 min 2-PAM. After reacting for another 4 h, all reagents were then removed by Sephadex size exclusion spin columns. AChE activity was then determined with Ellman's assay as aforementioned. 100% was set at the t=0 d point of the positive control.

Bottom-up Proteomics: Isopropyl phosphate-aged AChE (60 µL, aged with DFP as described above without use of BSA) was mixed with pH 8.0 phosphate buffer (36 µL, no BSA or $NaN_3$) and C8 solution (neutral, 4 µL×100 µL). BSA was not used to minimize complication in LC-MS/MS. The positive control, negative control and 2-PAM control were prepared in parallel as aforementioned. After reacted for 11 d at 37° C., 100 µL acetonitrile was added to denature the enzyme. 10 min later, the solution was washed through an Amicon Ultra centrifugal filter (3 kDa cut-off molecular weight, purchased from EMD Millipore) and with 3×400 µL ammonium acetate buffer (40 min, pH7.5) to remove organic solvent and reagents. 40 µL×0.1 g/L modified porcine trypsin (Arg and Lys methylated, sequencing grade, purchased from Promega) was added. After reacted at 37° C. for digestion for 7 h, the reaction was terminated by the addition of 10 µL×1 M acetic acid.

Liquid chromatography-tandem mass spectrometry (LC-MS/MS) of the digests was carried out on a Thermo Scientific Orbitrap Fusion mass spectrometer equipped with EASY-Spray Sources ion source in positive ion mode. The peptide solution (6.4 µL) was separated on a capillary column (C18 stationary phase, 3 µm particles, 100 Å pores, 75 µm×150 mm capillary, Thermo Scientific). Each sample was first desalted with a µ-Precolumn Cartridge (Thermo Scientific) then eluted onto the column. Mobile phases A and B were water and acetonitrile, respectively. Both contained 0.1% formic acid. Flow rate was 300 nL/min. The ionization spray voltage was 1.7 kV and the capillary temperature was 275° C. The preview mode data dependent TopSpeed™ method was used: the analysis was programmed for a full $MS^1$ scan of the precursor ions ranging from m/z 400 to 1600, followed by fragmentation and $MS^2$ scan to determine amino acid sequence and modifications from the most abundant peaks in $MS^1$ in the next 3 seconds. To achieve high mass accuracy MS determination, the full scan was performed at FT mode and the resolution was set at 120,000. The AGC Target ion number for FT full scan was set at $2×10^5$ ions, maximum ion injection time was set at 50 ms and micro scan number was set at 1. $MS^2$ was performed using ion trap mode to ensure the highest signal intensity of $MS^2$ spectra using both CID (for 2+ and 3+ charges) and ETD (for 4+~6+ charges) methods. The AGC Target ion number for ion trap $MS^2$ scan was set at 1000 ions, maximum ion injection time was set at 100 ms and micro scan number was set at 1. The CID fragmentation energy was set to 35%. Dynamic exclusion was enabled with a repeat count of 1 within 60 s and a low mass width and high mass width of 10 ppm.

Sequence information from the MS/MS data was processed by converting the *.raw files into a merged file (*.mgf) using an in-house program, RAW2MZXML_n_MGF_batch (merge.pl, a Perl script). Isotope distributions for the precursor ions of the MS/MS spectra were deconvoluted to obtain the charge states and monoisotopic m/z values of the precursor ions during the data conversion. The resulting *.mgf files were searched using Mascot Daemon by Matrix Science version 2.5.1 (Boston, Mass.) against SwissProt other Actinopterygii (ray-finned fishes except Japanese pufferfish and zebrafish) databases (SwissProt_ID 2016_09, 2085 sequences). The mass accuracy of the precursor ions was set to 10 ppm, and accidental pick of $^{13}C$ peaks was also included into the search. The fragment mass tolerance was set to 0.8 Da. Considered variable modifications were oxidation (Met), deamidation (Asn and Gln) and OP-related Ser modifications. They include the DFP-inhibited, the isopropyl phosphate-aged and the realkylated forms. Also, the realkylated Ser residue might also be attacked by its own hydroxyl group to be reactivated or lose the isopropyl and form a lactone product. Another possible reaction was a re-aging route which released the isopropyl group rather than the QM group. In this case, the re-aged AChE could be further re-realkylated by a second C8 molecule.

Fixed modification of carbamidomethylation (Cys) was also considered. Up to four missed cleavages for the enzyme were permitted. A decoy database was also searched to determine the false discovery rate (FDR), and peptides were filtered according to the FDR. The significance threshold was set at p<0.05. Modification peptides were manually validated.

21 sequences have been identified in the positive control, as shown in Table 1, including peptide QVTIFGE<u>S</u>AGAASVGMHLLSPDSRPK (SEQ ID NO: 1). The charge state of the peptide was +4. The score of this protein was 2225. The catalytic Ser (underscored) was unmodified because the enzyme was native. The observed mass was 2654.3496~2654.3510 Da while the theoretical value is 2654.3486 Da. The error was +0.35~+0.9 ppm. The sequence coverage (42%) is shown below with the identified sequences in bold:

TABLE 1

Peptide sequences (SEQ ID NO: 2) identified in the positive control.

```
  1 MKILDALLFP VIFIMFFIHL SIAQTDPELT IMTRLGQVQG TRLPVPDRSH

51 VIAFLGIPFA EPPLGKMRFK PPEPKKPWND VFDARDYPSA CYQYVDTSYP

101 GFSGTEMWNP NRMMSEDCLY LNVWVPATPR PHNLTVMVWI YGGGFYSGSS

151 SLDVYDGRYL AHSEKVVVVS MNYRVSAFGF LALNGSAEAP GNVGLLDQRL

201 ALQWVQDNIH FFGGNPKQVT IFGESAGAAS VGMHLLSPDS RPKFTRAILQ

251 SGVPNGPWRT VSFDEARRRA IKLGRLVGCP DGNDTDLIDC LRSKQPQDLI

301 DQEWLVLPFS GLFRFSFVPV IDGVVFPDTP EAMLNSGNFK DTQILLGVNQ

351 NEGSYFLIYG APGFSKDNES LITREDFLQG VKMSVPHANE IGLEAVILQY

401 TDWMDEDNPI KNREAMDDIV GDHNVVCPLQ HFAKMYAQYS ILQGQTGTAS

451 QGNLGWGNSG SASNSGNSQV SVYLYMFDHR ASNLVWPEWM GVIHGYEIEF

501 VFGLPLEKRL NYTLEEEKLS RRMMKYWANF ARTGNPNINV DGSIDSRRRW
```

TABLE 1-continued

Peptide sequences (SEQ ID NO: 2) identified in the positive control.

551 PVFTSTEQKH VGLNTDSLKV HKGLKSQFCA LWNRFLPRLL NVTENIDDAE

601 RQWKAEFHRW SSYMMHWKNQ FDHYSKQERC TNL

Reactivation of Inhibited AChE by Five QMPs: EMP was synthesized following a procedure adapted from that of PiMP. Electric eel AChE (~10 units in 2.5 µL×50% glycerin) was mixed with BSA (95 µL×1 g/L in 40 min phosphate buffer, pH 7.0, containing 0.02% NaN$_3$) and EMP (2.5 µL×0.2 min in 2% DMSO). After reacted at 37° C. for 1 h, the solution was cleaned with a Sephadex spin column (0.1 g dry superfine G-25, equilibrated at pH 8.0). Controls with EMP replaced by blank solvents were also prepared.

Each tested compound (neutral form, 6.4 µL×50 min) was mixed with 3.1 µL of the freshly prepared inhibited AChE solution and BSA (150.5 µL×1 g/L in 40 min phosphate buffer, pH 8.0, containing 0.02% NaN$_3$). Four replicates were made for each compound. Aliquots of 20 µL was taken and analyzed with Ellman's assay as aforementioned. For comparison, 2-PAM at the same concentration was tested in parallel. The negative and positive controls had the reagent solution replaced with blank buffer. The AChE in the positive control was native and not treated with EMP.

C2
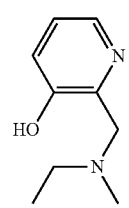

C3
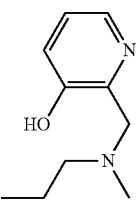

C5
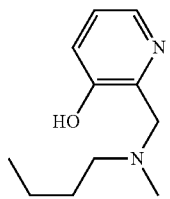

C7
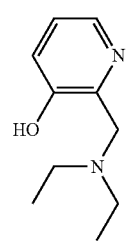

C8
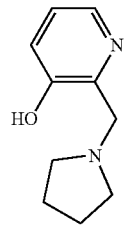

EMP
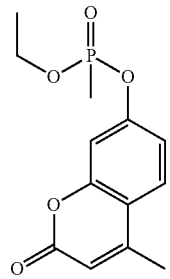

pH Effect in Resurrection of Aged AChE: To 94 µL×1 g/L BSA solution (in 0.2 M phosphate buffer, containing 0.02% NaN$_3$), 2 µL of methylphosphonate-aged AChE solution (treated with PiMP as described above) and 4 µL×100 min C8 solution were added. A negative control was prepared with C8 solution replaced with blank water. A positive control was similarly prepared in parallel with the aged AChE replaced with native AChE. Buffers at four pH values were compared: 6, 7, 8 and 9. Samples were incubated at 37° C. for 1 d. AChE activity was then determined with Ellman's assay.

Results:

Screening of Realkylator Library: Molecular docking and molecular dynamics (MD) simulations were previously conducted to evaluate the potential orientation of QMPs at the active site of methylphosphonate-aged human AChE (huAChE). (R. J. Yoder, et al., *ACS Med Chem Lett* (2017)). A larger library of QMPs was studied through this modeling approach using an in silico model of aged huAChE. Both phenyl and pyridyl-QMPs were evaluated for their fit in the aged active site. Optimizations, molecular docking, and MD simulations were all performed over this initial library of compounds. The three lowest-energy docking poses of each flexible ligand across 13 rigid aged AChE structures were used as starting points for subsequent 1 ns MD simulations. The QMPs were evaluated based on the time throughout the MD simulations in which the reactive benzylic carbon was within close proximity to the anionic O—(P=O) of the aged serine.

Figure 2:
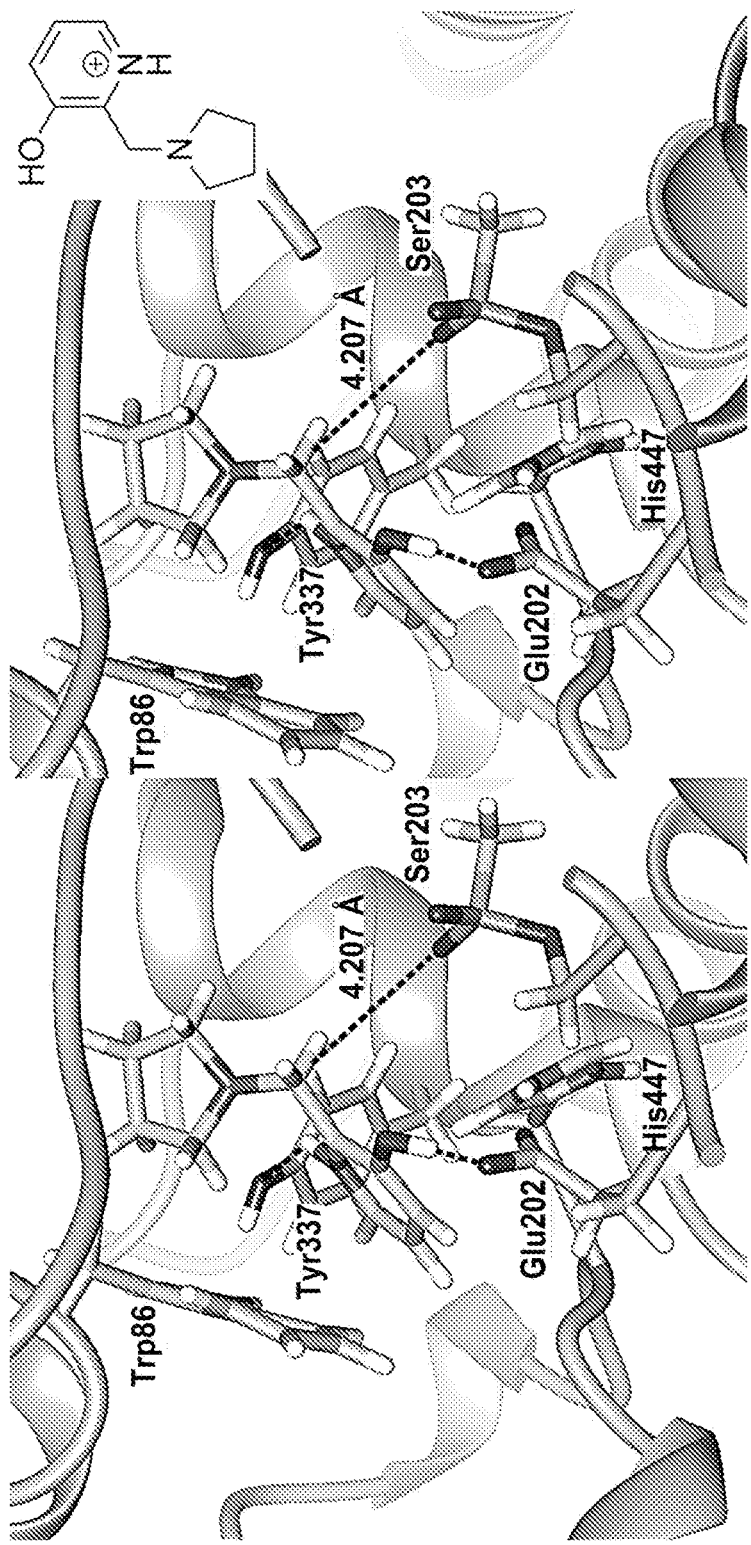
FIG. 2 shows a snapshot obtained from a 1 ns MD simulation, demonstrating a protonated QMP (C8) near the active site of aged AChE (wall-eyed stereo). The electrophilic carbon is ~4.2 Å from the phosphylated oxyanion, and the QMP. Hydrogen bonds with short contact distances are shown (dashed lines).

It was determined that pyridyl compounds had a higher propensity to be bound in the active site and close to the phosphyl oxyanion as compared to their phenyl analogues. Moreover, 3-hydroxypyridine-derived QMPs with the reactive benzylic carbon attached at the 2-position displayed promising interactions. Of the 72 compounds modeled, six of the top-10 compounds were members of that specific 3-hydroxypyridine framework. The top compound had a pyrrolidine leaving group attached to the reactive benzylic carbon (FIG. 2).

In this example, thirteen 3-hydroxypyridine-derived QMPs (C series, FIG. 3A, protonated with HCl or oxalic acid) were synthesized via Mannich reactions, and then evaluated by screening against methylphosphonate-aged (treated with PiMP) AChE. The electrophilic benzylic methylene, hypothesized to be the site of attack by nucleophiles (FIG. 1B), is attached to the 2-position of the pyridine ring, and the leaving groups were various secondary amines. The aged enzyme was reacted with various concentrations (0.2-4 min) of each QMP at 37° C., pH 8 for 1 d. Without knowing the re-aging $t_{1/2}$ of the realkylated adducts, $NH_4F$ (4 min) was added as a mild and nonselective reactivator to the screening. It was posited that once the aged AChE was realkylated, the newly formed "inhibited" AChE could be reactivated by fluoride to the native AChE. After realkylation, the samples were treated with 4 min of 2-PAM for 1 h to ensure that the realkylated AChE was completely reactivated. Ellman's assay (G. L. Ellman, et al., *Biochem Pharmacol* 7, 88-95 (1961)), with acetylthiocholine as a substrate, was carried out to determine AChE activity. Three controls were prepared and analyzed in parallel: a negative control without realkylator; a 2-PAM control with the realkylator replaced by 2-PAM; and a positive control with native AChE, rather than aged, and without realkylator.

Figure 3B:
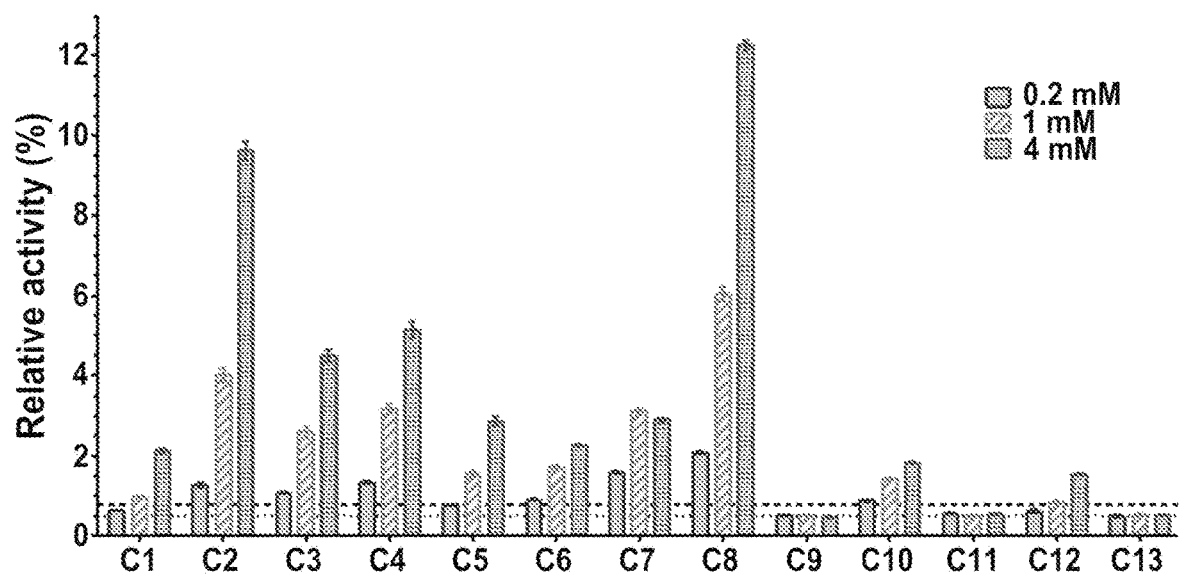
Figure 3C:
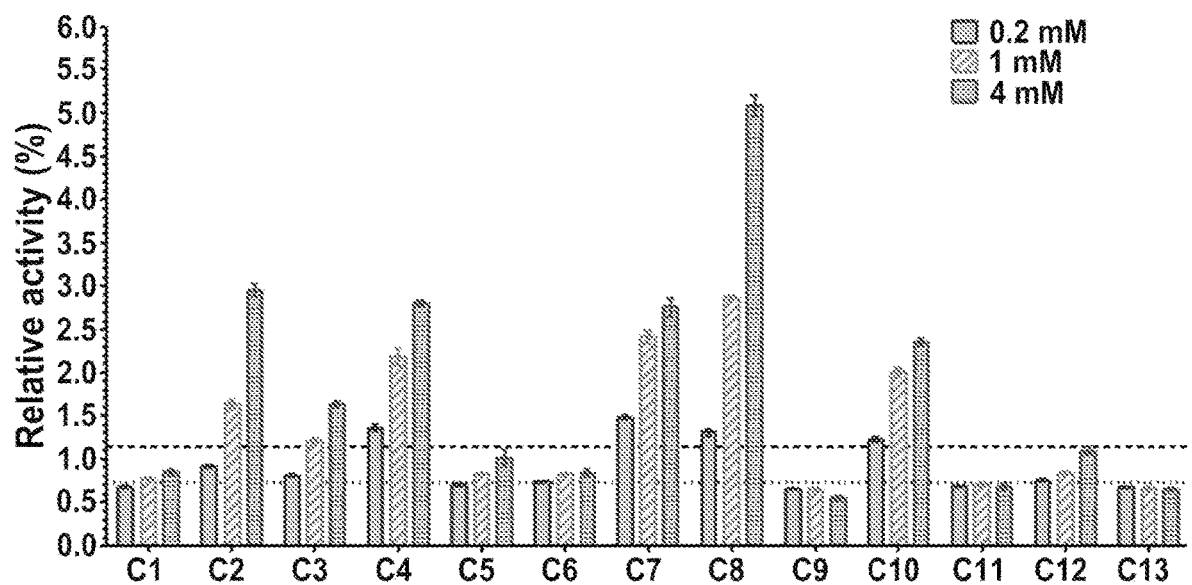

The screening results are shown in FIG. 3B. The percentage relative activity is based on the positive control. The negative and 2-PAM controls showed negligible background signals, confirming the completion of aging (dotted and dashed lines in FIG. 3B and FIG. 3C). For this small library, the only difference was the amino leaving group. Compound C7 with a diethylamino leaving group showed the highest efficacy among C1 to C7, with each of these compounds having a noncyclic amine. Efficacy was compromised when the ethyl group was shortened (C1) or lengthened (C2 to C6). Overall, the pyrrolidinyl compound C8 was the most potent candidate in this screen. The other candidates with cyclic leaving groups showed minimal or no activity. The screening against isopropyl phosphate-aged AChE (DFP-treated) showed a similar result (FIG. 3C), except that the difference between C7 and C8 was smaller than that against methylphosphonate-aged AChE.

These comparisons demonstrate that pyrrolidine is the optimum among all tested leaving groups. Hence a variety of realkylator candidates were compared with this leaving group (M series in FIG. 3A). The screenings were carried out following the same procedures as for the 3-hydroxypyridine derivatives. C8 is the only active compound in this comparison, indicating the superiority of the 3-hydroxypyridine framework over other tested scaffolds. C8 was therefore chosen as a lead compound for subsequent investigations.

Six concentrations of C8 (0-10 min), were compared against methylphosphonate-aged and isopropyl phosphate-aged eeAChE, in order to determine the $EC_{50}$ (1.18 and 5.87 mM, respectively), illustrating that further optimization is needed for a more effective therapeutic. Interestingly, fluoride was not used in the reactions, implying that it is unnecessary to limit re-aging using this reactivator.

Figure 4A:
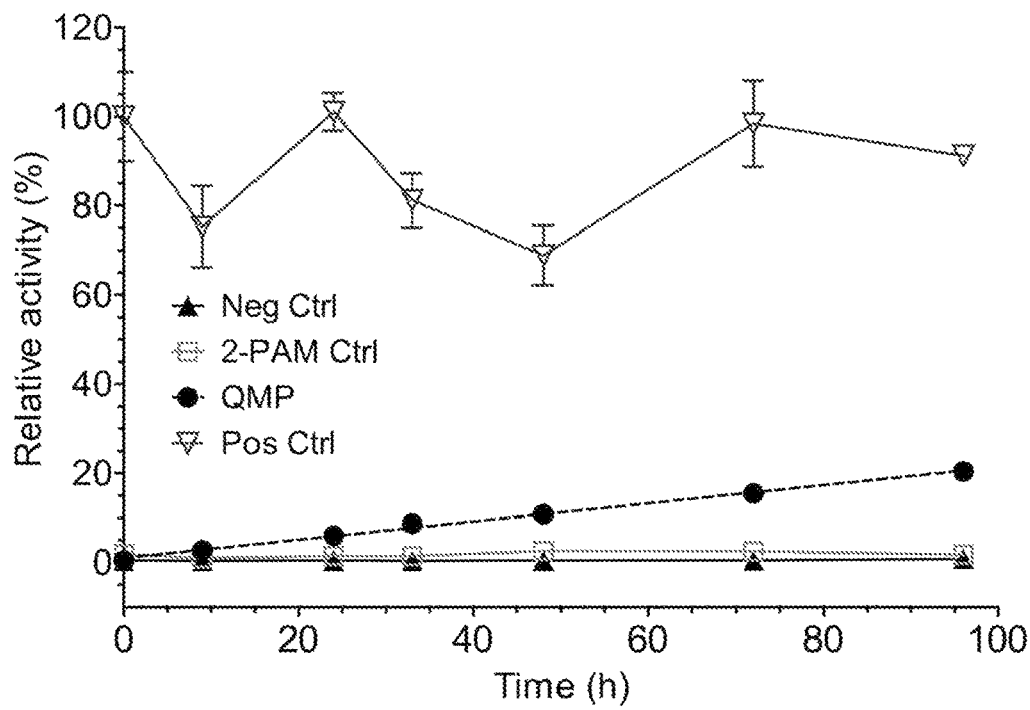
FIGS. 4A-4B show kinetics of realkylation of aged eeAChE by C8 at pH 8 for isopropyl phosphate-aged eeAChE (FIG. 4A) and for methylphosphonate-aged eeAChE (FIG. 4b). The dashed lines illustrate the result of linear regression.

Kinetics of Realkylation: Realkylation kinetics of isopropyl phosphate-aged eeAChE was monitored in the presence of 4 min of C8. The negative control, positive control and 2-PAM control were also prepared and tested. Aliquots were withdrawn at various time intervals, and reacted with 4 min of 2-PAM for 4 h. The resurrected AChE was quantified using Ellman's assay. As realkylation progressed, increasing activity was seen in the sample treated with C8 (FIG. 4A). After 4 days, the resurrected relative activity was as high as 20.4%. This value may be high enough to relieve victims from cholinergic symptoms, (G. B. Koelle, et al., *J Pharmacol Exp Ther* 120, 488 (1957); G. B. Koellel, et al., *J Pharmacol Exp Ther* 87, 421 (1946); and A. Mazur, et al., *J Biol Chem* 163, 261-276 (1946)) though it was achieved in vitro with a high dosage and after weeks of reaction. The apparent reaction rate was 0.20% per hour ($r^2$=0.9958).

Figure 4B:
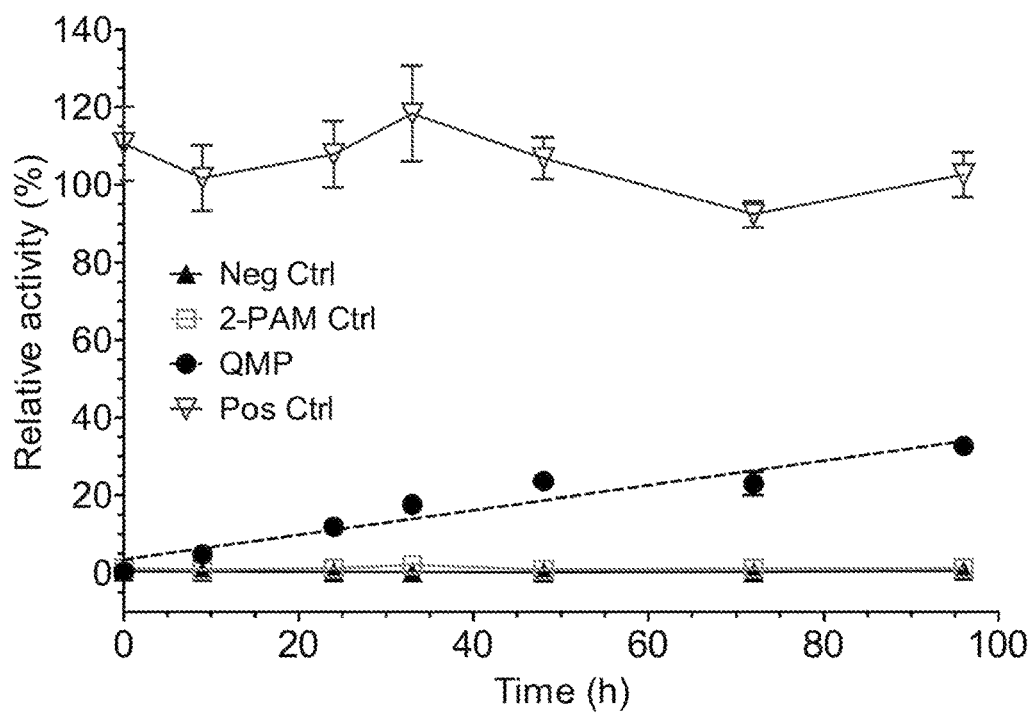
Figure 5A:
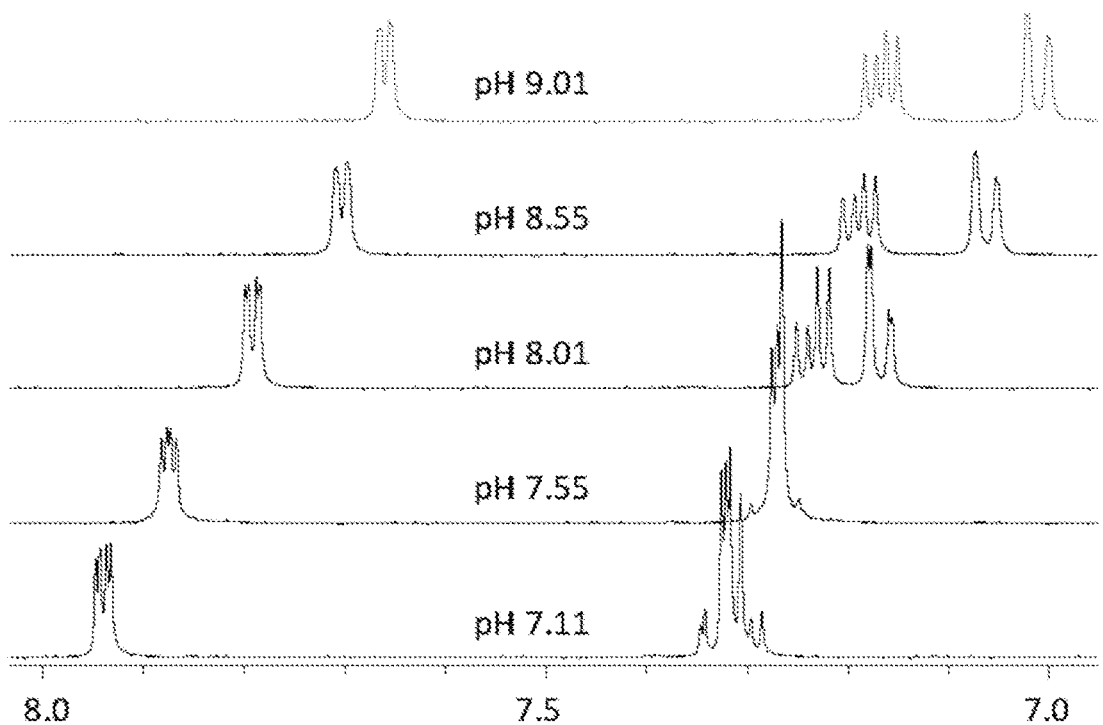
FIGS. 5A-5D shows influence of C8 protonation states on spectra and binding.
Figure 5B:
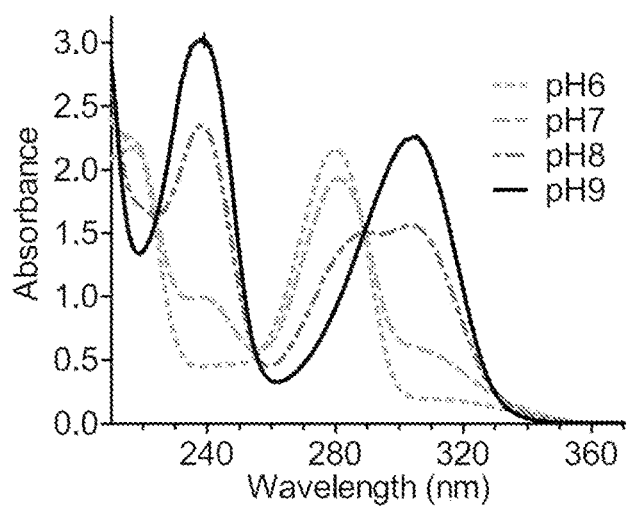
Figure 5C:
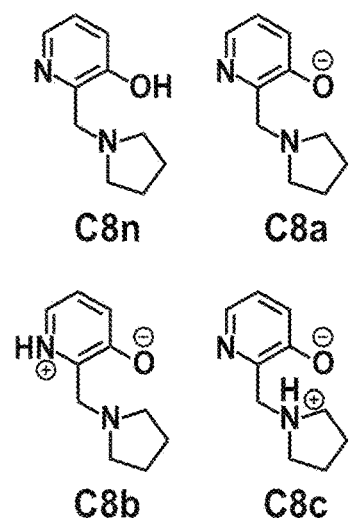
Figure 5D:
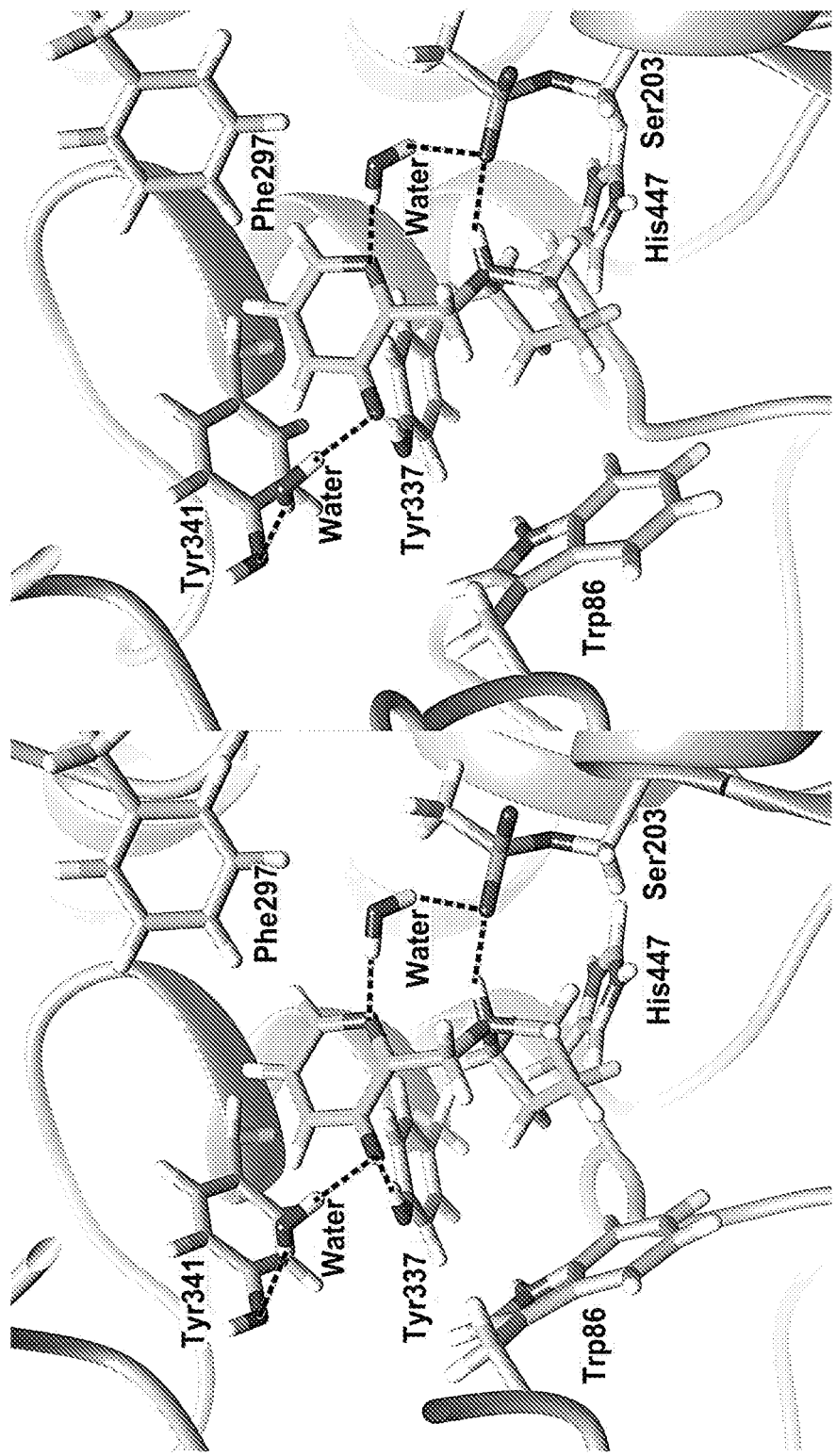
Figure 6:
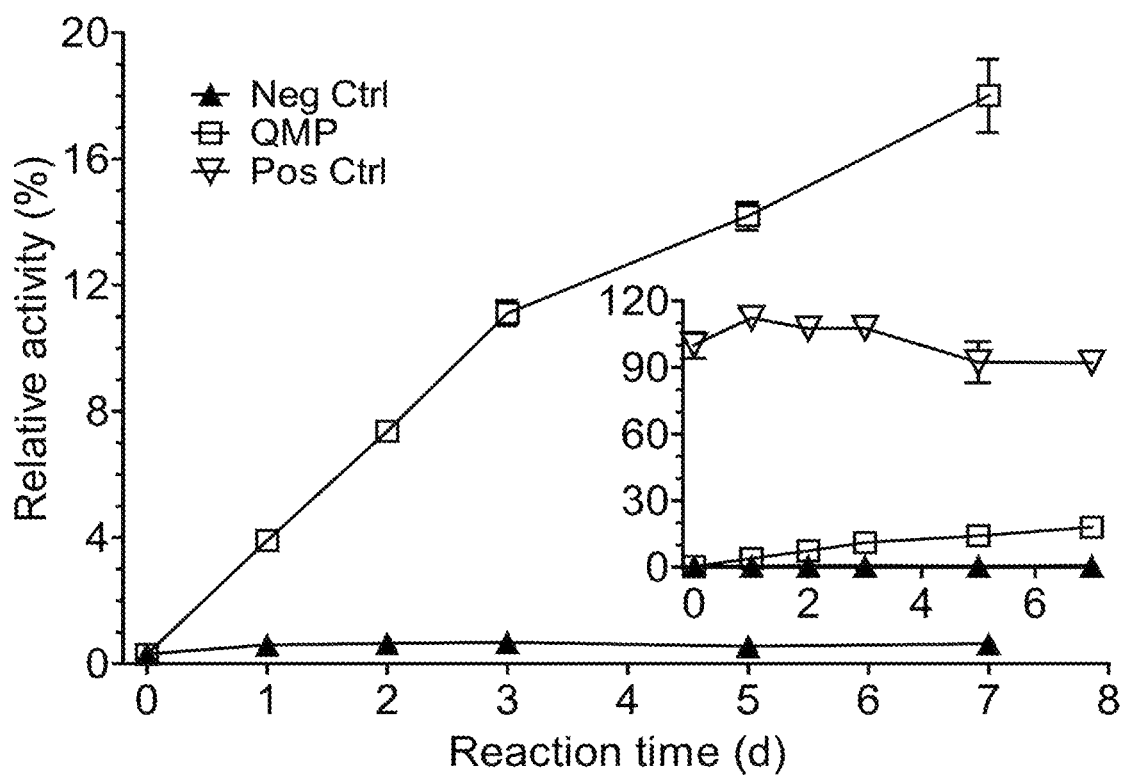
FIG. 6 shows kinetics of resurrection of isopropyl phosphate-aged human AChE (huAChE) by C8 (pH 9). Inset shows the positive control over the same time frame.

Realkylation kinetics of methylphosphonate-aged AChE was monitored in the presence of 4 min of neutral C8. The C8-treated sample displayed resurrected activity, which reached 32.7% after 4 days (FIG. 4B). The apparent reaction rate was 0.32% per hour ($r^2$=0.9185) and faster than against isopropyl phosphate-aged AChE.

Bottom-up Proteomics: Besides determining the resurrected AChE activity by Ellman's assay, confirmation of the reaction between realkylators and aged AChE can also be revealed by mass spectrometry. Bottom-up proteomics (J. Sun, et al., *Journal of Chromatography B* 877, 3681-3685 (2009) and J. Marsillach, et al., *Neurotoxicology* 32, 656-660 (2011)) was used to sequence the peptides and differentiate enzyme species with variable modifications at the catalytic serine. Isopropyl phosphate-aged eeAChE was treated with C8 for 11 d, and digested it with trypsin. 2-PAM was not applied after the C8 treatment. The digest was analyzed with LC-MS/MS. The positive, negative and 2-PAM controls were also prepared in parallel, and quantification was obtained from the LC peak areas (Table 2).

Peptide QVTIFGESAGAASVGMHLLSPDSRPK (SEQ ID NO: 1) (residues 195-220), was observed in all samples. The catalytic serine (underscored) in the positive control was completely unmodified because the enzyme was native. By contrast, the modification observed in the negative and 2-PAM controls indicated that they were completely aged. The wild-type serine or otherwise modified serine was not observed at this position. Compared to the unmodified peptide, there was a mass shift of 122.0133 Da ($C_3H_7O_3P$ added), which matches the added isopropyl phosphyl moiety. In the C8-treated sample, the unmodified catalytic serine was observed, indicating resurrection induced by the QMP. Realkylated AChE, however, was not directly observed. Similar results were obtained with methylphosphonate-aged AChE.

TABLE 2

Percentages of AChE species determined by LC-MS/MS

| | Percentage (%) | | | | | |
| --- | --- | --- | --- | --- | --- | --- |
| | Isopropyl phosphate-aged | | | Methylphosphonate-aged | | |
| Sample | Native | Aged | Realkylated | Native | Aged | Realkylated |
| Positive Control | 100 | 0 | 0 | 100 | 0 | 0 |
| Negative Control | 0 | 100 | 0 | 0 | 100 | 0 |
| 2-PAM Control | 0 | 100 | 0 | 0 | 100 | 0 |
| C8-treated | 15.4 | 84.6 | 0 | 2.1 | 97.9 | 0 |

Neither 2-PAM nor fluoride was added to the QMP-treated samples for reactivation of realkylated AChE, suggesting the reactivation activity of C8-reactivating the realkylated AChE. This is in agreement with reports of reactivation activity of Mannich phenols by Katz et al., (F.

S. Katz, et al., *Chembiochem* 16, 2205-2215 (2015)) Cadieux et al., (C. L. Cadieux, et al., *Chem-Biol Interact* 259, 133-141 (2016)) and Bierwisch et al. (A. Bierwisch, et al., *Toxicol Lett* 246, 49-56 (2016)). The absence of realkylated AChE in the sample was unexpected.

Reactivation of Inhibited AChE by Five QMPs: Five representative C series QMPs, namely C2, C3, C5, C7 and C8, were reacted with eeAChE inhibited with a VX analogue (EMP, an ethyl methylphosphonate compound) to determine whether they are reactivators. OP was chosen because the aging by VX is slow. (F. Worek, et al., *Biochem Pharmacol* 68, 2237-2248 (2004)). After inhibition by EMP, the inhibited AChE was incubated with the chosen QMPs (4 min) at pH 8.0 and 37° C., then monitored by Ellman's assay. All tested QMPs except C7 exhibited obvious and similar reactivation activity, while C7 showed slower kinetics. This may explain why C8 can efficiently resurrect aged AChE in the absence of 2-PAM and fluoride. The apparent rate constants, as well as relative activity of reactivated AChE at three time points, are listed in Table 3, and all tested compounds reacted slower than 2-PAM, which reached its plateau before the first aliquot could be taken.

TABLE 3

After inhibition by EMP, relative activity of reactivated eeAChE at three time points, and apparent rate constants of first-order or pseudo-first-order reaction of AChE reactivation, spontaneous or by QMPs.

| | Relative activity (%) | | | |
|---|---|---|---|---|
| QMP | 4 h | 8 h | 22 h | k ($h^{-1}$) |
| Negative Control | 10.3 ± 0.3 | 17.4 ± 0.3 | 39.6 ± 0.4 | 0.032 ± 0.003 |
| C2 | 30.3 ± 0.9 | 48 ± 2 | 82 ± 1 | 0.090 ± 0.003 |
| C3 | 21.8 ± 0.2 | 36 ± 2 | 71 ± 1 | 0.063 ± 0.004 |
| C5 | 26 ± 1 | 43 ± 2 | 76.7 ± 0.8 | 0.080 ± 0.003 |
| C7 | 15.4 ± 0.7 | 27 ± 2 | 52.9 ± 0.5 | 0.056 ± 0.003 |
| C8 | 30.8 ± 0.7 | 50 ± 2 | 85.0 ± 0.8 | 0.088 ± 0.003 | pH Effect for C8 Activity: There are three heteroatoms in C8, forming multiple possible protonation states. Each of them may interact with the aged AChE active site with different orientations, affinities and rates. $^1$H NMR spectra of C8 displayed shifting signals as the pH changed (FIG. 5A). The UV-vis spectra also dramatically changed when pH was increased from 6 to 9 (FIG. 5B), indicating a $pK_a$ between 7 and 8. The resurrection of methylphosphonate-aged eeAChE by 4 min C8 at four different pH values (6~9) at 37° C. for 1 d, with neither 2-PAM nor fluoride being used was performed. The relative activity of C8-resurrected AChE increased dramatically with pH (Table 4)—over 20% at pH 9. Similar effects were also observed with isopropyl phosphate-aged eeAChE.

The pH dependence directed further study regarding the activity of the isomers. The four most probable isomeric states at pH 8 and 9 were compared, namely the neutral, anionic and two zwitterionic forms (C8n, C8a, C8b and C8c, respectively, FIG. 5C). For each structure, molecular docking into a number of geometries of the aged AChE yielded a few docked poses. Then, after resolvation, an MD trajectory was computed; the location of the exchangeable proton has a dramatic effect on the affinity of the ligand toward different zones in the AChE active site. The simulations suggest that both zwitterionic forms (C8b and C8c) have stable interactions and well-defined proximity to the anionic oxygen of the phosphylated serine. The neutral form (C8n) also stably binds to the active site, but the benzylic carbon is not oriented for realkylation. The anionic form (C8a) gradually moves away from the active site during the simulation. Calculations at the B3LYP/6-311+G (SMD, water) level of theory suggest that C8c (pyrrolidinyl nitrogen protonated) has a free energy that is lower than C8b (pyridinyl nitrogen protonated) by 3.1 kcal/mol, hence is a more probable species. Ser203, Tyr337, Tyr341 residues, along with some hydrogen-bonded water molecules, contribute significantly to the binding of C8c by hydrogen bonding and electrostatic attractions (FIG. 5**D).

TABLE 4

Relative activities of C8-treated samples and negative controls after incubation of aged eeAChE for 1 d at various pH values, as a percentage of the positive control at the corresponding pH.

| | Relative activity (%) | | | |
|---|---|---|---|---|
| | Methylphosphonate-aged | | Isopropyl phosphate-aged | |
| pH | Negative control | C8 | Negative control | C8 |
| 6 | 0.139 ± 0.003 | 0.273 ± 0.004 | 1.05 ± 0.10 | 0.68 ± 0.06 |
| 7 | 0.120 ± 0.006 | 1.24 ± 0.02 | 1.24 ± 0.06 | 1.04 ± 0.07 |
| 8 | 0.184 ± 0.010 | 8.47 ± 0.17 | 1.43 ± 0.09 | 3.58 ± 0.33 |
| 9 | 0.225 ± 0.008 | 21.1 ± 0.5 | 1.57 ± 0.11 | 5.27 ± 0.59 |

Resurrection of Aged Human AChE after exposure to DFP: The efficacy of C8 was examined against aged huAChE. The activity of isopropyl phosphate-aged (DFP-treated) recombinant huAChE was monitored in the presence of 4 min of C8 at pH 9 for a week by Ellman's assay. After 7 d of reaction (FIG. 6), 18% of the aged enzyme was resurrected, and the relative activity of huAChE was still increasing. Neither 2-PAM nor fluoride were used in this test, again confirming that C8 alone can resurrect aged AChE to the native form.

Conclusions: The aging of OP-inhibited AChE poses a significant issue in the classical treatment of OP poisoning which hinges on the rapid administration of nucleophilic oximes as reactivators. The realkylation/reactivation of aged AChE remains an unsolved problem amongst the scientific community. This example attempts to address this significant problem by the design and synthesis of quinone methide precursors intended to realkylate the aged phosphoryl residue. A lead compound, C8 was identified as the first compound to our knowledge that is capable of reactivating aged AChE. A significant SAR effort to increase the reactivation potential for this lead compound has been undertaken and is a continuing effort.

With in-silico guidance, 22 QMPs were synthesized with various scaffolds and leaving groups, and then evaluated them for their in vitro resurrection activity against methylphosphonate-aged and isopropyl phosphate-aged eeAChE. Multiple QMPs with a 3-hydroxypyridine scaffold, with the reactive "benzylic" carbon attached at the 2-position, proved efficacious. C8 was found to be the lead compound in the screening. Used at 4 min along with 2-PAM, C8 successfully resurrected the relative activity of isopropyl phosphate-aged eeAChE to 30.4% after 4 days. C8 at 4 min resurrected the relative activity of methylphosphonate-aged eeAChE to 32.7% after 4 days of observation. This activity for C8 is also reproduced for aged human AChE.

The activities of C8 against isopropyl phosphate-aged and methylphosphonate-aged eeAChE were also confirmed with bottom-up proteomics. The peptide containing the catalytic serine was sequenced to reveal the modification. In the samples treated with C8, partial resurrection was observed as indicated by the presence of native AChE. Realkylated AChE was not observed, though no extra reactivator was added. These observations suggest that C8 acts as a bifunctional drug, realkylating the aged AChE first and then reactivating the realkylated AChE. This hypothesis was confirmed, with C8, and at least four other C series QMPs, can reactivate AChE after inhibition by a VX analogue.

A new strategy using a structural features from a known reversible AChE inhibitor, donepezil, have been incorporated into the synthesis of a novel class of 2-methylamino-3-hydroxypyridine compounds in an attempt to increase the affinity of the potential realkylators for the targeted active site of the AChE enzyme.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative materials and method steps disclosed herein are specifically described, other combinations of the materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

What is claimed is:

1. A method for ameliorating, diminishing, reversing, treating or preventing the toxic effects of an organophosphorus compound in a subject, the method comprising administering a composition comprising a therapeutically effective amount of a compound having a structure represented by Formula I:

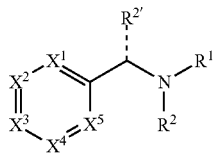

Formula I wherein
$X^1$-$X^4$ are independently selected from N, NR', and CR',
R' is, independently for each occurrence, selected from hydrogen, $C_1$-$C_6$ alkyl, $C_1$-$C_6$ alkyl halide, $C_1$-$C_6$ alkoxy, hydroxyl, halogen, amine, alkylamine, alkylammonium, nitrile, and -L-Z;
$R^1$ and $R^2$ are independently selected from $C_1$-$C_6$ alkyl, $C_1$-$C_6$ alkyl halide, $C_1$-$C_6$ alkoxy, or $R^1$ and $R^2$ combine to form a 3 to 8 membered aliphatic ring, and wherein $R^1$ and $R^2$ are optionally substituted with alkyl, heteroalkyl, cycloalkyl, cycloheteroalkyl, aryl, heteroaryl, alkyl halide, halogen, nitrile, alkoxy, hydroxyl, amine, alkylamine, and alkylammonium; and
$R^{2'}$ is optionally present and selected from $C_1$-$C_6$ alkyl, $C_1$-$C_6$ alkyl halide, $C_1$-$C_6$ alkoxy, and $C_1$-$C_6$ alkyl amine, or $R^1$ and $R^{2'}$ or $R^2$ and $R^{2'}$ combine to form a 5 to 7 membered aliphatic ring;
$X^5$ is C—OH;
L is a bond or a linker;
Z is an acetylcholinesterase inhibitor; and
wherein at least one of $X^1$-$X^4$ is N or NR'.

2. The method of claim 1, wherein the organophosphorus compound is a nerve agent.

3. The method of claim 1 wherein the compound reverses inhibition of acetylcholinesterase by the organophosphorus compound.

4. The method of claim 1, wherein the compound reactivates aged acetylcholinesterase inhibited by or conjugated to the organophosphorus compound.

5. The method of claim 1, wherein the acetylcholinesterase (AChE) is in the central nerve system (CNS).

6. The method of claim 1, wherein $R^{2'}$ is present and represents a $C_1$-$C_4$ alkyl group.

7. The method of claim 1, wherein $R^{2'}$ is absent.

8. The method of claim 1, wherein the compound is represented by a structure having the Formula II-A-1:

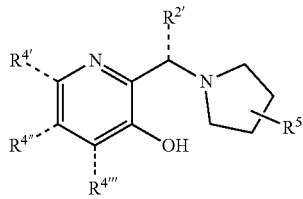

Formula II-A-1 wherein
$R^{4'}$, $R^{4''}$, and $R^{4'''}$ are independently selected from hydrogen, $C_1$-$C_6$ alkyl, halogen, $C_1$-$C_6$ alkyl halide, $C_1$-$C_6$alkoxy, nitrile, amine, -L-Z, alkylamine, and alkylammonium;
$R^5$ is selected from hydrogen, $C_1$-$C_6$ alkyl, halogen, $C_1$-$C_6$ alkyl halide, $C_1$-$C_6$ alkoxy, nitrile, amine, alkylamine, and alkylammonium;
L is a bond or a linker; and
Z is an acetylcholinesterase inhibitor.

9. The method of claim 8, wherein the compound is represented by a structure having the Formula II-A-2:

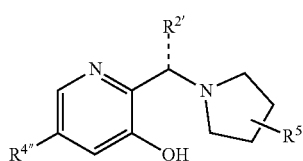

Formula II-A-2 wherein
$R^{4''}$ is selected from $C_1$-$C_6$ alkyl, halogen, $C_1$-$C_6$ alkyl halide, $C_1$-$C_6$ alkoxy, nitrile, amine, -L-Z, alkylamine, and alkylammonium;
$R^5$ is selected from $C_1$-$C_6$ alkyl, halogen, $C_1$-$C_6$ alkyl halide, $C_1$-$C_6$ alkoxy, nitrile, amine, alkylamine, and alkylammonium;
L is a bond or a linker; and
Z is an acetylcholinesterase inhibitor.

10. The method of claim 1, wherein the compound is represented by a structure having the Formula:

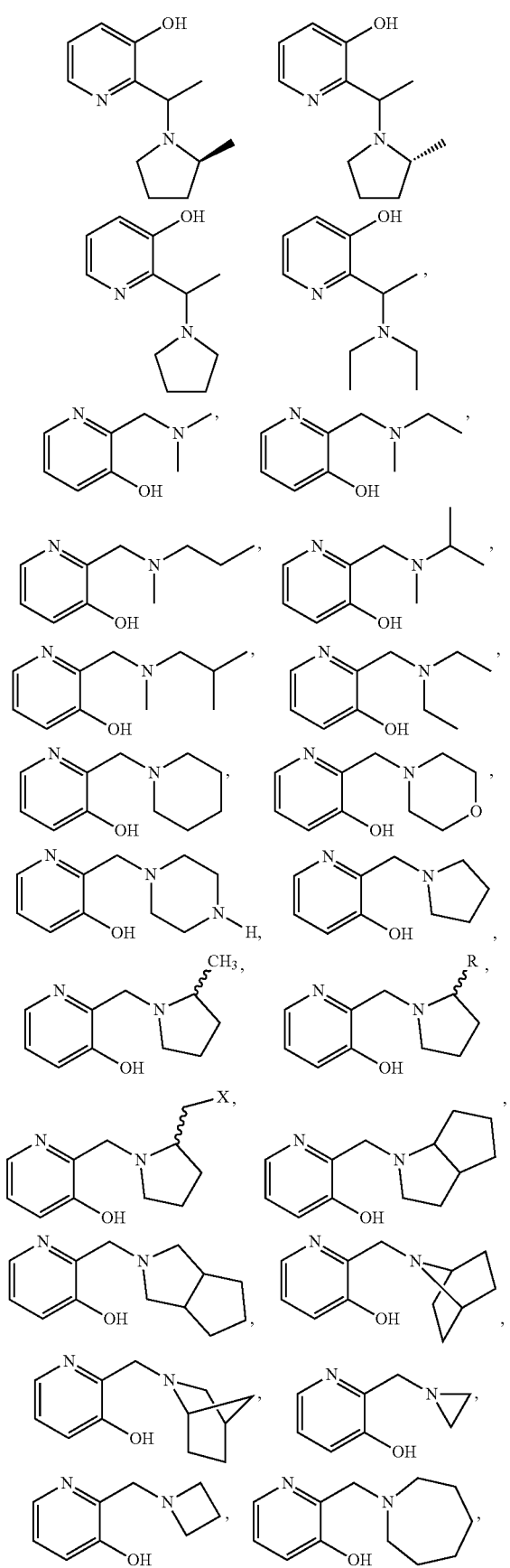

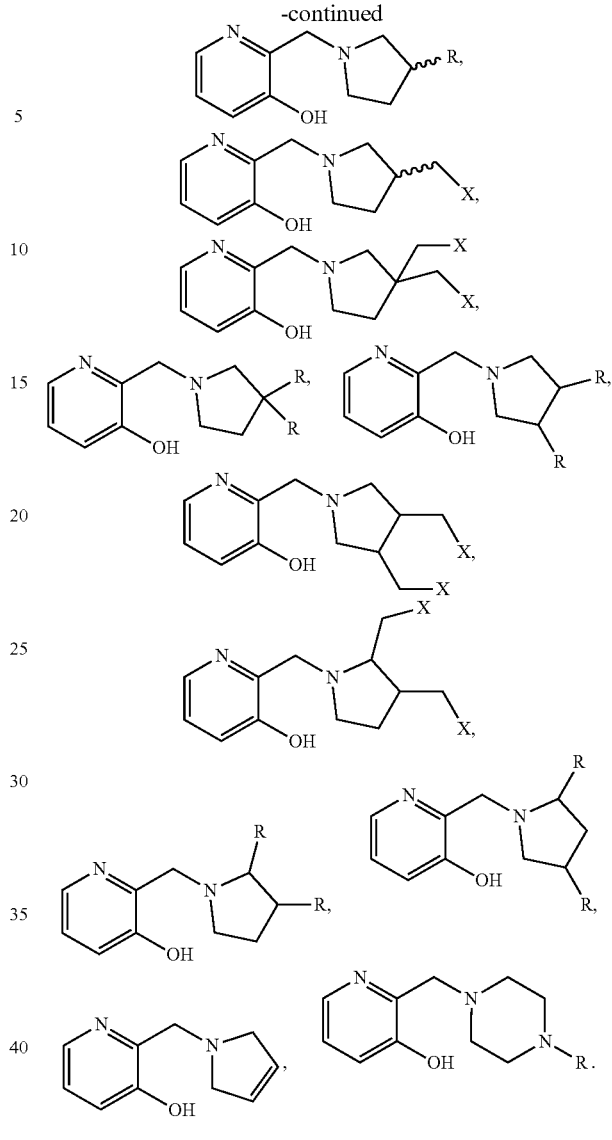

wherein R is $C_1$-$C_6$ alkyl and X is OH, OR, $NH_2$, NHR, or $NR_2$.

11. The method of claim 1, wherein the compound is represented by a structure having the Formula IV:

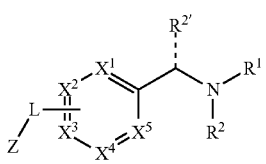

Formula IV wherein $X^1$-$X^4$ are independently selected from N, NR', C, and CR', wherein R' is independently selected from hydrogen, $C_1$-$C_6$ alkyl, $C_1$-$C_6$ alkyl halide, $C_1$-$C_6$ alkoxy, hydroxyl, halogen, amine, nitrile, alkylamine, and alkylammonium;

$R^1$ and $R^2$ combine to form a 3 to 8 membered aliphatic ring, wherein the 3 to 8 membered aliphatic ring is substituted with $C_1$-$C_6$ alkyl, $C_1$-$C_6$ alkyl halide, $C_1$-$C_6$ alkoxy, hydroxyl, halogen, amine, alkylamine, and alkylammonium;

$R^{2'}$ is optionally present and selected from $C_1$-$C_6$ alkyl, $C_1$-$C_6$ alkyl halide, $C_1$-$C_6$ alkoxy, and $C_1$-$C_6$ alkyl amine, or $R^1$ and $R^{2'}$ or $R^2$ and $R^{2'}$ combine to form a 5 to 7 membered aliphatic ring;

$X^5$ is C—OH;

L is a bond or a linker;

Z is an acetylcholinesterase inhibitor; and wherein at least one of $X^1$-$X^4$ is N or NR'.

12. The method of claim 11, wherein the compound is represented by a structure having the Formula IV-A:

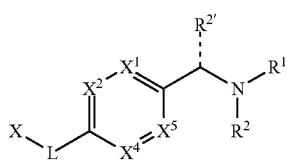

Formula IV-A wherein $X^1$, $X^2$, and $X^4$ are independently selected from N, NR', C, and CR', wherein R' is independently selected from hydrogen, $C_1$-$C_6$ alkyl, $C_1$-$C_6$ alkyl halide, $C_1$-$C_6$ alkoxy, hydroxyl, halogen, amine, nitrile, alkylamine, and alkylammonium;

$X^5$ is C—OH;

$R^1$ and $R^2$ combine to form a 3 to 8 membered aliphatic ring, wherein the 3 to 8 membered aliphatic ring is substituted with $C_1$-$C_6$ alkyl, $C_1$-$C_6$ alkyl halide, $C_1$-$C_6$ alkoxy, hydroxyl, halogen, amine, alkylamine, and alkylammonium;

$R^{2'}$ is optionally present and selected from $C_1$-$C_6$ alkyl, $C_1$-$C_6$ alkyl halide, $C_1$-$C_6$ alkoxy, and $C_1$-$C_6$ alkyl amine, or $R^1$ and $R^{2'}$ or $R^2$ and $R^{2'}$ combine to form a 5 to 7 membered aliphatic ring;

L is a bond or a linker;

Z is an acetylcholinesterase inhibitor; and wherein at least one of $X^1$, $X^2$, and $X^4$ is N or NR'.

13. The method of claim 11, wherein the acetylcholinesterase inhibitor is donepezil.

14. The method of claim 11, wherein the compound is represented by a structure below:

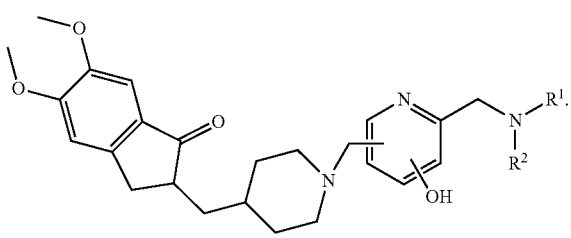

15. A method of prophylactic or therapeutic treatment of exposure to an organophosphorus nerve agent comprising administering a composition to a subject requiring such treatment in an amount effective to prophylactically or therapeutically treat exposure to the organophosphorus nerve agent, wherein the composition comprises a compound having a structure represented by Formula I:

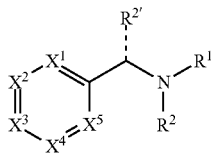

Formula I wherein $X^1$-$X^4$ are independently selected from N, NR', and CR',

R' is, independently for each occurrence, selected from hydrogen, $C_1$-$C_6$ alkyl, $C_1$-$C_6$ alkyl halide, $C_1$-$C_6$ alkoxy, hydroxyl, halogen, amine, alkylamine, alkylammonium, nitrile, and -L-Z;

$R^1$ and $R^2$ are independently selected from $C_1$-$C_6$ alkyl, $C_1$-$C_6$ alkyl halide, $C_1$-$C_6$ alkoxy, or $R^1$ and $R^2$ combine to form a 3 to 8 membered aliphatic ring, and wherein $R^1$ and $R^2$ are optionally substituted with alkyl, heteroalkyl, cycloalkyl, cycloheteroalkyl, aryl, heteroaryl, alkyl halide, halogen, alkoxy, amine, alkylamine, and alkylammonium; and $R^{2'}$ is optionally present and selected from $C_1$-$C_6$ alkyl, $C_1$-$C_6$ alkyl halide, $C_1$-$C_6$ alkoxy, and $C_1$-$C_6$ alkyl amine, or $R^1$ and $R^{2'}$ or $R^2$ and $R^{2'}$ combine to form a 5 to 7 membered aliphatic ring;

$X^5$ is C—OH;

L is a bond or a linker;

Z is an acetylcholinesterase inhibitor; and wherein at least one of $X^1$-$X^4$ is N or NR'.

16. A method for ameliorating, diminishing, reversing, treating or preventing the toxic effects of an organophosphorus compound in the central nervous system of a subject, the method comprising administering a composition comprising a therapeutically effective amount of a compound having a structure represented by Formula I:

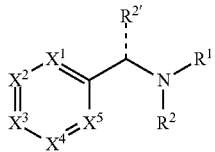

Formula I wherein $X^1$-$X^4$ are independently selected from N, NR', and CR',

R' is, independently for each occurrence, selected from hydrogen, $C_1$-$C_6$ alkyl, $C_1$-$C_6$ alkyl halide, $C_1$-$C_6$ alkoxy, hydroxyl, halogen, amine, alkylamine, alkylammonium, nitrile, and -L-Z;

$R^1$ and $R^2$ are independently selected from $C_1$-$C_6$ alkyl, $C_1$-$C_6$ alkyl halide, $C_1$-$C_6$ alkoxy, or $R^1$ and $R^2$ combine to form a 3 to 8 membered aliphatic ring, and wherein $R^1$ and $R^2$ are optionally substituted with alkyl, heteroalkyl, cycloalkyl, cycloheteroalkyl, aryl, heteroaryl, alkyl halide, halogen, alkoxy, amine, alkylamine, and alkylammonium; and $R^{2'}$ is optionally present and selected from $C_1$-$C_6$ alkyl, $C_1$-$C_6$ alkyl halide, $C_1$-$C_6$ alkoxy, and $C_1$-$C_6$ alkyl amine, or $R^1$ and $R^{2'}$ or $R^2$ and $R^{2'}$ combine to form a 5 to 7 membered aliphatic ring;

$X^5$ is C—OH;

L is a bond or a linker;

Z is an acetylcholinesterase inhibitor; and wherein at least one of $X^1$-$X^4$ is N or NR'.

* * * * *

SEQUENCE LISTING

```
<160> NUMBER OF SEQ ID NOS: 2

<210> SEQ ID NO 1
<211> LENGTH: 26
<212> TYPE: PRT
<213> ORGANISM: Artificial Sequence
<220> FEATURE:
<223> OTHER INFORMATION: Synthetic Construct

<400> SEQUENCE: 1

Gln Val Thr Ile Phe Gly Glu Ser Ala Gly Ala Ala Ser Val Gly Met
1               5                   10                  15

His Leu Leu Ser Pro Asp Ser Arg Pro Lys
            20                  25

<210> SEQ ID NO 2
<211> LENGTH: 633
<212> TYPE: PRT
<213> ORGANISM: Artificial Sequence
<220> FEATURE:
<223> OTHER INFORMATION: Synthetic Construct

<400> SEQUENCE: 2

Met Lys Ile Leu Asp Ala Leu Leu Phe Pro Val Ile Phe Ile Met Phe
1               5                   10                  15

Phe Ile His Leu Ser Ile Ala Gln Thr Asp Pro Glu Leu Thr Ile Met
            20                  25                  30

Thr Arg Leu Gly Gln Val Gln Gly Thr Arg Leu Pro Val Pro Asp Arg
        35                  40                  45

Ser His Val Ile Ala Phe Leu Gly Ile Pro Phe Ala Glu Pro Pro Leu
    50                  55                  60

Gly Lys Met Arg Phe Lys Pro Pro Glu Pro Lys Lys Pro Trp Asn Asp
65                  70                  75                  80

Val Phe Asp Ala Arg Asp Tyr Pro Ser Ala Cys Tyr Gln Tyr Val Asp
                85                  90                  95

Thr Ser Tyr Pro Gly Phe Ser Gly Thr Glu Met Trp Asn Pro Asn Arg
            100                 105                 110

Met Met Ser Glu Asp Cys Leu Tyr Leu Asn Val Trp Val Pro Ala Thr
        115                 120                 125
```

```
Pro Arg Pro His Asn Leu Thr Val Met Val Trp Ile Tyr Gly Gly
130                 135                 140

Phe Tyr Ser Gly Ser Ser Ser Leu Asp Val Tyr Asp Gly Arg Tyr Leu
145                 150                 155                 160

Ala His Ser Glu Lys Val Val Val Ser Met Asn Tyr Arg Val Ser
            165                 170                 175

Ala Phe Gly Phe Leu Ala Leu Asn Gly Ser Ala Glu Ala Pro Gly Asn
                180                 185                 190

Val Gly Leu Leu Asp Gln Arg Leu Ala Leu Gln Trp Val Gln Asp Asn
        195                 200                 205

Ile His Phe Phe Gly Gly Asn Pro Lys Gln Val Thr Ile Phe Gly Glu
210                 215                 220

Ser Ala Gly Ala Ala Ser Val Gly Met His Leu Leu Ser Pro Asp Ser
225                 230                 235                 240

Arg Pro Lys Phe Thr Arg Ala Ile Leu Gln Ser Gly Val Pro Asn Gly
                245                 250                 255

Pro Trp Arg Thr Val Ser Phe Asp Glu Ala Arg Arg Ala Ile Lys
            260                 265                 270

Leu Gly Arg Leu Val Gly Cys Pro Asp Gly Asn Asp Thr Asp Leu Ile
        275                 280                 285

Asp Cys Leu Arg Ser Lys Gln Pro Gln Asp Leu Ile Asp Gln Glu Trp
290                 295                 300

Leu Val Leu Pro Phe Ser Gly Leu Phe Arg Phe Ser Phe Val Pro Val
305                 310                 315                 320

Ile Asp Gly Val Val Phe Pro Asp Thr Pro Glu Ala Met Leu Asn Ser
                325                 330                 335

Gly Asn Phe Lys Asp Thr Gln Ile Leu Leu Gly Val Asn Gln Asn Glu
            340                 345                 350

Gly Ser Tyr Phe Leu Ile Tyr Gly Ala Pro Gly Phe Ser Lys Asp Asn
        355                 360                 365

Glu Ser Leu Ile Thr Arg Glu Asp Phe Leu Gln Gly Val Lys Met Ser
370                 375                 380

Val Pro His Ala Asn Glu Ile Gly Leu Glu Ala Val Ile Leu Gln Tyr
385                 390                 395                 400

Thr Asp Trp Met Asp Glu Asp Asn Pro Ile Lys Asn Arg Glu Ala Met
                405                 410                 415

Asp Asp Ile Val Gly Asp His Asn Val Val Cys Pro Leu Gln His Phe
            420                 425                 430

Ala Lys Met Tyr Ala Gln Tyr Ser Ile Leu Gln Gly Gln Thr Gly Thr
        435                 440                 445

Ala Ser Gln Gly Asn Leu Gly Trp Gly Asn Ser Gly Ser Ala Ser Asn
450                 455                 460

Ser Gly Asn Ser Gln Val Ser Val Tyr Leu Tyr Met Phe Asp His Arg
465                 470                 475                 480

Ala Ser Asn Leu Val Trp Pro Glu Trp Met Gly Val Ile His Gly Tyr
                485                 490                 495

Glu Ile Glu Phe Val Phe Gly Leu Pro Leu Glu Lys Arg Leu Asn Tyr
            500                 505                 510

Thr Leu Glu Glu Glu Lys Leu Ser Arg Arg Met Met Lys Tyr Trp Ala
        515                 520                 525

Asn Phe Ala Arg Thr Gly Asn Pro Asn Ile Asn Val Asp Gly Ser Ile
530                 535                 540

Asp Ser Arg Arg Arg Trp Pro Val Phe Thr Ser Thr Glu Gln Lys His
```

```
545                 550                 555                 560
Val Gly Leu Asn Thr Asp Ser Leu Lys Val His Lys Gly Leu Lys Ser
                565                 570                 575

Gln Phe Cys Ala Leu Trp Asn Arg Phe Leu Pro Arg Leu Leu Asn Val
                580                 585                 590

Thr Glu Asn Ile Asp Asp Ala Glu Arg Gln Trp Lys Ala Glu Phe His
                595                 600                 605

Arg Trp Ser Ser Tyr Met Met His Trp Lys Asn Gln Phe Asp His Tyr
        610                 615                 620

Ser Lys Gln Glu Arg Cys Thr Asn Leu
625                 630
```

UNITED STATES PATENT AND TRADEMARK OFFICE
CERTIFICATE OF CORRECTION

PATENT NO. : 11,492,340 B2  
APPLICATION NO. : 16/486448  
DATED : November 8, 2022  
INVENTOR(S) : Christopher Hadad et al.

Page 1 of 1

It is certified that error appears in the above-identified patent and that said Letters Patent is hereby corrected as shown below:

In the Claims

Column 75 Claim 12, Lines 17-22, the formula should appear as follows:

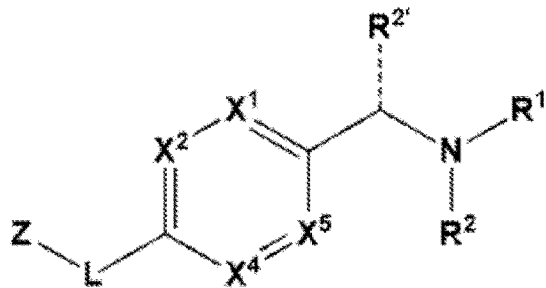

Column 75 Claim 14, Lines 49-58, the formula should appear as follows:

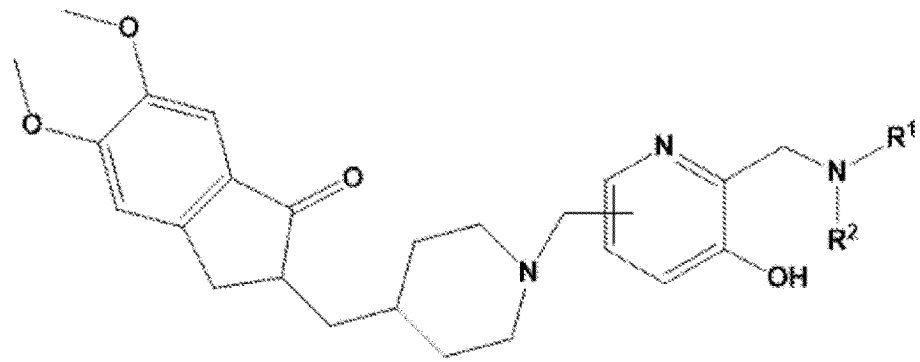

Signed and Sealed this  
Sixteenth Day of May, 2023

Katherine Kelly Vidal  
*Director of the United States Patent and Trademark Office*